(12) United States Patent
Hannapel et al.

(10) Patent No.: US 11,795,468 B2
(45) Date of Patent: Oct. 24, 2023

(54) NUCLEIC ACID CONSTRUCTS, PLANTS WITH INCREASED TUBER YIELD, AND METHODS FOR INCREASING TUBER YIELD IN A PLANT

(71) Applicants: Iowa State University Research Foundation, Inc., Ames, IA (US); Indian Institute of Science Education and Research (IISER), Maharashtra (IN)

(72) Inventors: David J. Hannapel, Ames, IA (US); Anjan K. Banerjee, Pune (IN)

(73) Assignees: Iowa State University Research Foundation, Inc., Ames, IA (US); Indian Institute of Science Education and Research (IISER), Pune (IN)

( * ) Notice: Subject to any disclaimer, the term of this patent is extended or adjusted under 35 U.S.C. 154(b) by 441 days.

(21) Appl. No.: 16/246,321

(22) Filed: Jan. 11, 2019

(65) Prior Publication Data
US 2019/0218565 A1  Jul. 18, 2019

Related U.S. Application Data

(60) Provisional application No. 62/616,565, filed on Jan. 12, 2018.

(51) Int. Cl.
*C12N 15/82* (2006.01)

(52) U.S. Cl.
CPC ..... *C12N 15/8261* (2013.01); *C12N 15/8226* (2013.01); *C12N 15/8234* (2013.01); *Y02A 40/146* (2018.01)

(58) Field of Classification Search
CPC .................... C12N 15/8226; C12N 15/8218
See application file for complete search history.

(56) References Cited

U.S. PATENT DOCUMENTS 7,579,150 B1 * 8/2009 Hannapel .............. C07K 14/415
    435/6.13
2013/0260012 A1 * 10/2013 Rommens .......... C12N 15/8218
    426/637

OTHER PUBLICATIONS

Ghate et al (Plant Mol Biol., 2017, 93: 563-578) (Year: 2017).*
PGSC0003DMG400019635 (published online Dec. 16, 2011) (Year: 2011).*
PGSC0003DMG400021323 (published online Dec. 16, 2011) (Year: 2011).*
PGSC0003DMG400005930 (published online Dec. 16, 2011) (Year: 2011).*
Sharma et al (Journal of Experimental Botany, 2014, 65(2): 709-723) (Year: 2014).*
Sol Genomics Description of Sequence Datasets (published online Jul. 2011).*
Ghate et al., "The Mobile RNAs, StBEL11 and StBEL29, Suppress Growth of Tubers in Potato," Plant. Mol. Biol. 93(6) 563-78(2017).

* cited by examiner

*Primary Examiner* — Mykola V. Kovalenko
(74) *Attorney, Agent, or Firm* — Troutman Pepper Hamilton Sanders LLP (Rochester)

(57) ABSTRACT

The present invention relates to a nucleic acid construct. The nucleic acid construct includes a nucleic acid molecule configured to silence or reduce the expression of StBEL11 and/or StBEL29 and variants thereof, a 5' DNA promoter sequence, and a 3' terminator sequence, where the first nucleic acid molecule, the promoter sequence, and the terminator sequence are operatively coupled to permit transcription of the first nucleic acid molecule. The present invention is also directed to vectors, host cells, transgenic plants, and transgenic plant seeds, as well as non-transgenic mutant plants, and methods for altering tuber yield in a plant.

17 Claims, 21 Drawing Sheets
Specification includes a Sequence Listing.

SEQUENCE LISTING

```
<160> NUMBER OF SEQ ID NOS: 53

<210> SEQ ID NO 1
<211> LENGTH: 2718
<212> TYPE: DNA
<213> ORGANISM: Solanum tuberosum L.

<400> SEQUENCE: 1
tttaagaaaa tctctcactt tctctttctc ccaattataa taagaaaact ttctttcctc      60
cttgttttta tttttaaaaa aatatttcag tttagtttat ggttgaagat atttgatata     120
gccttcatat atgtcactca tgttccatca tcagccaagt gttagaagtc actttcttta     180
acaagatttt cttgaaaaat atttaaaaaa ttgaactcca aaaaaaagaa aaaaggagt     240 gtagttttct tgattggttg tgaaatttat ggctatgtac tatcaaggag gctcagaaat     300
ccaagctgat ggtctgcaga cactttattt gatgaaccct aactatatag gctacactga     360
cacacatcat catcatcatc aacaccaaca acaatcagcc aacatgtttt tcttgaattc     420
```

```
tgtggcggcg gggaatttc cccacgtgtc cctcccttg caagcacatg cgcaggggca      480
cttggttgga gtgcccctgc cagctggttt tcaagatcct aaccgccctt ccattcagga      540
aattccgacc tctcatcatg gccttttatc gcgtttgtgg acttctggtg accaaaatac      600
ccctagaggt ggtggaggag gaggagaagg aaatggaagt caatcacata taccgtcttc      660
cacggtggtt tctcccaact caggtagtgg gggaggcacc accacggact ttgcttccca      720
attagggttc caaagaccgg ggttggtgtc accaacacag gcgcaccatc aaggtctttc      780
tctaagcctt tctccacaac aacaaatgaa tttcaggtct agtcttccac tagaccaccg      840
cgatatttca acaacaaatc atcaagttgg aatactatca tcatcaccat taccatcacc      900
aggaacaaat accaatcata ctcgaggatt aggggcatca tcgtcttttt cgatttctaa      960
tgggatgata ttgggttcta agtacctaaa agttgcacaa gatcttcttg atgaagttgt     1020
taatgttgga aaaacatca aattatcaga ggttggtgca aaggagaaac acaaattgga      1080
caatgaatta atatctttgg ctagtgatga tgttgaaagt agcagccaaa aaatagtgg      1140
tgttgaactt actacagctc aaagacaaga acttcaaatg aagaaagcaa agcttgttag     1200
catgcttgat gaggtggatc aaaggtatag acaataccat caccaaatgc aaatgattgc     1260
aacatcattt gagcaaacaa caggaattgg atcatcaaaa tcatacacac aacttgcttt     1320
gcacacaatt tcaaagcaat ttagatgttt aaaagatgca atttctgggc aaataaagga     1380
cactagcaaa actttagggg aagaagagaa cattggaggc aaaattgaag gatcaaagtt     1440
gaaatttgtg gatcatcatt tacgccaaca acgtgcacta caacaattag ggatgatgca     1500
aaccaatgca tggaggccac aaagaggttt gcccgaaaga gcggtttcgg ttctccgtgc     1560
ttggcttttc gagcattttc ttcatccgta tcccaaagat tcagataaaa tcatgcttgc     1620
taagcaaaca gggctaacaa ggagccaggt atcaaattgg tttataaatg ctagagttag     1680
actatggaag ccaatggtag aagaaatgta catggaagaa gtgaagaaaa acaatcaaga     1740
acaaaatatt gagcctaata acaatgaaat tgttggttca aaatcaagtg ttccacaaga     1800
gaaattacca attagtagca atattattca taatgcttct ccaaatgata tttctacttc     1860
caccatttca acatctccga cgggcggcgg cggttcgatt ccggctcaga cggttgcagg     1920
tttctccttc attaggtcat taaacatgga gaacattgat gatcaaagga acaacaaaaa     1980
ggcaagaaat gagatgcaaa attgttcaac tagtactatt ctctcaatgg aaagagaaat     2040
catgaataaa gttgtgcaag atgagacaat caaaagtgaa agttcaaca acacacaaac     2100
aagagaatgt tattctctaa tgactccaaa ttacacaatg gatgatcaat ttggaacaag     2160
gttcaacaat caaaatcatg aacaattggc aacaacaaca acactttc atcaaggaaa     2220
tggtcatgtt tctcttactc tagggcttcc accaaattct gaaaaccaac acaattacat     2280
tggattggaa aatcattaca atcaacctac acatcatcca aatattagct atgaaaacat     2340
tgatttcag agtggaaagc gatacgccac tcaactatta caagattttg tttcttgatg     2400
atatatataa tttgcaggta aatcagcttg aaattacatc atgaaaggcc ttgaataaaa     2460
gaagggagt tgagatctag tgatcatata aatatgtata ggtagaaagt ttagttagta     2520
tataggtt atacttctag tttcttaaat ggagatacaa ttttgttgt tattttgta      2580
ttgagataac tagctagctt ggattattta agttgttgc atgcaaccaa agaagaagaa     2640
aaaataatct atatatgcaa actatagtat gttgtaaatt ttgtgcgtct ttttgtttca     2700
atttgcatat atgtaaac                                                   2718
```

<210> SEQ ID NO 2
<211> LENGTH: 8025
<212> TYPE: DNA
<213> ORGANISM: Solanum tuberosum L.

<400> SEQUENCE: 2

| | | | | | |
|---|---|---|---|---|---|
| tttttttttat | gtatatatac | atttgatgaa | gataatgttc | tcttaagtga | aaatcttgct | 60 |
| tttatcatta | gttagtactt | acaattcttt | ctgtcttatt | ttatatgata | ttttttaaa | 120 |
| tttagtttac | cccgaaaata | aatgatatgt | ttttatatat | ttaactaatt | caattaact | 180 |
| aattcaattt | taaacttctt | tgaatctcaa | tcgaattgcc | tcatttttga | gaaggagttc | 240 |
| gatttcaaac | ccagattcga | tccactccaa | gaaaagaga | aagaaaaac | aaatcaacta | 300 |
| cgaaccccca | ccccacccca | cccaccccc | caccatcgga | aaaagggtca | taagtagaaa | 360 |
| taaagaaaaa | ttgagggact | tctagcaact | aatgtaatca | attatgtatt | atatatggac | 420 |
| ccaacaaatt | ggtggaaaaa | gacgtttcct | catttttcat | atatctatgg | cctacttcct | 480 |
| ttaagttaat | gtttttttc | ttcatctaat | tttaagtcga | gtatttattt | tgagactcgg | 540 |
| attaatttaa | attgatgttt | tcaggaaaat | ttatcaaaag | tgaaaatcta | acttattgag | 600 |
| aattttctta | tttgtatgat | ttaaatttgt | aacctctaaa | taaagatgaa | aaatcttaat | 660 |
| catttcatca | ttactcgtaa | ttattttctt | cttgttagtg | ttcactatac | tctctctttc | 720 |
| tctctaaaga | tattttgaa | aaaaatatc | taaattatgc | cagcatcaaa | tcatttata | 780 |
| atagtgaaat | taagattggg | tctatttatt | ttttccatca | cacgtatgta | gaacccccca | 840 |
| cccccaccct | cgccgccacc | ccaccccctt | actatcgagt | ttaactaata | tttattagta | 900 |
| taaaaattat | atttatctgt | tataacaagt | aaaatgtctt | attttaaaa | ggataaaggt | 960 |
| atgagaaata | tcccaacttt | gatcggattt | actgttgcga | tactaaactt | tcatgaggat | 1020 |
| ctattacctc | cttcgactat | ttaataccgt | attttatcc | ccctgaacta | tttaatattg | 1080 |
| tattttaaag | gtatatatga | ttatatgtgc | caacgtggac | acattactat | ttataattt | 1140 |
| gcattatttt | ttatgtccac | gtggacaaat | atatatgttt | aaaatacggt | attaaatagt | 1200 |
| ctagggagct | aataggtcct | catgaaagtt | tagtatcgca | acaacaaatt | cgatcaaagt | 1260 |
| tgagatattt | ttcaggccct | tatccctatt | tttaaaattg | aaagtttaca | tttttatgaa | 1320 |
| gggttaaaac | atgtaacatc | atttaggtaa | cttgatatag | tataaaaaat | tatttacatt | 1380 |
| atatataaat | taaattcatg | attactaaaa | gaattcaatc | atcaggtcat | ctttatctat | 1440 |
| gaaatgtttt | atttgtaaaa | ttacaaacct | cacatttaaa | aaagtttatc | tataaatata | 1500 |
| tttttaaata | accttcctga | taatgtaaaa | atatttatac | tgacgattct | tactgatttt | 1560 |
| ttttttactg | tgtttttgag | gggtgggtg | ggggtgaggg | taaggggat | atgttgggag | 1620 |
| acttacacta | aataaacatg | tcttctttat | tcatattccc | ctttatgtgt | tgtggagttt | 1680 |
| taagaaaatc | tctcactttc | tctttctccc | aattataata | agaaaacttt | ctttcttcct | 1740 |
| tgttttatt | tttaaaaaaa | tatttcagtt | tagtacatgg | ttgaagatat | ttgatatagc | 1800 |
| cttcatatat | gtcactcatg | tgagtacaac | ttttctccat | atatatcaaa | atcaagattt | 1860 |
| tcatagttga | gtgattaatt | aattgtatat | aactcatcat | atattatttg | aattttcttt | 1920 |
| gttaaaaatg | ttttctatct | ttagggtatt | gcatggattt | attataattt | ttttctatct | 1980 |
| tactttctaa | tttcaggttc | catcatcagc | caagtgttag | aagtcacttt | ctttaacaag | 2040 |
| attttcttaa | aaaatattta | aaaacttgaa | ctccaaaaaa | aagaagaaaa | ggagtgtaat | 2100 |
| tttcttgatt | ggttgtgaaa | tttatggcta | tgtactatca | aggaggctca | gaaatccaag | 2160 |

```
ctgatggtct gcagacactt tatttgatga accctaatta tataggctat actgacacac    2220
atcatcatca tcaacaacac caacaacaat cagccaacat gttttcttg aattctgtgg     2280 cggcggggaa ttttccccac gtgtccctcc ctttgcaagc acatgcgcag gggcacttgg    2340
ttggagtgcc cctgccagct ggttttcaag atcctaaccg cccttccatt ccggaaattc    2400
cgacctctca tcatggcctt ttatcacgtt tgtggacttc tggtgaccaa ataccccta    2460 gaggtggtgg aggaggagga gaaggaaatg gaagtcaatc acatataccg tcttccacgg    2520
tggtttctcc caactcaggt agtggggag gcaccaccac ggactttgct tcccaattag     2580
ggttccaaag accggggttg gtgtcaccaa cacaggcgca ccatcaaggt ctttctctaa    2640
gcctttctcc acaacaacaa atgaatttca ggtctagtct tccactagac caccgcgata    2700
tttcaacaac aaatcatcaa gttggaatac tatcaccatc accattacca tcaccaggaa    2760
caaataccaa tcatactcga ggattagggg catcatcgtc ttttttcgatt tctaatggga   2820 tgataatggg ttctaagtac ctaaaagttg cacaagatct tcttgatgaa gttgttaatg    2880
ttggaaaaaa catcaaatta tcagagggtg gtgcaaagga gaaacacaaa ttggacaatg    2940
aattaatctc tttggctagt gatgatgttg aaagtagcag ccaaaaaaat attgttgttg    3000
aacttactac agctcaaaga caagaacttc aaatgaagaa agccaagctt gttagcatgc    3060
ttgatgaggt atatatactt ctaattattc atatattaat taattaatca tatatatata    3120
ttaatcaaat tattcatata ttaattaatt aatcaatacc aagtttcttg atttggagtt    3180
tgatcattta ggcaaatttc actactatat ataaaacaca aattctaacg gatgtttggt    3240
cagtaagaaa ttctcaattt tcaatcaaac atctattaga atttcacgtt ttttagtagt    3300
gaaattaatt aaataatcta aaaattgttc aatcgaattt acaacaaaac atccattgaa    3360
attttacttt cttttcaata gcgaaaccaa ttaaatagga ttgactaccc aattaatagt    3420
tattatctta tcttcttctt gatttcaatc tttttttcaat aaaagagta attttaatta    3480 tgagataata aactactgat tagttatgac aatctgaaaa atcaactcct attaaatgat    3540
ccaaaaagtg tacaaatttg tatatcttaa tgttaatttc attgtttat ttatttattt     3600 agttgctttt tttttccttct tgggaagggg gagggtcaa gttgctattg attcatatac    3660
tagcaataat tattgattta tttcaaaggt acaattttgt tcatcatgaa actataagct    3720
agacaatata tgtggttcta agcttttttc tattgggggt ccaactaaag ttaaagataa    3780
tacacctaat atgtcttgtt gagttgacaa aaaatcaaag gcacgtggtc ttattcaatc    3840 acttttattag aaccttttcaa atttggaaat attcttacct ttcttttgag ataatcacat   3900
aaaaataaac ctttggaata atttatattt ttggtattcc tattgatatt tgatatctgt    3960
tttgaagctt aactaatata aatatgcgtc gaaaagttat ctcactttag gagattaaaa    4020
tgcttcttag taaaagtgac ttcatattca ggactcgaat aatattactt gatgatcatt    4080
tggacacaat tgatcaattg ggaaataatg aaatattatt ttgcaaatca gtttttattt    4140
tataatttca ttagttattt cgacttgaac ttgaaataaa gaatctgaag tttgaaaaat    4200
tgatttaaag agtatttttt tccactctaa gaacttcaaa caatttcaac ttcaacttca    4260
tataatcata ttttttttca acttcaatca gatatcgtcg tgatatgatc aatatcaatc    4320
tacttatttt tattttattg tttgtatttt ttttgaatt tttatagggt ggatcaaagg     4380
tatagacaat accatcacca aatgcaaatg attgcaacat catttgagca acaacagga    4440 attggatcat caaaatcata cacacaactt gctttgcaca caatttcaaa gcaatttaga   4500
```

```
tgtttaaaag atgcaattttt tgggcaaata aaggacacaa gtaaaacttt aggggaagaa    4560
gagaacattg gaggcaaaat tgaaggatca aagttgaaat ttgtggatca tcatttacgc    4620
caacaacgtg cactacaaca attagggatg atgcaaacca atgcatggag gccacaaaga    4680
ggtttgcccg aaagagcggt ttcggttctc cgcgcttggc ttttcgagca ttttcttcat    4740
ccgtaagtat ttgttgaaga cataattaag taaattaata tgcatgtctt ttaatagttt    4800
aagattttaa acaaagcaat cacaacatcc tacatgtttc accgcttgtt ctccttatta    4860
ggaaaaataa ccaattgttc tagagtatat gagaaagaat cagactcgca atctagcatt    4920
tgaagtggca aatacaagac taattaagta aatacaattt ttttttttaa ataacagtt    4980 taaactttg aatgagatag atttaattaa caccttatat tacctataag aaatgaactt    5040
caatctctat ttttttttta aaacaattt tatacaccat gtagaaacct ttataaagaa    5100
attaaattaa atcactcata ccatttcttt taaatttcaa taaataaatt atatatttct    5160
tgtcttgcag gtatcccaaa gattcagata aaatcatgct tgctaagcaa acagggctaa    5220
caaggagcca ggttcttgaa aaattcatca tctcaattta tatgacgcat ttttttaacat    5280 atctaaaaaa gacgtttat ttctaattta gaaacaataa aatttaaaa ttctcaacaa    5340 tcatagtacc tctctatata actgtaacaa catcttatta taacaaccaa ttttttgaat    5400
atgccgtaaa aaagacatta tattttcaat ttaggaacaa tataacttta aaattctcaa    5460
caatcatagt acctctctat ataactgtaa caacatctta ttataacaac cattttttg    5520 aatatgccgt aaaaagaca ttatattttc aatttaggaa caatataact ttaaaattct    5580
caacaatcat agtacctctc tatataacag taacaacatc ttgttataac aaactaagtt    5640
cttttttaaa ccaactttca ctacaacaaa gataacttt agcggcaata tacatattaa    5700
taaagaatac taaagctttt accggcatta gttaatttca ttggatccat tatcgctata    5760
gactgtagat acatttacaa aaagtattaa ttaccactaa aaacacatat gtagtggcaa    5820
ttttgctatt gctattaatt aattaatgtt ataaatataa ttttttaatgt agtgtttcat    5880 gttatgttaa agtcatgtag tatatgttct ctacgaataa tatttcacta tatcagacaa    5940
aaaatatcta gaataaacaa tgatgttata gaaagatttg acagcaagtc acacaaatat    6000
gtacttaaga gtacttattt tagactacaa gttttaaaag tcgatcgtct gttctttctt    6060
aaaatacttt tgaaaatgca ggtatcaaat tggtttataa atgctagagt tagactatgg    6120
aagccaatgg tagaagaaat gtacatggaa gaagtgaaga aaaacaatca agaacaaaat    6180
attgagccta ataacaatga aattgttggt tcaaaatcaa gtgttccaca agagaaatta    6240
ccaattagta gcaatattat tcataatgct tctccaaatg atatttctac ttccaccatt    6300
tcaacatctc cgacgggtgg cggcggttcg attccggctc agacggttgc aggttagttg    6360
gaatataaag aaagtcattt taaagttgt cgttgtttga cctataatag gttttgagtc    6420
gtggaaggca tcactaattt gcataaaggt aggttgtccc cttggggtat ggtcttttca    6480
tggagtaacg gtagagttgt ttccactgac ctatataagt tacaggttcg agttgtggaa    6540
ttggttgcgt tgttgatgct catgtcgggg tagactgtct acaacacaca ccttgagata    6600
caacctttta ttgtacccta catgaatgtg aaatacttca cgcaccaaac tgcctaataa    6660
ctcttagaaa agaacacact tgactcacac atctatatat ctacgtagta cctcaattga    6720
taaataatct aggatgatta gatggttaca catatcaaac atataatagg ttcaagtcgt    6780
agaaggcgtc actaatttgc atcaaggtag gttgtcccct tggggtatga tcctttcatg    6840
gaccatgtag acactcttga agttgagtct tgaagtaaca gtaaagtcat ctccacgtga    6900
```

```
cctatatata taagtcacaa cttcgagttg tggagttggc taggctctca tcaggataga    6960
ctgtcgacat cacacttctt gaaatgcaac ctttttccga accttatgtg aatgtgagac    7020
tacactcttg actaacatct atataactac tatacctcaa ttaataaaca atctaggata    7080
attagatggt ctcacactct aaacacctag gttagatcaa aagacaataa aactagctag    7140
agtacatttt tatttattgt aacaagtgtt acttatcaaa gtgtgactct atattgttta    7200
actaattaac atgtttaatt tgtctaaaca ggtttctcct tcattaggtc attaaacatg    7260
gagaacattg atgatcaaag gaacaacaaa aaggcaagaa atgagatgca aaattgttca    7320
actagtacta ttctctcaat ggaaagagaa atcatgaata aagttgtcca agatgagaca    7380
atcaaaagtg aaaagttcaa caacacacaa acaagagaat gctattctct aatgactcca    7440
aattacacaa tggatgatca atttggaaca aggttcaaca atcaaaatca tgaacaattg    7500
gcaacaactt ttcatcaagg aaatggtcat gtttctctta ctctagggct tccaccaaat    7560
tctgaaaacc aacacaatta cattggattg gaaaatcatt acaatcaacc tacacatcat    7620
ccaaatatta gctatgaaaa cattgatttt cagagtggaa agcgatacgc cactcaacta    7680
ttacaagatt tgtttcttg atgatatata taatttccag gtaaatcaac ttgaaattac    7740
atcatgaaag gccttgaata aaagaagggg agttgagatc tagtgatcat atatatatgt    7800
ataggtagaa agtttagtta gtatatatag gttatacttc tagtttctta aatggagata    7860 caattttgt tgttgttttt gtattgagat aactagctag cttgggttat ttaaagttgt    7920
tgcatgcaac caaagaagaa gaaaaaataa tctatatatg caaactatag tatgttgtaa    7980
attttgtgct tcttttaatt agtttcaatt tgcatatatg taaac                     8025

<210> SEQ ID NO 3
<211> LENGTH: 401
<212> TYPE: DNA
<213> ORGANISM: Solanum tuberosum L.

<400> SEQUENCE: 3
gaaatttatg gctatgtact atcaaggagg ctcagaaatc caagctgatg gtctgcagac      60
actttatttg atgaacccta actatatagg ctacactgac acacatcatc atcatcatca     120
acaccaacaa caatcagcca acatgttttt cttgaattct gtggcggcgg ggaattttcc     180
ccacgtgtcc ctcccctttgc aagcacatgc gcagggcac ttggttggag tgccctgcc     240 agctggtttt caagatccta accgcccttc cattcaggaa attccgacct ctcatcatgg     300 cctttatcg cgtttgtgga cttctggtga ccaaaatacc cctagaggtg gtggaggagg     360
aggagaagga aatggaagtc aatcacatat accgtcttcc a                          401

<210> SEQ ID NO 4
<211> LENGTH: 2898
<212> TYPE: DNA
<213> ORGANISM: Solanum tuberosum L.

<400> SEQUENCE: 4
ttctttcttt ctttctcctc tctctctctc taaaaagttg agtacttta ttagctctca       60 tcacttcaca cagaagaaga tggtattttt atttctttct gctgatggct gcatcaaatg     120
atttgaaaag ctgagtcaaa tcagaagaag aaaagaaag ttataataat aataatgata     180
atatcaaaaa tattatttc agattagttg gtgttatttg tttattgtgg agaaaaaata     240
aattaaaaag gaagaaaaaa tggcatctta ttttcatgga aattcagaaa tacatgaagg     300
```

```
aaatgatgga ttacaaactc taatactaat gaatcctgga tatgttggat tttctgaaac    360
acaacatcac cacgcgccac cgccgccgcc gccaggtggc agcagcagca acatagtttt    420
cttcaactcc aatcctattg gaaattcaat gaacttatct cacgcgccac cacctcctcc    480
accgcctcaa caacaattca tcggtatacc cctcgccacc gccgccttca ccgcccatc     540 ccaagactcc ggtaacaaca acaacaacga gtcaatctcc gcccttcacg gcttcctagc    600
tcgatcgtct cagtacgggt tttacaaccc ggcaaacgac ctcacggcgg cgcgtgacgt    660
cacacgcgct catcatcatc atcagcagcc aagggctttc acttacctgt cctcgtccca    720
gcagccgggg tttgggaact tcacggcggc gcgtgagctt gtttcttcgc cttcgggttc    780
ggcttcagct tcagggatac aacaacaaca acagcaacaa cagagtatta gtagtgtgcc    840
tttgagttct aagtacatga aggctgcaca agagctactt gatgaagttg taaatgttgg    900
aaaatcaatg aaaagtacta atagtactga tgttgttgtt aataatgatg tcaagaaatc    960
gaagaatatg ggcgatatgg acggacagtt agacggagtt ggagcagaca aagacggagc    1020
tccaacaact gagctaagta caggggagag acaagaaatt caaatgaaga aagcaaaact    1080
tgttaacatg cttgacgagg tggagcagag gtatagacat tatcatcacc aaatgcagtc    1140
agtgatacat tggttagagc aagctgctgg cattggatca gcaaaaacat atacagcatt    1200
ggctttgcag acgatttcga agcaatttag gtgtcttaag gacgcgataa ttggtcaaat    1260
acgatcagca agccagacgt taggcgaaga agatagtttg ggaggaagaa ttgaaggttc    1320
aaggcttaaa tttgttgata atcagctaag acagcaaagg ctttgcaac aattgggaat    1380 gatccagcat aatgcttgga gacctcagag aggattgccc gaacgagctg tttctgttct    1440
tcgcgcttgg cttttttgaac atttcctcca tccttatccc aaggattcag acaaaatgat    1500
gctagcaaaa caaacaggac taactaggag tcaggtgtcg aattggttca tcaatgctcg    1560
agttcgtctt tggaagccaa tggtggaaga gatgtacttg aagagataa aagaacacga    1620 acagaatggg ttgggtcaag aaaagacgag caaattaggt gaacagaacg aagattcaac    1680
aacatcaaga tccattgcta cacaagacaa aagccctggt tcagatagcc aaaacaagag    1740
ttttgtctca aaacaggaca atcatttgcc tcaacacaac cctgcttcac caatgcccga    1800
tgtccaacgc cacttccata cccctatcgg tatgaccatc cgtaatcagt ctgctggttt    1860
caacctcatt ggatcaccag agatcgaaag catcaacatt actcaaggga gtccaaagaa    1920
accgaggaac aacgagatgt tgcattcacc aaacagcatt ccatccatca acatggatgt    1980
aaagcctaac gaggaacaaa tgtcgatgaa gtttggtgat gataggcagg acagagatgg    2040
attctcacta atgggaggac cgatgaactt catgggagga ttcggagcct atcccattgg    2100
agaaattgct cggtttagca ccgagcaatt ctcagcacca tactcaacca gtggcacagt    2160
ttcactcact cttggcctac acataacga aaacctctca atgtctgcaa cacaccacag    2220
tttccttcca attccaacac aaaacatcca aattggaagt gaaccaaatc atgagtttgg    2280
tagcttaaac acaccaacat cagctcactc aacatcaagc gtctatgaaa ccttcaacat    2340
tcagaacaga aagaggttcg ccgcaccctt gttaccagat tttgttgcct gatcacaaaa    2400
acaaaaacag gttttggcaa cagacaaact tctgtcgcta acaaggaca tgatttagcg    2460 acagataact tcagtcgcta acttagcgac tgaaaacttc tgtcgctaag catgaacatg    2520
tattagcgac atacagtatg caactgtatg tcactaaaca agaacatgat gaattagtga    2580
cggacaactt ctgtcgctaa acaacaaaaa aaaatccatg ttttagtata ttgtttctca    2640
ttctatcata tcatggtagt gtaaagaatc aagaaacaag ttttacatag taacagtctt    2700
```

-continued

| | |
|---|---|
| tatacattgg agatgaagaa ccatttaagt tcttcaaaat agatagattt tctaggttac | 2760 |
| ttctacaaga tatatatatg gttgagggtt tgtatattaa ttttgggatt gttatattgg | 2820 |
| atgtggaaaa aaagtagtta ttttgggtgg tataaataaa ataatactcc atccatttta | 2880 |
| gccaaaaaaa aaaaaaaa | 2898 |

<210> SEQ ID NO 5
<211> LENGTH: 7921
<212> TYPE: DNA
<213> ORGANISM: Solanum tuberosum L.

<400> SEQUENCE: 5

| | |
|---|---|
| tgagaagaaa acccaaagaa acttatgatt tataataaat tattagaaat ttctatggat | 60 |
| ataaaatggt aaaagtaagt ttttattaaa tataaaaata tgttttttt aatggaataa | 120 |
| aaagcaaaaa aaatcacat aaattagaat aaagatcgga gaaagtaaat tataaataaa | 180 |
| gacaagatga aaaacaaggc gataatgtaa atcatactaa tcaatcgtta tacatattaa | 240 |
| aaaatatcca gcgttacaac aacaaattta acaatataat ataataaaat ttaactaaaa | 300 |
| atcaaaataa aatgacattt atcataacaa taattaacaa ccatccaaat atgatgtatg | 360 |
| gataaaaggt gaagagtatt agtatctttt gtttaaatct tatatattaa aattataaat | 420 |
| ttaattatta ttttaaaaat tcttatataa attttaaatt ctgaatttgt ccgacggcta | 480 |
| atctaaagtc aaaagtaaat tttcataaat gtaggtccta aattttttcc cacaattatc | 540 |
| ttcttccaag ttgccaacac aaatcaataa tgacaatagg gccctctccc ctatctcttc | 600 |
| aaccctacct ctcttttttct ttctttatca cttcaagttc atatcatatt tcatactctc | 660 |
| tcattttctt ctggtctccg ttgtaattta tatgatatat tttttaatat ttaaaataat | 720 |
| ttaattttaa atttttttata ctctttaaaa aattattata atcataagtt ataaaaaaaa | 780 |
| ttaactttt tttattcagt caaatactat catataaatt aaaaaagaaa aagtatatgt | 840 |
| taaatcctta taattattat tgttaaagaa gaaaaaggg aggttagtgg aagtggacgt | 900 |
| tacctcgttt ttcatctgtc tgttttttct gacacacctt tgatctttga tgatggatac | 960 |
| gtcgctccgt tcatatttag gtgatactat attaatttca agagttaaat aatgataaat | 1020 |
| cacctaagac cgctaatgtt ccatctaatt caagaacaag cccttctcaa tgtcttgcct | 1080 |
| ttcgcatgtg ttttctttga aattggaatt ccaaccaagt tcccttccca aagcgggaac | 1140 |
| aagttggtgc gaccgattaa agaagaagga caaagagtta aataatgaaa ttataattat | 1200 |
| tttatattaa ttattataat ttataatatt ttttaaaaac taaatgttct aatttaaagg | 1260 |
| caaagtccaa atatttattt tataaatttt gaagcataat tgggttttga ttaattattt | 1320 |
| atatcaaatt aaatttattt taatacaaat acataattta agacaaagct attgagttaa | 1380 |
| agttatgtca aattaaatcc gtaactttat aagctcaagg ggagaaagag agaaggattg | 1440 |
| ttcattcctt ataacgagtc tagagatctc atcctttatc gatgtaaggt tctttccatt | 1500 |
| catcactccc ttgcgttaga acctttttttt tttagactgg agcgtgcaca ttcatggacc | 1560 |
| attcttccca ttcgtcaatc cctcgtgtta gaatttttat ttctcgaact agagtgtgtg | 1620 |
| cattaacaga taccagatac cgatattttc accctcattc aagccgtctc tggaagagct | 1680 |
| atattggatg agcctgactt tgataccata tcaaattaac tcttcaacct aattcataca | 1740 |
| tcaaaagcta gctcgcctta taagaagtct ttccattcgt cactccctcg tgttacaact | 1800 |
| tacaagacta gctcaataaa aaattatcgt ccaaatttta taagaagtcc attcatcaat | 1860 |

```
agcaccttcc ctatttgtat ttgcacttaa aaaaaaaaag gtgacttttg aaatttgaat    1920
tatgccacat aaattatcct tcggtatagc ccaatgattt gaccttggta ctttcatatt    1980
ggaggtctca aatttgaaat tccttaccag taaaaataaa aaatttacct tcctgaatcg    2040
aacttatcgc gccagacttc cttagacaca caaattagaa taaaaaaagt atattttatt    2100
tttatatata agcaaaaaca cacactaact cacattcaca catccacatc tttcttctt     2160
tctttctcct ctctctctct ctaaaaagtt gagtacttt  attagctctc atcacttcac    2220
acagaagaag atggtatttt tatttctttc tgctgatggc tgcatcaaat gatttgaaaa    2280
gctgagtcaa atcagaagaa gaaaagaaa  gttataataa taataataat aatatcaaaa    2340
atattatttt caggtatggt acttcttac  tcattaacaa tgtaaatata gaatttgaag    2400
tttacgagct agttttctct tctttttat  tttgactagc agaaacagag tcagagtcag    2460
aatttgaagt ttataagtct tgaattctga ttttgtttga gttcttgagt tctgaattga    2520
taatttatac atgttgaatg aattttgtaa gtatactttg aaacaaatct attgagttcg    2580
attgaattca taaccgacac tttagttccg ccacttttca gaggcggatc cagaatatga    2640
aggttatgac ttatgagtat tgtaaccttt tgagttactg aattctaaat taattttata    2700
agtgagtaaa tacaaaattt gaaacaaaat tagctattga gttcagttga attcgtataa    2760
ccgacactct agctttgtca ctgctcaaag actgatctag aatttgaagt ttatgagttt    2820
tgaattctaa attgataatt tctacatgtt agatggaatt tttaagataa atataaatta    2880
aaattattga gttcgatcga attcgatttg tgttttcctt tttcttcacc ttatttatca    2940
agagaaatta ttttaatttt tttttatcat tactgattca taaatctata tagatatata    3000
tagatggata cattagagtt cctaaaaaat gttataaaga gtattttgtt tttcccttc     3060
ttgatttttt ttcgaaacta agatttcaat tttatcattt ctgaattta  taacaacgat    3120
tatcatagaa ttctaaattt actagttata catatttatt taacgaatta ttaacataaa    3180
tgcattattt gaataaaatt tattagattt gaccgaactc gtatatgaac tttctctctc    3240
atgtaatttc agccgtaact gtgtgtattt cctttctctc tctaaaaaat ctgttatggt    3300
gttctgtgtc actctaacaa aaaataaatt attcttcatt tcttccattg tcagattata    3360
atacaccacg tgcacttaca aattttgtga aaaccatatt ttaatttaca aatccttttc    3420
ataattcttt tttttaatca agaaaattaa atttaattac attaagtatt ttttacaata    3480
atattaacat attactaaat aaaattttcag gtttattta  ccattttgt  gattttgaag    3540
tgttacaaag tgtgaatggg ttggactttt tggacctcag ctaggtagct tcttgtcttc    3600
aacacaaaag gtacatataa aaattacaat aaaattataa ccactttac  ttaggaatt     3660
taccatattt aggtaaaaaa aataaatcac tcgcctagtc gtaataatca gtagcagagc    3720
tagaggaacg aaaggcttca tctgaatctt ctttatctga aatcatactg tatataaggt    3780
caaaattcat ttttatgaa  cacttttgat gaaaatcatg tctctgccac taaagtcgta    3840
atttgtaggc atcaacaata tgtatatata tatatatata gtgattattg attatatacg    3900
gtatatattg gttaaaagtt ttgaaaaata aggattaaag ttaatttcca ttgtgtgttt    3960
tcttgggatc aggggcggag ctagataagt gtaaaaggg  tttatctaga cttcttccga    4020
ccaaaaatta tacttatata catatacata gtagatactg aatcccttgc ttttttcgta    4080
tatgtacttc cgcatatttt aaatttcttt aatgaaaatt ctgactcata tactgtttga    4140
atgtttttgt atttaatata tgtatgtttt gcctttttat tttggaaaaa atgatatatg    4200
tggacttact tgacttgact ttaacttatt ttttttatt  tttcagatta gttggtgtta    4260
```

```
tttgtttata gtggagaaaa aataaattaa aaaagaagag aaaatggcat cttattttca   4320
tggaaattca gaaatacaag aaggaaatga tggattacaa actctaatac taatgaatcc   4380
tggatatgtt ggattttctg aaacacaaca tcaccacgcg ccgccgccgc caggtggcag   4440
cagcaacaac atagttttct tcaactccaa tcctcttgga aattcaataa acttatctca   4500
cgcgccacca cctccgccac cgccacaaca acatttcgtc ggtatacctc tcgccaccgc   4560
cgccttcacc gccccatccc aagactccgg taacaacaac aacaacgagt caatctccgc   4620
ccttcacggc ttcctagctc gatcgtctca gtacgggttt tacaacccgg ctaacgacat   4680
cacggcggcg cgtgaggtca cacgcgctca tcatcagcag cagcaagggc tttcacttag   4740
cctgtcctca tcccagcagc ctgggtttgg gaacttcacg gcggcgcgtg agattgtttc   4800
ttcgcctacg cgttcggctt cggcttccgg gatacaacaa caacaacagc aacaacaaag   4860
tattagtagt gtgcctttga gttctaagta catgaaggct gcacaagagc tacttgatga   4920
agttgtaaat gttggaaaat caatgagaag tactaatagt actgaagttg ttgttaataa   4980
tgatgtcaag aaatcgaaga ttatgaccga tatggatgga cagatagatg gaggagcaga   5040
caaagacgga actccaacaa ctgagctaag taccgcagag aggcaagaaa ttcaaatgaa   5100
gaaagcaaaa cttgttaaca tgcttgacga ggtaaccttg ttgtcttttt ctcagtaatg   5160
ttgttgcatt cgtgtcagat cagagtctta aaattagtca atagaagaaa cttcatttcc   5220
tcgagtacgt gtaattgtgg cctttttcgac ttccaactag tatttacaat agtgcactct   5280
acattgataa gcttgacgac aagtaggcaa agcgatggcc ttgttggttg ttatagtttt   5340
ttggttatgt tgctcggact ctgcaaaatt attgtcatac tcaagtcaga ttctccaaaa   5400
tgcactattt ttggagtatc cgacttgcag tctgacattt attttttccg aagagtctga   5460
gcaacatagg ttttcttggc tttccaagat agtaagagaa tggtctctat caaaaaaagt   5520
tacatcatat cattactgaa aataagagca aaaaagtatc tgtcaaatga taagaccag    5580
aacttcaaaa ctgttacttt cgtcagggca ctgtcttgac aattgtaaac aaaaaatgaa   5640
agaattttc gaaaataatt tcttcgaaat ctttgatcta aagctaaata tcggttcgat    5700
tttgggtgtt gttatatagg tggagcagag gtatagacat tatcatcacc aaatgcagtc   5760
agtgatacac tggttggagc aagctgctgg tattggatca gcaagaacat atacagcatt   5820
ggctttgcag acgattcga agcaatttag gtgtcttaag gacgcgataa ttggtcaaat    5880
acgatcagca ggcaagacgt taggcgaaga agatagtttg ggagggaaga ttgaaggttc   5940
aaggcttaaa tttgttgaca atcagctaag acagcaaagg gctttgcaac aattgggaat   6000
gatccagcat aatgcttgga gacctcagag aggattgccc gaacgagctg tttctgttct   6060
tcgcgcttgg cttttgaac atttcctcca tccgtaagca cgaaacaacc cttttcatc     6120
agctatgttg ctcggacttt tcaaaaacgt tgtcgcacca gtgttggatc ctcgcagaat   6180
gcattgattt tttgaggatc cgacacatac ctgacgatat ttttgaagag tctgaacaac   6240
atagcttagt taaaagtact gtattttgat atattgtggc aatttgtttt gtatagctat   6300
cccaaggatt cagacaaaat gatgctagca aaacaaacag ggctaactag gagtcaggtc   6360
agtgatatct gataacaaca ttgtcatttt tgattctcga gttgatttct cagatggtca   6420
cttaactgta gttattatat cagaaagtcg ccttacttca acaaagagag tgacattctg   6480
agataataac tgtgagttga gtgaccatct gagaaatcaa ctcttggatt ctccgttttt   6540
ggttttact aagtttgtt tttggacaat tcaggtgtcg aattggttca tcaatgctcg     6600
```

-continued

```
agttcgtctt tggaagccaa tggtggaaga gatgtacttg gaagagataa agaacagaa    6660 cggattgggt caagaaaaga cgagcaaatt aggcgaacag aacgaagatt caacaacatc    6720
aagatccatt gctacacaag acaaaagccc tggttcagat agccaaaaca agagtttttgt   6780 ctcaaaacag acaatcatt tgccccaaca caaccctgct tcaccaatgc cgatgtccaa     6840
caccacttcc atacctccta tcggtatgaa catccgtaat cagtctgctg gtttcaacct    6900
cattggatca ccagagatcg aaagcatcaa cattactcaa gggagtccaa agaaaccaag    6960
gaacaacgag atgttgcatt caccaaacag cattccatcc atcaacattg atgtaaagcc    7020
taacgagcaa caaatgtcga tgaagtttgg tgatgatagg caagacagag atggattctc    7080
actaatggga ggaccgatga acttcatggg aggattcgga gcctatccca ttggagaaat    7140
tgctcggttt agcaccgagc aattctcagc accatactca accagtggca cagtttcact    7200
cactcttggc ctaccacata cgaaaaacct ctcaatgtca gcaacacacc acagtttcct    7260
tccaattcca acacaaaaca tccaaattgg aagtgaacca aatcatgagt ttggtagctt    7320
aaacacacca acatcagctc actcaacatc aagcgtctac gaaaatttca acattcagaa    7380
cagaaagagg ttcgccgcac ccttgttacc agattttgtt gcctgatcac aaaaacaaaa    7440
acaggattta gcgacagaca aacttctgtc gctaaacaag aacatgattt agcgacagat    7500
aacttcagtc gctaacttag cgactgaaaa cttctgtcgc taaacatgaa catgtattag    7560
cgacatacag tatacaactg tatgtcgcta acaagaaca tgatgaatta gtgacggaca    7620
acttctgtcg ctaaacaaca aaaaagatc catgttttag tatattgttt ctcattctat    7680
catatcatgg tagtgtaaag aatcaagaaa caagttttac atagttacat agtctttata    7740
cattggagat gaagaaccat ttaagttctt caaaatagat agattttcta ggttacttct    7800
agaagatata tatatggttg aggggtttgta tattaattttt gggattgtta tattggatgt   7860
ggaaaaaaag tagttatttt gggtggtata aataaaataa tactccatcc attttagcca   7920
a                                                                      7921
```

<210> SEQ ID NO 6
<211> LENGTH: 799
<212> TYPE: DNA
<213> ORGANISM: Solanum tuberosum L.

<400> SEQUENCE: 6

```
gtgttatttg tttattgtgg agaaaaaata aattaaaaag gaagaaaaaa tggcatctta     60
ttttcatgga aattcagaaa tacatgaagg aaatgatgga ttacaaactc taatactaat   120
gaatcctgga tatgttggat tttctgaaac acaacatcac cacgcgccac cgccgccgcc   180
gccaggtggc agcagcagca acatagtttt cttcaactcc aatcctattg gaaattcaat   240
gaacttatct cacgcgccac cacctcctcc accgcctcaa caacaattca tcggtatacc   300
cctcgccacc gccgccttca ccgccccatc ccaagactcc ggtaacaaca caacaacga   360 gtcaatctcc gcccttcacg gcttcctagc tcgatcgtct cagtacgggt tttacaaccc    420
ggcaaacgac ctcacggcgg cgcgtgacgt cacacgcgct catcatcatc atcagcagcc    480
aagggctttc acttacctgt cctcgtccca gcagccgggg tttgggaact tcacggcggc    540
gcgtgagctt gttttcttcgc cttcgggttc ggcttcagct tcagggatac aacaacaaca    600
acagcaacaa cagagtatta gtagtgtgcc tttgagttct aagtacatga aggctgcaca    660
agagctactc gatgaagttg taaatgttgg aaaatcaatg aaaagtacta atagtactga    720
tgttgttgtt aataatgatg tcaagaaatc gaagaatatg ggcgatatgg acggacagtt    780
```

```
agacggagtt ggagcagac                                                  799
```

<210> SEQ ID NO 7
<211> LENGTH: 2735
<212> TYPE: DNA
<213> ORGANISM: Solanum tuberosum L.

<400> SEQUENCE: 7

```
catgcagaga taaaaatata gatcagtctg acaagaaggc aacttctcaa agcttagaga      60
gctaccaccc gaagatagac agttagttac atgtactgtt atagataaaa ggagaaatcc    120
gaagaagaaa gaatttttt tgcagatatg tactatcaag gaacctcgga taatactaat    180
atacaagctg atcatcaaca acgtcataat catgggaata gtaataataa taatattcag    240
acactttatt tgatgaaccc taacaattat atgcaaggct acactacttc tgacacacag    300
cagcagcagc agttactttt cctgaattct tcaccagcag caagcaacgc gctttgccat    360
gcgaatatac aacacgcgcc gctgcaacag cagcactttg tcggtgtgcc tcttccggca    420
gtaagtttgc acgatcagat caatcatcat ggacttttac agcgcatgtg aacaaccaa    480
gatcaatctc agcaggtgat agtaccatcg tcgacggggg tttctgccac gtcatgtggc    540
gggatcacca cggacttggc gtctcaattg gcgtttcaga ggccgattcc gacaccacaa    600
caccgacagc agcaacaaca gcaaggcggt ctatctctaa gcctttctcc tcagctacaa    660
cagcaaatta gtttcaataa caatatttca tcctcatcac caaggacaaa taatgttact    720
attaggggaa cattagatgg aagttctagc aacatggttt taggctctaa gtatctgaaa    780
gctgcacaag agcttcttga tgaagttgtt aatattgttg gaaaaagcat caaaggagat    840
gatcaaaaga aggataattc aatgaataaa gaatcaatgc ctttggctag tgatgtcaac    900
actaatagtt ctggtggtgg tgaaagtagc agcaggcaga aaaatgaagt tgctgttgag    960
cttacaactg ctcaaagaca agaacttcaa atgaaaaaag ccaagcttct tgccatgctt   1020
gaagaggtgg agcaaaggta cagacagtac catcaccaaa tgcaaataat tgtattatca   1080
tttgagcaag tagcaggaat tggatcagcc aaatcataca ctcaattagc tttgcatgca   1140
atttcgaagc aattcagatg cctaaaggat gcaattgctg agcaagtaaa ggcgacgagc   1200
aagagtttag gtgaagagga aggcttggga gggaaaatcg aaggctcaag actcaaattt   1260
gtggaccatc atctaaggca acaacgcgcg ctgcaacaga taggaatgat gcaaccaaat   1320
gcttggagac cccaaagagg tttacctgaa agagctgtct ctgtccttcg tgcttggctt   1380
ttcgagcatt ttcttcatcc ttacccaaag gattcagaca aaatcatgct tgctaagcaa   1440
acggggctaa caaggagcca ggtgtctaac tggttcataa atgctcgagt tcgattatgg   1500
aagccaatgg tagaagaaat gtacttggaa gaagtgaaga atcaagaaca aaacagtact   1560
aatacttcag gagataacaa aaacaaagag accaatataa gtgctccaaa tgaagagaaa   1620
catccaatta ttactagcag cttattacaa gatggtatta ctactactca agcagaaatt   1680
tctacctcaa ctatttcaac ttcccctact gcaggtgctt cacttcatca tgctcacaat   1740
ttctccttcc ttggttcatt caacatggat aatactacta ctactgttga tcatattgaa   1800
aacaacgcga aaaagcaaag aaatgacatg cacaagtttt ctccaagtag tattcttttca   1860
tctgttgaca tggaagccaa agctagagaa tcatcaaata aagggtttac taatcccttta   1920
atggcagcat acgcgatggg agattttgga aggtttgatc ctcatgatca acaaatgacc   1980
gcgaatttc atggaaataa tggtgtctct cttactttag gacttcctcc ttctgaaaac   2040
```

| | |
|---|---|
| ctagccatgc cagtgagcca acaaaattac ctttctaatg acttgggaag taggtctgaa | 2100 |
| atggggagtc attacaatag aatgggatat gaaaacattg attttcagag tgggaataag | 2160 |
| cgatttccga ctcaactatt accagatttt gttacaggta atctaggaac atgaatacca | 2220 |
| gaaagtctcg tattgatagc tgaaaagata aaggaagtt agggatactc ttatattgtg | 2280 |
| tgaggccttc tggcccaagt cggaggaccc aatttgatac aacctatcat aggagaaaag | 2340 |
| aagtggagac taaattaaag taacaaaatt ttaaagcaca ctttctagta tatatacttc | 2400 |
| tttttttat agtatagaaa agaagagatt ttgtgcttta gtgtatagat agagtctact | 2460 |
| tagtataggt tatacttcta gttccttgag aagattgata caactagtag tattttttt | 2520 |
| cttttgggtt ggcttggagt actattttaa gttattggaa actagctata gtaaatgttg | 2580 |
| taaagttgtg atattgttcc tctcaatttg catataattt gaaatatttt gtacctacta | 2640 |
| gctagtctct aaattatgtt tccattgctt gtaattgcaa ttttatttga attttgtgct | 2700 |
| atcattatta gattagcaaa aaaaaaaaaa aaaaa | 2735 |

<210> SEQ ID NO 8
<211> LENGTH: 4015
<212> TYPE: DNA
<213> ORGANISM: Solanum tuberosum L.

<400> SEQUENCE: 8

| | |
|---|---|
| gtaggtacaa atatttcaa attatatgca aattgagagg aacaatatca caactttaca | 60 |
| acatatacta tagctagttt ccatattaac ttaaaatagt actccaagcc aacccagaaa | 120 |
| gaaaaaaat actactagtt gtatcaatct tctcaaggaa ctagaagtat aacctatact | 180 |
| aagtagactc tatctataca ctaaagcaca aaatctcttc ttttctatac tataaaaaaa | 240 |
| agaagtatat atactagaaa gtgtgcttta aaattttgtt actttaattt tgtctccact | 300 |
| tcttttctcc tatgataggt tgtatcaaat tgggtcctcc gacttgggcc agaaggcctc | 360 |
| acacaatata agagtatccc taacttcctt ttatctttc agctatcaat acgagacttt | 420 |
| ctggtattca tgttcctaga ttacctgtaa caaaatctgg taatagttga gtcggaaatc | 480 |
| gcttattccc actctgaaaa tcaatgtttt catatcccat tctattgtaa tgactcccca | 540 |
| tttcaggcct acttcccaag tcattagaaa ggtaattttg ttggctcact ggcatggcta | 600 |
| ggttttcaga aggaggaagt cctaaagtaa gagagacacc attatttcca tgaaaattcg | 660 |
| cggtgatttg ttgatcatga ggatcaaacc ttccaaaatc tcccatcgcg tatgctgcca | 720 |
| ttaaaggatt agtaaaccct ttatttgatg attctctagc tttggcttcc atgtcaacag | 780 |
| atgaaagaat actacttgga gaaaacttgt gcatgtcatt tctttgcttt ttcgcgttgt | 840 |
| tttcaatatg atcaacagta gtagtagtag tattatccat gttgaatgaa ccaaggaagg | 900 |
| agaaattgtg agcatgatga agtgaagcac ctgcagtagg ggaagttgaa atagttgagg | 960 |
| tagaaatttc tgcttgagta gtagtaatac catcttgtaa taagctgcta gtaataattg | 1020 |
| gatgtttctc ttcatttgga gcctctttgt ttttgttatc tcctgaagta ttagtactgt | 1080 |
| tttgttcttg attcttcact tcttccaagt acatttcttc taccattggc ttccataatc | 1140 |
| gaactcgagc atttatgaac cagtagaga cctgcatttt catatatatt aagaattttt | 1200 |
| ttataaagaa aagaaaggaa ttaatccaag aattatagta aaatgtgtgt ctaagaacct | 1260 |
| ggctccttgt tagcccccgtt tgcttagcaa gcatgatttt gtctgaatcc tttgggtaac | 1320 |
| tgcaatataa aaatatatta agaaaaaaaa aattatagtt aaaaacatac tcctatatta | 1380 |
| gagaagaatg ggcgaattca gaatttagaa taataatgtg atcttattat atacatgaac | 1440 |

```
atattttatt ttttgtgtgt atgcatatat agtttgagtt aaaagtaagt gtcttttta    1500 ccgtccaaac gaaagtttca aataactgg cgttgctcta aaatcactt aatttgttcc     1560 taatggatgg acatgttaaa accatataaa agacacttag taaaatatag gacgacaggc   1620
gtatatatga cgcaaaaatt ggttagaata atcaattttc tatctactac tccgtagata  1680
tttttcacat tgttaaattt ttcaaagaaa taaatagttt aggagtactc acggatgaag  1740
aaaatgctcg aaaagccaag cacgaaggac agagacagct ctttcaggta aacctctttg  1800
gggtctccaa gcatttggtt gcatcattcc tagctgttgc agcgcgcgtt gttgccttag  1860
atgatggtcc acaaatttga gtcttgagcc ttcgattttc cctactaagc cttcctcttc  1920
acctaaactc ttgctcgtcg cctttacttg ctcagcaatt gcatccttta ggcatctgaa  1980
ttgcttcgaa attgcatgca aagctaattg agtgtatgat ttggctgaac caattcctgc  2040
tacttgctca aatgatgata caattatttg catttggtga tggtactgtc tgtacctttg  2100
ctccacctga acaaaaaaaa gggagtaata ttaaactttt accagtctgt cgttttacaa  2160
catgaagtta tcttatgttg gctactattg aaattaaaga attttatttc agttaaaaga  2220
tcatatatat atatatatat atattccaag tgagaaataa attgagtagt atattttgca  2280
aaattttgta aaccaacgaa tttttgagag tcattagatt gaggacacat ctgagtggac  2340
attatgcgtg gtgtaaaaaa ggtgaataag agatagtggt ttgaattttg gtgcagcgga  2400
agacatttca ggttcgtagc taactttggt gtattatctt tatagcttta gttggacccg  2460
cagaagaaaa tttaagagcc acacattgtc agtttgtttt aatatcaacg tacgtgattg  2520
gtctcttgtt cttcaactaa ttaacaaaac ctgtacattt catttaccaa ctactattgt  2580
tgcaaacata tataaatcaa cagtttcatc cattcaattt tttatgagaa aaattacagt  2640
tttgaatcat ttgaaaataa aattttaaat atatatgtcg aattcagtag ttttagtgtt  2700
aagaatccga aattcataga ctcaaaattc aggatcatac ctcttcaagc atggcaagaa  2760
gcttggcttt tttcatttga agttcttgtc tttgagcagt tgtaagctca atagcaactt  2820 cattttctg cctgctgcta ctttcaccac caccaccacc accagaacta ttagtgttga   2880
catcactagc caaaggcatt gaattatcct tcttttgatc atctcctttg atgctttttc  2940
caacaatatt aacaacttca tcaagaagct cttgtgcagc tttcagatac ttagagccta  3000
aaaccatgtt gctagaactt ccatctaatg ttcctctaat agtaacatta tttgtccttg  3060
gtgatgagga tgaaatattg ttattgaaac taatttgctg ttgttgctga ggagaaaggc  3120
ttagagatag accgccttgc tgttgttgct gctgctgtcg gtgttgtggt gtcggaatcg  3180
gcctctgaaa cgccaattga gacgccaagt ccgtggtgat cccgccacat gacgtggcag  3240 aaaccccgt cgacgatggt actatcacct gctgagattt atcttggttg ttccacatac   3300
gctgtaaaag tccatgatga ttgatctgat cgtgcaaact tactgccgga gaggcacac   3360 cgacaaagtc ctgctgttgc agcggcgcgt gttgtatatt cgcatggcaa agcgcgttgc  3420
ttcctgctgg tgaagaattc aggaaaagta actgctgctg ctgctgtgtg tcagaagtag  3480
tgtagccttg catataattg ttagggttca tcaaataaag cgtctgaata ttattattat  3540
tactactatt cccatgatta tgatgttgtt gatgatcagc ttgtatatta ttatccgagg  3600
ttccttgata gtacatatct gcaaaaaaaa atctttcttc ttcgaatttc tccttttatc  3660
tacaacagta cctgtaaaca gaaagtaaca aaggagaaaa ggcttcaaat aagtccacac  3720
aaacattttt ataagtaaac ggaagggaat tctttatagt gaaaaattaa attttgttta  3780
```

```
cagagatctt caactataaa taaaaaaaac aggaaaatga tataaaagaa agagaaagag    3840
atgaaaggag ctttagcaaa aaaatcagtc actcacacat acacacatgt aactaactgt    3900
ctatcttcgg gtggtagctc tctaagcttt gagaagttgc cttcttgtca gactgatcta    3960 tattttctc  tctgcattct catctcttca accacaaaaa ggaaatatga ataaa         4015
```

```
<210> SEQ ID NO 9
<211> LENGTH: 29
<212> TYPE: DNA
<213> ORGANISM: Artificial
<220> FEATURE:
<223> OTHER INFORMATION: Solanum tuberosum L.

<400> SEQUENCE: 9
rmrbcatcta gagtaggggg ggaggcacc                                        29

<210> SEQ ID NO 10
<211> LENGTH: 36
<212> TYPE: DNA
<213> ORGANISM: Artificial
<220> FEATURE:
<223> OTHER INFORMATION: Solanum tuberosum L.

<400> SEQUENCE: 10
rmrbrgagag ctcgaagcac aaaatttaca atatac                                36

<210> SEQ ID NO 11
<211> LENGTH: 33
<212> TYPE: DNA
<213> ORGANISM: Artificial
<220> FEATURE:
<223> OTHER INFORMATION: Solanum tuberosum L.

<400> SEQUENCE: 11
rmrbacatct agattagctc tcatcacttc aca                                   33

<210> SEQ ID NO 12
<211> LENGTH: 32
<212> TYPE: DNA
<213> ORGANISM: Artificial
<220> FEATURE:
<223> OTHER INFORMATION: Solanum tuberosum L.

<400> SEQUENCE: 12
rmrbragagg tacctaccac ccaaaatact ac                                    32

<210> SEQ ID NO 13
<211> LENGTH: 37
<212> TYPE: DNA
<213> ORGANISM: Artificial
<220> FEATURE:
<223> OTHER INFORMATION: Solanum tuberosum L.

<400> SEQUENCE: 13
rmrstbasga gctcgaaatt tatggctatg tactatc                               37

<210> SEQ ID NO 14
<211> LENGTH: 36
<212> TYPE: DNA
<213> ORGANISM: Artificial
<220> FEATURE:
<223> OTHER INFORMATION: Solanum tuberosum L.

<400> SEQUENCE: 14
rmrstbasrt ctagagtgga agacggtata tgtgat                                36
```

<210> SEQ ID NO 15
<211> LENGTH: 37
<212> TYPE: DNA
<213> ORGANISM: Artificial
<220> FEATURE:
<223> OTHER INFORMATION: Solanum tuberosum L.

<400> SEQUENCE: 15
rmrstbasga gctcgtgtta tttgtttatt gtggaga        37

<210> SEQ ID NO 16
<211> LENGTH: 35
<212> TYPE: DNA
<213> ORGANISM: Artificial
<220> FEATURE:
<223> OTHER INFORMATION: Solanum tuberosum L.

<400> SEQUENCE: 16
rmrstbasrt ctagagtctg ctccaactcc gtcta        35

<210> SEQ ID NO 17
<211> LENGTH: 34
<212> TYPE: DNA
<213> ORGANISM: Artificial
<220> FEATURE:
<223> OTHER INFORMATION: Solanum tuberosum L.

<400> SEQUENCE: 17
rmrbtataag cttaactaac taactaactg tccc        34

<210> SEQ ID NO 18
<211> LENGTH: 34
<212> TYPE: DNA
<213> ORGANISM: Artificial
<220> FEATURE:
<223> OTHER INFORMATION: Solanum tuberosum L.

<400> SEQUENCE: 18
rmrbrgagtc tagaactcca caacacataa aggg        34

<210> SEQ ID NO 19
<211> LENGTH: 34
<212> TYPE: DNA
<213> ORGANISM: Artificial
<220> FEATURE:
<223> OTHER INFORMATION: Solanum tuberosum L.

<400> SEQUENCE: 19
rmrbcacaag ctttgagaag aaaaccaaag aaac        34

<210> SEQ ID NO 20
<211> LENGTH: 35
<212> TYPE: DNA
<213> ORGANISM: Artificial
<220> FEATURE:
<223> OTHER INFORMATION: Solanum tuberosum L.

<400> SEQUENCE: 20
rmrbraacgg atccagatgt ggatgtgtga atgtg        35

<210> SEQ ID NO 21
<211> LENGTH: 48
<212> TYPE: DNA
<213> ORGANISM: Artificial
<220> FEATURE:

```
<223> OTHER INFORMATION: Solanum tuberosum L.

<400> SEQUENCE: 21
rmrgasbtat attatatccc gggtttaaga aaatctctca ctttctct            48

<210> SEQ ID NO 22
<211> LENGTH: 49
<212> TYPE: DNA
<213> ORGANISM: Artificial
<220> FEATURE:
<223> OTHER INFORMATION: Solanum tuberosum L.

<400> SEQUENCE: 22
rmrgasbrta tattatatga gctcgtttac atatatgcaa attgaaaca            49

<210> SEQ ID NO 23
<211> LENGTH: 48
<212> TYPE: DNA
<213> ORGANISM: Artificial
<220> FEATURE:
<223> OTHER INFORMATION: Solanum tuberosum L.

<400> SEQUENCE: 23
rmrgasbtat attatatccc gggttctttc tttctttctc ctctctct            48

<210> SEQ ID NO 24
<211> LENGTH: 49
<212> TYPE: DNA
<213> ORGANISM: Artificial
<220> FEATURE:
<223> OTHER INFORMATION: Solanum tuberosum L.

<400> SEQUENCE: 24
rmrgasbrta tattatatga tatcggctaa aatggatgga gtattattt            49

<210> SEQ ID NO 25
<211> LENGTH: 25
<212> TYPE: DNA
<213> ORGANISM: Artificial
<220> FEATURE:
<223> OTHER INFORMATION: Solanum tuberosum L.

<400> SEQUENCE: 25
rmraggacac tagcaaaact ttagg            25

<210> SEQ ID NO 26
<211> LENGTH: 25
<212> TYPE: DNA
<213> ORGANISM: Artificial
<220> FEATURE:
<223> OTHER INFORMATION: Solanum tuberosum L.

<400> SEQUENCE: 26
rmrrctttga ggcttccatg cattg            25

<210> SEQ ID NO 27
<211> LENGTH: 23
<212> TYPE: DNA
<213> ORGANISM: Artificial
<220> FEATURE:
<223> OTHER INFORMATION: Solanum tuberosum L.

<400> SEQUENCE: 27
rmrcatttgc ctcaacacaa ccc            23
```

-continued

```
<210> SEQ ID NO 28
<211> LENGTH: 25
<212> TYPE: DNA
<213> ORGANISM: Artificial
<220> FEATURE:
<223> OTHER INFORMATION: Solanum tuberosum L.

<400> SEQUENCE: 28
rmrrtgatgc tttcgatctc tggtg                                         25

<210> SEQ ID NO 29
<211> LENGTH: 26
<212> TYPE: DNA
<213> ORGANISM: Artificial
<220> FEATURE:
<223> OTHER INFORMATION: Solanum tuberosum L.

<400> SEQUENCE: 29
rmrgadhgaa ggactggaga ggtgga                                        26

<210> SEQ ID NO 30
<211> LENGTH: 29
<212> TYPE: DNA
<213> ORGANISM: Artificial
<220> FEATURE:
<223> OTHER INFORMATION: Solanum tuberosum L.

<400> SEQUENCE: 30
rmrgadhrga caacagaaac atcagcagt                                     29

<210> SEQ ID NO 31
<211> LENGTH: 27
<212> TYPE: DNA
<213> ORGANISM: Artificial
<220> FEATURE:
<223> OTHER INFORMATION: Solanum tuberosum L.
<220> FEATURE:
<221> NAME/KEY: misc_feature
<222> LOCATION: (4)..(4)
<223> OTHER INFORMATION: n is a, c, g, or t

<400> SEQUENCE: 31
rmrntgcggg actctaatca taaaaac                                       27

<210> SEQ ID NO 32
<211> LENGTH: 28
<212> TYPE: DNA
<213> ORGANISM: Artificial
<220> FEATURE:
<223> OTHER INFORMATION: Solanum tuberosum L.

<400> SEQUENCE: 32
rmrgsgstgg aaacggcaga gaaggtac                                      28

<210> SEQ ID NO 33
<211> LENGTH: 28
<212> TYPE: DNA
<213> ORGANISM: Artificial
<220> FEATURE:
<223> OTHER INFORMATION: Solanum tuberosum L.

<400> SEQUENCE: 33
rmrgsattag tgacggacaa cttctgtc                                      28

<210> SEQ ID NO 34
<211> LENGTH: 31
<212> TYPE: DNA
```

```
<213> ORGANISM: Artificial
<220> FEATURE:
<223> OTHER INFORMATION: Solanum tuberosum L.

<400> SEQUENCE: 34
rmrgsgtaaa tcagcttgaa attacatcat g                              31

<210> SEQ ID NO 35
<211> LENGTH: 36
<212> TYPE: DNA
<213> ORGANISM: Artificial
<220> FEATURE:
<223> OTHER INFORMATION: Solanum tuberosum L.

<400> SEQUENCE: 35
rmrstbasrt ctagagtgga agacggtata tgtgat                         36

<210> SEQ ID NO 36
<211> LENGTH: 30
<212> TYPE: DNA
<213> ORGANISM: Artificial
<220> FEATURE:
<223> OTHER INFORMATION: Solanum tuberosum L.

<400> SEQUENCE: 36
rmrstbasrc agaaaatcca acatatccag                                30

<210> SEQ ID NO 37
<211> LENGTH: 31
<212> TYPE: DNA
<213> ORGANISM: Artificial
<220> FEATURE:
<223> OTHER INFORMATION: Solanum tuberosum L.
<220> FEATURE:
<221> NAME/KEY: misc_feature
<222> LOCATION: (4)..(4)
<223> OTHER INFORMATION: n is a, c, g, or t

<400> SEQUENCE: 37
rmrnstrscr gcaacaggat tcaatcttaa g                              31

<210> SEQ ID NO 38
<211> LENGTH: 25
<212> TYPE: DNA
<213> ORGANISM: Artificial
<220> FEATURE:
<223> OTHER INFORMATION: Solanum tuberosum L.
<220> FEATURE:
<221> NAME/KEY: misc_feature
<222> LOCATION: (6)..(6)
<223> OTHER INFORMATION: n is a, c, g, or t

<400> SEQUENCE: 38
rmrkanrgga ttgcacgcag gttct                                     25

<210> SEQ ID NO 39
<211> LENGTH: 27
<212> TYPE: DNA
<213> ORGANISM: Artificial
<220> FEATURE:
<223> OTHER INFORMATION: Solanum tuberosum L.
<220> FEATURE:
<221> NAME/KEY: misc_feature
<222> LOCATION: (6)..(6)
<223> OTHER INFORMATION: n is a, c, g, or t

<400> SEQUENCE: 39
rmrkanrrcg tcaagaaggc gatagaa                                   27
```

<210> SEQ ID NO 40
<211> LENGTH: 35
<212> TYPE: DNA
<213> ORGANISM: Artificial
<220> FEATURE:
<223> OTHER INFORMATION: Solanum tuberosum L.

<400> SEQUENCE: 40
rmrbmrtgsc tatatatgca aactatagta tgttg         35

<210> SEQ ID NO 41
<211> LENGTH: 36
<212> TYPE: DNA
<213> ORGANISM: Artificial
<220> FEATURE:
<223> OTHER INFORMATION: Solanum tuberosum L.

<400> SEQUENCE: 41
rmrbmrtgsc ttctagaaga tatatatatg gttgag         36

<210> SEQ ID NO 42
<211> LENGTH: 39
<212> TYPE: DNA
<213> ORGANISM: Artificial
<220> FEATURE:
<223> OTHER INFORMATION: Solanum tuberosum L.
<220> FEATURE:
<221> NAME/KEY: misc_feature
<222> LOCATION: (4)..(4)
<223> OTHER INFORMATION: n is a, c, g, or t

<400> SEQUENCE: 42
rmrntrvctr sccgcaacag gattcaatct taagaaact         39

<210> SEQ ID NO 43
<211> LENGTH: 30
<212> TYPE: DNA
<213> ORGANISM: Artificial
<220> FEATURE:
<223> OTHER INFORMATION: Solanum tuberosum L.

<400> SEQUENCE: 43
rmrstactrt ggaaaagctt gcctatgtgg         30

<210> SEQ ID NO 44
<211> LENGTH: 30
<212> TYPE: DNA
<213> ORGANISM: Artificial
<220> FEATURE:
<223> OTHER INFORMATION: Solanum tuberosum L.

<400> SEQUENCE: 44
rmrstactrt rctgctcctg gcagtttcaa         30

<210> SEQ ID NO 45
<211> LENGTH: 28
<212> TYPE: DNA
<213> ORGANISM: Artificial
<220> FEATURE:
<223> OTHER INFORMATION: Solanum tuberosum L.
<220> FEATURE:
<221> NAME/KEY: misc_feature
<222> LOCATION: (6)..(6)
<223> OTHER INFORMATION: n is a, c, g, or t

<400> SEQUENCE: 45
rmrstnrttc atctaaaggg ccaacacc                                              28

<210> SEQ ID NO 46
<211> LENGTH: 29
<212> TYPE: DNA
<213> ORGANISM: Artificial
<220> FEATURE:
<223> OTHER INFORMATION: Solanum tuberosum L.
<220> FEATURE:
<221> NAME/KEY: misc_feature
<222> LOCATION: (6)..(6)
<223> OTHER INFORMATION: n is a, c, g, or t

<400> SEQUENCE: 46
rmrstnrtrg ttgtatagct ccccgctca                                             29

<210> SEQ ID NO 47
<211> LENGTH: 34
<212> TYPE: DNA
<213> ORGANISM: Artificial
<220> FEATURE:
<223> OTHER INFORMATION: Solanum tuberosum L.

<400> SEQUENCE: 47
rmrstgartt tctctacaat gagttcacat ggtc                                       34

<210> SEQ ID NO 48
<211> LENGTH: 33
<212> TYPE: DNA
<213> ORGANISM: Artificial
<220> FEATURE:
<223> OTHER INFORMATION: Solanum tuberosum L.

<400> SEQUENCE: 48
rmrstgartr gggacaacct attatcacca agc                                        33

<210> SEQ ID NO 49
<211> LENGTH: 32
<212> TYPE: DNA
<213> ORGANISM: Artificial
<220> FEATURE:
<223> OTHER INFORMATION: Solanum tuberosum L.

<400> SEQUENCE: 49
rmrstaartc tgatcttcga tcaatttcat gg                                         32

<210> SEQ ID NO 50
<211> LENGTH: 32
<212> TYPE: DNA
<213> ORGANISM: Artificial
<220> FEATURE:
<223> OTHER INFORMATION: Solanum tuberosum L.

<400> SEQUENCE: 50
rmrstaartr gacctattgc tgccttgtgc ta                                         32

<210> SEQ ID NO 51
<211> LENGTH: 700
<212> TYPE: PRT
<213> ORGANISM: Artificial
<220> FEATURE:
<223> OTHER INFORMATION: Solanum tuberosum L.

<400> SEQUENCE: 51

Ser Leu Ala Asn Met Thr Asx Glu Arg Ser Met Leu Met Tyr Tyr Gln
1               5                   10                  15

-continued

```
Gly Thr Ser Asp Asn Thr Asn Ile Gln Ala Asp His Gln Gln Arg His
             20                  25                  30

Asn His Gly Asn Ser Asn Asn Asn Ile Gln Thr Leu Tyr Leu Met
         35                  40                  45

Asn Pro Asn Asn Tyr Met Gln Gly Tyr Thr Thr Ser Asp Thr Gln Gln
 50                  55                  60

Gln Gln Gln Leu Leu Phe Leu Asn Ser Ser Pro Ala Ala Ser Asn Ala
 65                  70                  75                  80

Leu Cys His Ala Asn Ile Gln His Ala Pro Leu Gln Gln Gln His Phe
                 85                  90                  95

Val Gly Val Pro Leu Pro Ala Val Ser Leu His Asp Gln Ile Asn His
             100                 105                 110

His Gly Leu Leu Gln Arg Met Trp Asn Asn Gln Asp Gln Ser Gln Gln
         115                 120                 125

Val Ile Val Pro Ser Ser Thr Gly Val Ser Ala Thr Ser Cys Gly Gly
     130                 135                 140

Ile Thr Thr Asp Leu Ala Ser Gln Leu Ala Phe Gln Arg Pro Ile Pro
145                 150                 155                 160

Thr Pro Gln His Arg Gln Gln Gln Gln Gln Gly Gly Leu Ser Leu
                 165                 170                 175

Ser Leu Ser Pro Gln Leu Gln Gln Gln Ile Ser Phe Asn Asn Asn Ile
             180                 185                 190

Ser Ser Ser Ser Pro Arg Thr Asn Asn Val Thr Ile Arg Gly Thr Leu
         195                 200                 205

Asp Gly Ser Ser Ser Asn Met Val Leu Gly Ser Lys Tyr Leu Lys Ala
 210                 215                 220

Ala Gln Glu Leu Leu Asp Glu Val Val Asn Ile Val Gly Lys Ser Ile
225                 230                 235                 240

Lys Gly Asp Asp Gln Lys Lys Asp Asn Ser Met Asn Lys Glu Ser Met
                 245                 250                 255

Pro Leu Ala Ser Asp Val Asn Thr Asn Ser Ser Gly Gly Gly Glu Ser
             260                 265                 270

Ser Ser Arg Gln Lys Asn Glu Val Ala Val Glu Leu Thr Thr Ala Gln
         275                 280                 285

Arg Gln Glu Leu Gln Met Lys Lys Ala Lys Leu Leu Ala Met Leu Glu
 290                 295                 300

Glu Val Glu Gln Arg Tyr Arg Gln Tyr His His Gln Met Gln Ile Ile
305                 310                 315                 320

Val Leu Ser Phe Glu Gln Val Ala Gly Ile Gly Ser Ala Lys Ser Tyr
                 325                 330                 335

Thr Gln Leu Ala Leu His Ala Ile Ser Lys Gln Phe Arg Cys Leu Lys
             340                 345                 350

Asp Ala Ile Ala Glu Gln Val Lys Ala Thr Ser Lys Ser Leu Gly Glu
         355                 360                 365

Glu Glu Gly Leu Gly Gly Lys Ile Glu Gly Ser Arg Leu Lys Phe Val
 370                 375                 380

Asp His His Leu Arg Gln Gln Arg Ala Leu Gln Gln Ile Gly Met Met
385                 390                 395                 400

Gln Pro Asn Ala Trp Arg Pro Gln Arg Gly Leu Pro Glu Arg Ala Val
                 405                 410                 415

Ser Val Leu Arg Ala Trp Leu Phe Glu His Phe Leu His Pro Tyr Pro
             420                 425                 430

Lys Asp Ser Asp Lys Ile Met Leu Ala Lys Gln Thr Gly Leu Thr Arg
```

```
                    435                 440                 445
Ser Gln Val Ser Asn Trp Phe Ile Asn Ala Arg Val Arg Leu Trp Lys
450                 455                 460
Pro Met Val Glu Glu Met Tyr Leu Glu Glu Val Lys Asn Gln Glu Gln
465                 470                 475                 480
Asn Ser Thr Asn Thr Ser Gly Asp Asn Lys Asn Lys Glu Thr Asn Ile
                485                 490                 495
Ser Ala Pro Asn Glu Glu Lys His Pro Ile Ile Thr Ser Ser Leu Leu
                500                 505                 510
Gln Asp Gly Ile Thr Thr Thr Gln Ala Glu Ile Ser Thr Ser Thr Ile
                515                 520                 525
Ser Thr Ser Pro Thr Ala Gly Ala Ser Leu His His Ala His Asn Phe
                530                 535                 540
Ser Phe Leu Gly Ser Phe Asn Met Asp Asn Thr Thr Thr Val Asp
545                 550                 555                 560
His Ile Glu Asn Asn Ala Lys Lys Gln Arg Asn Asp Met His Lys Gly
                565                 570                 575
Ser Pro Ser Ser Ile Leu Ser Ser Val Asp Met Glu Ala Lys Ala Arg
                580                 585                 590
Glu Ser Ser Asn Lys Gly Phe Thr Asn Pro Leu Met Ala Ala Tyr Ala
                595                 600                 605
Met Gly Asp Phe Gly Arg Phe Asp Pro His Asp Gln Gln Met Thr Ala
            610                 615                 620
Asn Phe His Gly Asn Asn Gly Val Ser Leu Thr Leu Gly Leu Pro Pro
625                 630                 635                 640
Ser Glu Asn Leu Ala Met Pro Val Ser Gln Gln Asn Tyr Leu Ser Asn
                645                 650                 655
Asp Leu Gly Ser Arg Ser Glu Met Gly Ser His Tyr Asn Arg Met Gly
                660                 665                 670
Tyr Glu Asn Ile Asp Phe Gln Ser Gly Asn Lys Arg Phe Pro Thr Gln
                675                 680                 685
Leu Leu Pro Asp Phe Val Thr Gly Asn Leu Gly Thr
                690                 695                 700

<210> SEQ ID NO 52
<211> LENGTH: 721
<212> TYPE: PRT
<213> ORGANISM: Artificial
<220> FEATURE:
<223> OTHER INFORMATION: Solanum tuberosum L.

<400> SEQUENCE: 52

Ser Leu Ala Asn Met Thr Asx Glu Arg Ser Met Leu Met Ala Met Tyr
1               5                   10                  15
Tyr Gln Gly Gly Ser Glu Ile Gln Ala Asp Gly Leu Gln Thr Leu Tyr
                20                  25                  30
Leu Met Asn Pro Asn Tyr Ile Gly Tyr Thr Asp Thr His His His
            35                  40                  45
His Gln His Gln Gln Ser Ala Asn Met Phe Phe Leu Asn Ser Val
    50                  55                  60
Ala Ala Gly Asn Phe Pro His Val Ser Leu Pro Leu Gln Ala His Ala
65                  70                  75                  80
Gln Gly His Leu Val Gly Val Pro Leu Pro Ala Gly Phe Gln Asp Pro
                85                  90                  95
Asn Arg Pro Ser Ile Gln Glu Ile Pro Thr Ser His His Gly Leu Ile
```

-continued

```
                100                 105                 110
Ser Arg Leu Trp Thr Ser Gly Asp Gln Asn Thr Pro Arg Gly Gly Gly
            115                 120                 125

Gly Gly Gly Glu Gly Asn Gly Ser Gln Ser His Ile Pro Ser Ser Thr
            130                 135                 140

Val Val Ser Pro Asn Ser Gly Ser Gly Gly Thr Thr Thr Asp Phe
145                 150                 155                 160

Ala Ser Gln Leu Gly Phe Gln Arg Pro Gly Leu Val Ser Pro Thr Gln
            165                 170                 175

Ala His His Gln Gly Leu Ser Leu Ser Leu Ser Pro Gln Gln Gln Met
            180                 185                 190

Asn Phe Arg Ser Ser Leu Pro Leu Asp His Arg Asp Ile Ser Thr Thr
            195                 200                 205

Asn His Gln Val Gly Ile Leu Ser Ser Ser Pro Leu Pro Ser Pro Gly
            210                 215                 220

Thr Asn Thr Asn His Thr Arg Gly Leu Gly Ala Ser Ser Ser Phe Ser
225                 230                 235                 240

Ile Ser Asn Gly Met Ile Leu Gly Ser Lys Tyr Leu Lys Val Ala Gln
                245                 250                 255

Asp Leu Leu Asp Glu Val Val Asn Val Gly Lys Asn Ile Lys Leu Ser
            260                 265                 270

Glu Val Gly Ala Lys Glu Lys His Lys Leu Asp Asn Glu Leu Ile Ser
            275                 280                 285

Leu Ala Ser Asp Asp Val Glu Ser Ser Gln Lys Asn Ser Gly Val
290                 295                 300

Glu Leu Thr Thr Ala Gln Arg Gln Glu Leu Gln Met Lys Lys Ala Lys
305                 310                 315                 320

Leu Val Ser Met Leu Asp Glu Val Asp Gln Arg Tyr Arg Gln Tyr His
                325                 330                 335

His Gln Met Gln Met Ile Ala Thr Ser Phe Glu Gln Thr Thr Gly Ile
            340                 345                 350

Gly Ser Ser Lys Ser Tyr Thr Gln Leu Ala Leu His Thr Ile Ser Lys
            355                 360                 365

Gln Phe Arg Cys Leu Lys Asp Ala Ile Ser Gly Gln Ile Lys Asp Thr
            370                 375                 380

Ser Lys Thr Leu Gly Glu Glu Asn Ile Gly Gly Lys Ile Glu Gly
385                 390                 395                 400

Ser Lys Leu Lys Phe Val Asp His His Leu Arg Gln Gln Arg Ala Leu
                405                 410                 415

Gln Gln Leu Gly Met Met Gln Thr Asn Ala Trp Arg Pro Gln Arg Gly
            420                 425                 430

Leu Pro Glu Arg Ala Val Ser Val Leu Arg Ala Trp Leu Phe Glu His
            435                 440                 445

Phe Leu His Pro Tyr Pro Lys Asp Ser Asp Lys Ile Met Leu Ala Lys
450                 455                 460

Gln Thr Gly Leu Thr Arg Ser Gln Val Ser Asn Trp Phe Ile Asn Ala
465                 470                 475                 480

Arg Val Arg Leu Trp Lys Pro Met Val Glu Glu Met Tyr Met Glu Glu
                485                 490                 495

Val Lys Lys Asn Asn Gln Glu Gln Asn Ile Glu Pro Asn Asn Asn Glu
            500                 505                 510

Ile Val Gly Ser Lys Ser Ser Val Pro Gln Glu Lys Leu Pro Ile Ser
            515                 520                 525
```

-continued

Ser Asn Ile Ile His Asn Ala Ser Pro Asn Asp Ile Ser Thr Ser Thr
        530                 535                 540

Ile Ser Thr Ser Pro Thr Gly Gly Gly Gly Ser Ile Pro Ala Gln Thr
545                 550                 555                 560

Val Ala Gly Phe Ser Phe Ile Arg Ser Leu Asn Met Glu Asn Ile Asp
                565                 570                 575

Asp Gln Arg Asn Asn Lys Lys Ala Arg Asn Glu Met Gln Asn Cys Ser
                580                 585                 590

Thr Ser Thr Ile Leu Ser Met Glu Arg Glu Ile Met Asn Lys Val Val
            595                 600                 605

Gln Asp Glu Thr Ile Lys Ser Glu Lys Phe Asn Asn Thr Gln Thr Arg
            610                 615                 620

Glu Cys Tyr Ser Leu Met Thr Pro Asn Tyr Thr Met Asp Asp Gln Phe
625                 630                 635                 640

Gly Thr Arg Phe Asn Asn Gln Asn His Glu Gln Leu Ala Thr Thr Thr
                645                 650                 655

Thr Thr Phe His Gln Gly Asn Gly His Val Ser Leu Thr Leu Gly Leu
                660                 665                 670

Pro Pro Asn Ser Glu Asn Gln His Asn Tyr Ile Gly Leu Glu Asn His
            675                 680                 685

Tyr Asn Gln Pro Thr His His Pro Asn Ile Ser Tyr Glu Asn Ile Asp
690                 695                 700

Phe Gln Ser Gly Lys Arg Tyr Ala Thr Gln Leu Ile Gln Asp Phe Val
705                 710                 715                 720

Ser

<210> SEQ ID NO 53
<211> LENGTH: 722
<212> TYPE: PRT
<213> ORGANISM: Artificial
<220> FEATURE:
<223> OTHER INFORMATION: Solanum tuberosum L.

<400> SEQUENCE: 53

Ser Leu Ala Asn Met Thr Asx Glu Arg Ser Met Leu Met Ala Ser Tyr
1               5                   10                  15

Phe His Gly Asn Ser Glu Ile His Glu Gly Asn Asp Gly Leu Gln Thr
                20                  25                  30

Leu Ile Leu Met Asn Pro Gly Tyr Val Gly Phe Ser Glu Thr Gln His
            35                  40                  45

His His Ala Pro Pro Pro Pro Pro Gly Gly Ser Ser Asn Ile
        50                  55                  60

Val Phe Phe Asn Ser Asn Pro Ile Gly Asn Ser Met Asn Leu Ser His
65                  70                  75                  80

Ala Pro Pro Pro Pro Pro Gln Gln Gln Phe Ile Gly Ile Pro
                85                  90                  95

Leu Ala Thr Ala Ala Phe Thr Ala Pro Ser Gln Asp Ser Gly Asn Asn
                100                 105                 110

Asn Asn Asn Glu Ser Ile Ser Ala Leu His Gly Phe Leu Ala Arg Ser
            115                 120                 125

Ser Gln Tyr Gly Phe Tyr Asn Pro Ala Asn Asp Leu Thr Ala Ala Arg
        130                 135                 140

Asp Val Thr Arg Ala His His His His Gln Gln Pro Arg Ala Phe Thr
145                 150                 155                 160

-continued

```
Tyr Leu Ser Ser Ser Gln Gln Pro Gly Phe Gly Asn Phe Thr Ala Ala
            165                 170                 175

Arg Glu Leu Val Ser Ser Pro Ser Gly Ser Ala Ser Ala Ser Gly Ile
        180                 185                 190

Gln Gln Gln Gln Gln Gln Gln Ser Ile Ser Ser Val Pro Leu Ser
    195                 200                 205

Ser Lys Tyr Met Lys Ala Ala Gln Glu Leu Leu Asp Glu Val Val Asn
    210                 215                 220

Val Gly Lys Ser Met Lys Ser Thr Asn Ser Thr Asp Val Val Asn
225                 230                 235                 240

Asn Asp Val Lys Lys Ser Lys Asn Met Gly Asp Met Asp Gly Gln Leu
                245                 250                 255

Asp Gly Val Gly Ala Asp Lys Asp Gly Ala Pro Thr Thr Glu Leu Ser
            260                 265                 270

Thr Gly Glu Arg Gln Glu Ile Gln Met Lys Lys Ala Lys Leu Val Asn
        275                 280                 285

Met Leu Asp Glu Val Glu Gln Arg Tyr Arg His Tyr His His Gln Met
    290                 295                 300

Gln Ser Val Ile His Trp Leu Glu Gln Ala Ala Gly Ile Gly Ser Ala
305                 310                 315                 320

Lys Thr Tyr Thr Ala Leu Ala Leu Gln Thr Ile Ser Lys Gln Phe Arg
                325                 330                 335

Cys Leu Lys Asp Ala Ile Ile Gly Gln Ile Arg Ser Ala Ser Gln Thr
            340                 345                 350

Leu Gly Glu Glu Asp Ser Leu Gly Gly Lys Ile Glu Gly Ser Arg Leu
        355                 360                 365

Lys Phe Val Asp Asn Gln Leu Arg Gln Arg Ala Leu Gln Gln Leu
    370                 375                 380

Gly Met Ile Gln His Asn Ala Trp Arg Pro Gln Arg Gly Leu Pro Glu
385                 390                 395                 400

Arg Ala Val Ser Val Leu Arg Ala Trp Leu Phe Glu His Phe Leu His
                405                 410                 415

Pro Tyr Pro Lys Asp Ser Asp Lys Met Met Leu Ala Lys Gln Thr Gly
            420                 425                 430

Leu Thr Arg Ser Gln Val Ser Asn Trp Phe Ile Asn Ala Arg Val Arg
        435                 440                 445

Leu Trp Lys Pro Met Val Glu Glu Met Tyr Leu Glu Glu Ile Lys Glu
    450                 455                 460

His Glu Gln Asn Gly Leu Gly Gln Glu Lys Thr Ser Lys Leu Gly Glu
465                 470                 475                 480

Gln Asn Glu Asp Ser Thr Thr Ser Arg Ser Ile Ala Thr Gln Asp Lys
                485                 490                 495

Ser Pro Gly Ser Asp Ser Gln Asn Lys Ser Phe Val Ser Lys Gln Asp
            500                 505                 510

Asn His Leu Pro Gln His Asn Pro Ala Ser Pro Met Pro Asp Val Gln
        515                 520                 525

Arg His Phe His Thr Pro Ile Gly Met Thr Ile Arg Asn Gln Ser Ala
    530                 535                 540

Gly Phe Asn Leu Ile Gly Ser Pro Glu Ile Glu Ser Ile Asn Ile Thr
545                 550                 555                 560

Gln Gly Ser Pro Lys Lys Pro Arg Asn Asn Glu Met Leu His Ser Pro
                565                 570                 575

Asn Ser Ile Pro Ser Ile Asn Met Asp Val Lys Pro Asn Glu Glu Gln
```

-continued

```
                580                    585                    590
Met Ser Met Lys Phe Gly Asp Asp Arg Gln Asp Arg Asp Gly Phe Ser
        595                    600                605

Leu Met Gly Gly Pro Met Asn Phe Met Gly Gly Phe Gly Ala Tyr Pro
        610            615                620

Ile Gly Glu Ile Ala Arg Phe Ser Thr Glu Gln Phe Ser Ala Pro Tyr
625             630                635                    640

Ser Thr Ser Gly Thr Val Ser Leu Thr Leu Gly Leu Pro His Asn Glu
            645            650                    655

Asn Leu Ser Met Ser Ala Thr His His Ser Phe Leu Pro Ile Pro Thr
            660            665                670

Gln Asn Ile Gln Ile Gly Ser Glu Pro Asn His Glu Phe Gly Ser Leu
        675            680                685

Asn Thr Pro Thr Ser Ala His Ser Thr Ser Ser Val Tyr Glu Thr Phe
        690            695            700

Asn Ile Gln Asn Arg Lys Arg Phe Ala Ala Pro Leu Leu Pro Asp Phe
705             710            715                    720

Val Ala
```

NUCLEIC ACID CONSTRUCTS, PLANTS WITH INCREASED TUBER YIELD, AND METHODS FOR INCREASING TUBER YIELD IN A PLANT

This application claims the benefit of U.S. Provisional Patent Application Ser. No. 62/616,565, filed Jan. 12, 2018, which is hereby incorporated by reference in its entirety.

This invention was made with government support under grant number DBI0820659 awarded by the National Science Foundation. The government has certain rights in the invention.

FIELD OF THE INVENTION

The present invention relates to nucleic acid constructs, transgenic and non-transgenic plants with increased tuber yield, and methods for increasing tuber yield in a plant.

BACKGROUND OF THE INVENTION

There are thirteen functional BEL1-like genes in potato (*Solanum tuberosum* L.) that encode for a family of transcription factors ("TF") ubiquitous in the plant kingdom. These BEL1 TFs work in tandem with KNOTTED1-types to regulate the expression of numerous target genes involved in hormone metabolism and growth processes. One of the StBELs, StBEL5, functions as a long-distance mRNA signal that is transcribed in leaves and moves into roots and stolons to stimulate growth. The two most closely related StBELs to StBEL5 are StBEL11 and StBEL29. Together, these three genes make up more than 70% of all StBEL transcripts present throughout the potato plant. They share a number of common features, suggesting they may be co-functional in tuber development. Upstream sequence driving GUS expression in transgenic potato lines demonstrated that both StBEL11 and StBEL29 promoter activity is robust in leaf veins, petioles, stems, and vascular tissues and induced by short-days in leaves and stolons. Steady-state levels of their mRNAs were also enhanced by short-day conditions in specific organs.

Numerous plant developmental processes are known to be regulated by the three amino acid loop extension ("TALE") family of proteins. The TALE family includes BEL1-like ("BELL") and KNOTTED1-like homeobox ("KNOX") transcription factors (TFs) (Burglin et al., "Analysis of TALE Superclass Homeobox Genes (MEIS, PBC, KNOX, Iroquois, TGIF) Reveals a Novel Domain Conserved Between Plants and Animals," *Nucleic Acids Research* 25:4173-4180 (1997)). Both BELL and KNOX proteins have characteristic proline-tyrosine-proline (P—Y—P) residues between helix I and II of their homeodomain (Passner et al., "Structure of DNA-Bound Ultrabithorax-Extradenticle Homeodomain Complex," *Nature* 397:714-19 (1999)). BELL proteins have a DNA-binding homeodomain, a conserved SKY box, a KNOX protein-interacting BELL domain, and a conserved VSLTLGL motif. Both TALE types are ubiquitous in plants, and during evolution of a number of gene family members have increased in correlation with enhanced complexity. Red and green algal species have only one or two KNOX and BELL genes, whereas land plant genomes contain several genes of both (Mukherjee et al., "A Comprehensive Classification and Evolutionary Analysis of Plant Homeobox Genes," *Mol. Biol. Evol.* 26:2775-94 (2009)).

The BEL1 TF from *Arabidopsis*, the first BEL1 protein discovered, functions in ovule and integument development (Ray et al., "*Arabidopsis* Floral Homeotic Gene BELL (BEL1) Controls Ovule Development Through Negative Regulation of AGAMOUS Gene," *Proc. Nat'l. Acad. Sci. U.S.A.* 97:5761-65 (1994); Reiser et al., "The BELL1 Gene Encodes a Homeodomain Protein Involved in Pattern Formation in the *Arabidopsis* Ovule Primordium," *Cell* 83:735-42 (1995)). BEL1 TFs regulate numerous processes in plants such as development of the shoot apical meristem ("SAM") (Byrne et al., "Phyllotactic Pattern and Stem Cell Fate are Determined by the *Arabidopsis* Homeobox Gene BELL-RINGER," *Development* 130:3941-50 (2003); Rutjens et al., "Shoot Apical Meristem Function in *Arabidopsis* Requires the Combined Activities of Three BEL1-Like Homeodomain Proteins," *Plant J.* 58:641-54 (2009)), control of inflorescence architecture (Bhatt et al., "VAAMANA-a BEL1-Like Homeodomain Protein, Interacts With KNOX Proteins BP and STM and Regulates Inflorescence Stem Growth in *Arabidopsis,*" *Gene* 328:103-11 (2004); Ragni et al., "Interaction of KNAT6 and KNAT2 with BREVIPEDICELLUS and PENNYWISE in *Arabidopsis* Inflorescences," *Plant Cell* 20:888-900 (2008)), leaf patterning (Kumar et al., "The *Arabidopsis* BEL1-LIKE HOMEODOMAIN Proteins SAW1 and SAW2 Act Redundantly to Regulate KNOX Expression Spatially in Leaf Margins," *Plant Cell* 19:2719-35 (2007)), the high-irradiance response of phytochrome A (Staneloni et al., "Bell-Like Homeodomain Selectively Regulates the High-Irradiance Response of Phytochrome A," *Proc. Nat'l. Acad. Sci. U.S.A.* 106:13624-29 (2009)), regulation of tuberization (Chen et al., "Interacting Transcription Factors From the Three Amino Acid Loop Extension Superclass Regulate Tuber Formation," *Plant Physiol.* 132:1391-1404 (2003); Banerjee et al., "Efficient Production of Transgenic Potato (*S. tuberosum* L. ssp. *andigena*) Plants via *Agrobacterium Tumefaciens*-Mediated Transformation," *Plant Sci.* 170:732-38 (2006)) and fruit development (Dong et al., "MDH1: An Apple Homeobox Gene Belonging to the BEL1 Family," *Plant Mol. Biol.* 42:623-33 (2000)).

The BEL1-KNOX tandem complex functions as a transcriptional switch that regulates various developmental pathways in plants (Hay & Tsiantis, "KNOX Genes: Versatile Regulators of Plant Development and Diversity," *Development* 137:3153-65 (2010)). For example, the BELL-RINGER and shoot meristemless (STM) heterodimer in *Arabidopsis* maintains SAM and inflorescence patterning (Byrne et al., "Phyllotactic Pattern and Stem Cell Fate are Determined by the *Arabidopsis* Homeobox Gene BELL-RINGER," *Development* 130:3941-50 (2003); Roeder et al., "The Role of the REPLUMLESS Homeodomain Protein in Patterning the *Arabidopsis* Fruit," *Curr. Biol.* 13:1630-35 (2003)). The BLH1 and KNAT3 heterodimer regulates seed germination and early seedling development in *Arabidopsis* (Kim et al., "BLH1 and KNAT3 Modulate ABA Responses During Germination and Early Seedling Development in *Arabidopsis,*" *Plant J.* 75:755-66 (2013)). In potato, the BEL1-KNOX interaction is functional in regulating the tuberization process and root growth (Chen et al., "Interacting Transcription Factors From the Three Amino Acid Loop Extension Superclass Regulate Tuber Formation," *Plant Physiol.* 132:1391-1404 (2003); Lin et al., "The Impact of the Long-Distance Transport of a BEL1-Like mRNA on Development," *Plant Physiol.* 161:760-72 (2013)). Specifically, the StBEL5-POTH1 heterodimer appears to regulate tuber formation in potato by regulating transcription of target genes that are involved in hormone metabolism. These include genes involved in auxin, cytokinin, and gibberellic acid ("GA") synthesis and activity (Chen et al., "Interacting Transcription Factors From the Three Amino Acid Loop Extension Superclass Regulate Tuber Formation," *Plant Physiol.* 132:1391-1404 (2003); Hannapel et al., "Phloem-Mobile Messenger RNAs and Root Development," *Front. Plant. Sci.* 4:257 (2013); Lin et al., "The Impact of the Long-Distance Transport of a BEL1-Like mRNA on Development," *Plant Physiol.* 161:760-72 (2013)). GA levels are reduced in newly formed tubers, whereas cytokinin and auxin levels are enhanced (Machackova et al., "Photo-Periodic Control of Growth, Development and Phytohormone Balance in *Solanum tuberosum,*" *Physiol. Plant* 102: 272-78 (1998); Xu et al., "The Role of Gibberellin, Abscisic Acid, and Sucrose in the Regulation of Potato Tuber Formation In Vitro," *Plant Physiol.* 117:575-84 (1998); Bou-Torrent et al., "Gibberellin A1 Metabolism Contributes to the Control of Photo-Period-Mediated Tuberization in Potato," *PLoS One* 6:e24458 (2011); Roumeliotis et al., "A Crosstalk of Auxin and GA During Tuber Development," *Plant Signal. Behav.* 7:1360-63 (2012); Abelenda et al., "Flowering and Tuberization: A Tale of Two Nightshades," *Trends Plant Sci.* 19:115-22 (2014)). Included among these target genes are StPIN1, -2, and -4; several AUX/IAA types; StLONELYGUY1, -2, and -3; StGA2 oxidase1; and StGA20 oxidase1 (Chen et al., "Interacting Transcription Factors From the Three Amino Acid Loop Extension Superclass Regulate Tuber Formation," *Plant Physiol.* 132:1391-1404 (2003); Hannapel et al., "Phloem-Mobile Messenger RNAs and Root Development," *Front. Plant. Sci.* 4:257 (2013); Lin et al., "The Impact of the Long-Distance Transport of a BEL1-Like mRNA on Development," *Plant Physiol.* 161:760-72 (2013); Sharma et al., "Targets of the StBEL5 Transcription Factor Include the FT Ortholog StSP6A," *Plant Physiol.* 170:310-24 (2016)). The StBEL5-POTH1 complex binds to tandem TTGAC motifs present in upstream sequence of these target genes. As an example, StGA2ox1, which is strongly induced during early tuber formation (Kloosterman et al., "StGA2ox1 is Induced Prior to Stolon Swelling and Controls GA Levels During Potato Tuber Development," *Plant J.* 52:362-73 (2007)), contains four sets of tandem TTGAC elements in its upstream sequence and two in its first intron (Lin et al., "The Impact of the Long-Distance Transport of a BEL1-Like mRNA on Development," *Plant Physiol.* 161:760-72 (2013)). Each of the two TFs binds to one of the TTGAC core motifs and both are required to affect transcription (Chen et al., "The Tandem Complex of BEL and KNOX Partners is Required for Transcriptional Repression of ga20ox1," *Plant J.* 38:276-84 (2004)).

Both StBEL5 and POTH1 transcripts were detected in phloem cells (Banerjee et al., "Dynamics of a Mobile RNA of Potato Involved in a Long-Distance Signaling Pathway," *Plant Cell* 18:3443-57 (2006); Yu et al., "Tissue Integrity and RNA Quality of Laser Microdissected Phloem of Potato," *Planta* 226:797-803 (2007); Lin et al., "Transcriptional Analysis of Phloem-Associated Cells of Potato," *BMC Genom.* 16:665 (2015)). Both RNAs have been proposed to act as long-distance signals (Banerjee et al., "Dynamics of a Mobile RNA of Potato Involved in a Long-Distance Signaling Pathway," *Plant Cell* 18:3443-57 (2006); Mahajan et al., "The mRNA of a Knotted1-Like Transcription Factor of Potato is Phloem Mobile," *Plant Mol. Biol.* 79:595-608 (2012)) and move freely throughout the plant with enhanced movement of StBEL5 into stolons under short-days (Banerjee et al., "Dynamics of a Mobile RNA of Potato Involved in a Long-Distance Signaling Pathway," *Plant Cell* 18:3443-57 (2006)). Overexpression, movement, and accumulation of StBEL5 RNA have been consistently associated with increased earliness and enhanced tuber yields even under non-inductive long-day conditions (Chen et al., "Interacting Transcription Factors From the Three Amino Acid Loop Extension Superclass Regulate Tuber Formation," *Plant Physiol.* 132:1391-1404 (2003); Banerjee et al., "Untranslated Regions of a Mobile Transcript Mediate RNA Metabolism," *Plant Physiol.* 151:1831-43 (2009)). Movement of its mRNA to stolon tips in over-expressing plants is facilitated by the presence of the untranslated regions of its RNA (Banerjee et al., "Dynamics of a Mobile RNA of Potato Involved in a Long-Distance Signaling Pathway," *Plant Cell* 18:3443-57 (2006); Banerjee et al., "Untranslated Regions of a Mobile Transcript Mediate RNA Metabolism," *Plant Physiol.* 151:1831-43 (2009)). RNA binding proteins that bind to sequences in the 3' untranslated region (UTR) of its transcript facilitate localized StBEL5 movement and enhance tuberization. These RNA-binding proteins are induced by short-day (SD) conditions (Cho et al., "Polypyrimidine Tract-Binding Proteins of Potato Mediate Tuberization Through an Interaction With StBEL5 RNA," *J Expt. Bot.* 66:6835-47 (2015)).

Other tuberization signals like the FT-ortholog StSP6A in potato also accumulate in stolons of plants grown under SD (Navarro et al., "Control of Flowering and Storage Organ Formation in Potato by FLOWERING LOCUS T," *Nature* 478:119-22 (2011); Gonzalez-Schain et al., "Potato CONSTANS is Involved in Photoperiodic Tuberization in a Graft-Transmissible Manner," *Plant J.* 70:678-90 (2012)). The microRNA, miR172, promotes tuber formation and accumulates in stolons at the onset of tuberization (Martin et al., "Graft-Transmissible Induction of Potato Tuberization by the MicroRNA miR172," *Development* 136:2873-81 (2009)). Moreover, Bhogale et al., "MicroRNA156: A Potential Graft-Transmissible MicroRNA That Modulates Plant Architecture and Tuberization in *Solanum tuberosum* ssp. *andigena,*" *Plant Physiol.* 164:1011-27 (2014) suggested that miR156 acts as a phloem-mobile signal and regulates aerial tuber formation in potato.

Recent work on transcription profiling of StBEL5 suggests that it is positioned upstream of the regulatory network that controls the onset of tuber formation (Sharma et al., "Targets of the StBEL5 Transcription Factor Include the FT Ortholog StSP6A," *Plant Physiol.* 170:310-24 (2016)). Signaling targets of StBEL5 include the gene for earliness, StCDF1 (Kloosterman et al., "Naturally Occurring Allele Diversity Allows Potato Cultivation in Northern Latitudes," *Nature* 495:246-50 (2013)), and the tuber signal StSP6A (Navarro et al., "Control of Flowering and Storage Organ Formation in Potato by FLOWERING LOCUS T," *Nature* 478:119-22 (2011)). Through its transcriptional activity in conjunction with its KNOX partner, StBEL5 front-loads the tuber signals, StSP6A and StCDF1, in the leaf and then follows this with a doubling-down of the two key tuber signals, StSP6A and StBEL5, in stolons during the onset of tuber formation. Auto-regulation of its own gene is also occurring in the stolons. Site mutagenesis in tandem TTGAC motifs (specific for the StBEL5/KNOX complex) located in the upstream sequence of both StBEL5 and StSP6A suppressed the SD-induced activity of their promoters in young tubers (Lin et al., "The Impact of the Long-Distance Transport of a BEL1-Like mRNA on Development," *Plant Physiol.* 161:760-72 (2013); Sharma et al., "Targets of the StBEL5 Transcription Factor Include the FT Ortholog StSP6A," *Plant Physiol.* 170:310-24 (2016)). Suppression of StBEL5 activity repressed the accumulation of RNA for StSP6A, whereas induction of StBEL5 had the opposite effect (Sharma et al., "Targets of the StBEL5

Transcription Factor Include the FT Ortholog StSP6A," *Plant Physiol.* 170:310-24 (2016)).

Thirteen BEL1-like genes have been identified in the potato genome and were organized into five clades based on amino-acid sequence (Sharma et al., "The BEL1-Like Family of Transcription Factors in Potato," *J. Expt. Bot.* 65:709-23 (2014)). StBEL5, -11, and -29 are phylogenetically related and exhibit very close sequence matches within their conserved domains. In addition, the transcripts of these three StBEL genes make up more than 70% of the total transcripts in the StBEL family (Xu et al., "Genome Sequence and Analysis of the Tuber Crop Potato," *Nature* 475:189-95 (2011); Sharma et al., "The BEL1-Like Family of Transcription Factors in Potato," *J. Expt. Bot.* 65:709-23 (2014)). All three are present in phloem cells and exhibit very high transcript levels in petioles, a key organ for transporting RNAs into the stem. Similar to StBEL5, these data suggest that StBEL11 and -29 might function as phloem-mobile developmental signals. Although recent results have demonstrated the dramatic effect that suppression of StBEL5 RNA had on tuberization (Sharma et al., "Targets of the StBEL5 Transcription Factor Include the FT Ortholog StSP6A," *Plant Physiol.* 170:310-24 (2016)), it is conceivable that StBEL11 and -29 are also involved in some aspect of tuber formation. Other than StBEL5, very little is known about the functional roles played by other members of the StBEL family.

The present invention is directed to overcoming deficiencies in the art.

SUMMARY OF THE INVENTION

One aspect of the present invention is directed to a nucleic acid construct comprising a first nucleic acid molecule comprising a nucleotide sequence configured to silence or reduce expression of StBEL11 and variants thereof; a 5' DNA promoter sequence; and a 3' terminator sequence, where the first nucleic acid molecule, the promoter sequence, and the terminator sequence are operatively coupled to permit transcription of the first nucleic acid molecule.

Another aspect of the present invention is directed to a nucleic acid construct comprising a first nucleic acid molecule comprising a nucleotide sequence configured to silence or reduce expression of StBEL29 and variants thereof; a 5' DNA promoter sequence; and a 3' terminator sequence, where the first nucleic acid molecule, the promoter sequence, and the terminator sequence are operatively coupled to permit transcription of the first nucleic acid molecule.

A further aspect of the present invention is directed to an expression vector comprising a nucleic acid construct of the present invention.

Another aspect of the present invention is directed to a host cell transformed with a nucleic acid construct of the present invention.

A further aspect of the present invention is directed to a transgenic plant seed transformed with a nucleic acid construct of the present invention.

Another aspect of the present invention is directed to a transgenic plant transformed with a nucleic acid construct of the present invention, where the plant has increased tuber yield compared to a plant not transformed with the nucleic acid construct.

A further aspect of the present invention relates to a transgenic cell of a plant of the present invention.

Another aspect of the present invention relates to a transgenic plant seed produced from a plant of the present invention.

A further aspect of the present invention is directed to a method of increasing tuber yield in a plant. This method involves providing a transgenic plant or plant seed comprising a nucleic acid construct comprising one or more nucleic acid molecules configured to reduce or silence expression of (i) StBEL11 and variants thereof, (ii) StBEL29 and variants thereof, or (iii) both (i) and (ii); and growing the transgenic plant or plant grown from the transgenic plant seed under conditions effective to express the one or more nucleic acid molecules in said transgenic plant or said plant grown from the transgenic plant seed.

Another aspect of the present invention is directed to a potato plant comprising one or more mutations in one or both of StBEL11 and StBEL29, where the potato plant has increased tuber yield compared to the tuber yield of a wild type potato plant.

A further aspect of the present invention relates to potato seed from the potato plant comprising one or more mutations in one or both of StBEL11 and StBEL29 of the present invention.

Using a transgenic approach and heterografting experiments, it is shown herein that both StBEL11 and StBEL29 inhibit growth in correlation with the long distance transport of their mRNAs from leaves to roots and stolons, whereas suppression lines of these two RNAs exhibited enhanced tuber yields. These results indicate that the RNAs of StBEL11 and StBEL29 are phloem-mobile and function antagonistically to the growth-promoting characteristics of StBEL5. Both these RNAs appear to inhibit growth in tubers by repressing the activity of target genes of StBEL5.

As is demonstrated herein, RNAs of StBEL11 and StBEL29 are phloem-mobile and function antagonistically to the growth-promoting characteristics of StBEL5 in potato. Both these RNAs appear to inhibit tuber growth by repressing the activity of target genes of StBEL5 in potato. Moreover, upstream sequence driving GUS expression in transgenic potato lines demonstrated that both StBEL11 and StBEL29 promoter activity is robust in leaf veins, petioles, stems, and vascular tissues and induced by short days in leaves and stolons. Steady-state levels of their mRNAs were also enhanced by short-day conditions in selective organs.

To expand the understanding of long-distance signaling and to determine if they have any relationship with plant growth and tuberization, expression profiles and functional analyses of StBEL11 and StBEL29, which are closely related to StBEL5, were undertaken as part of the present invention. Similar to StBEL5, the results described herein suggest that the RNAs of StBEL11 and StBEL29 function as long-distance signals that regulate growth of tubers in potato.

Figures 11A, 11B, 11C, 11D:
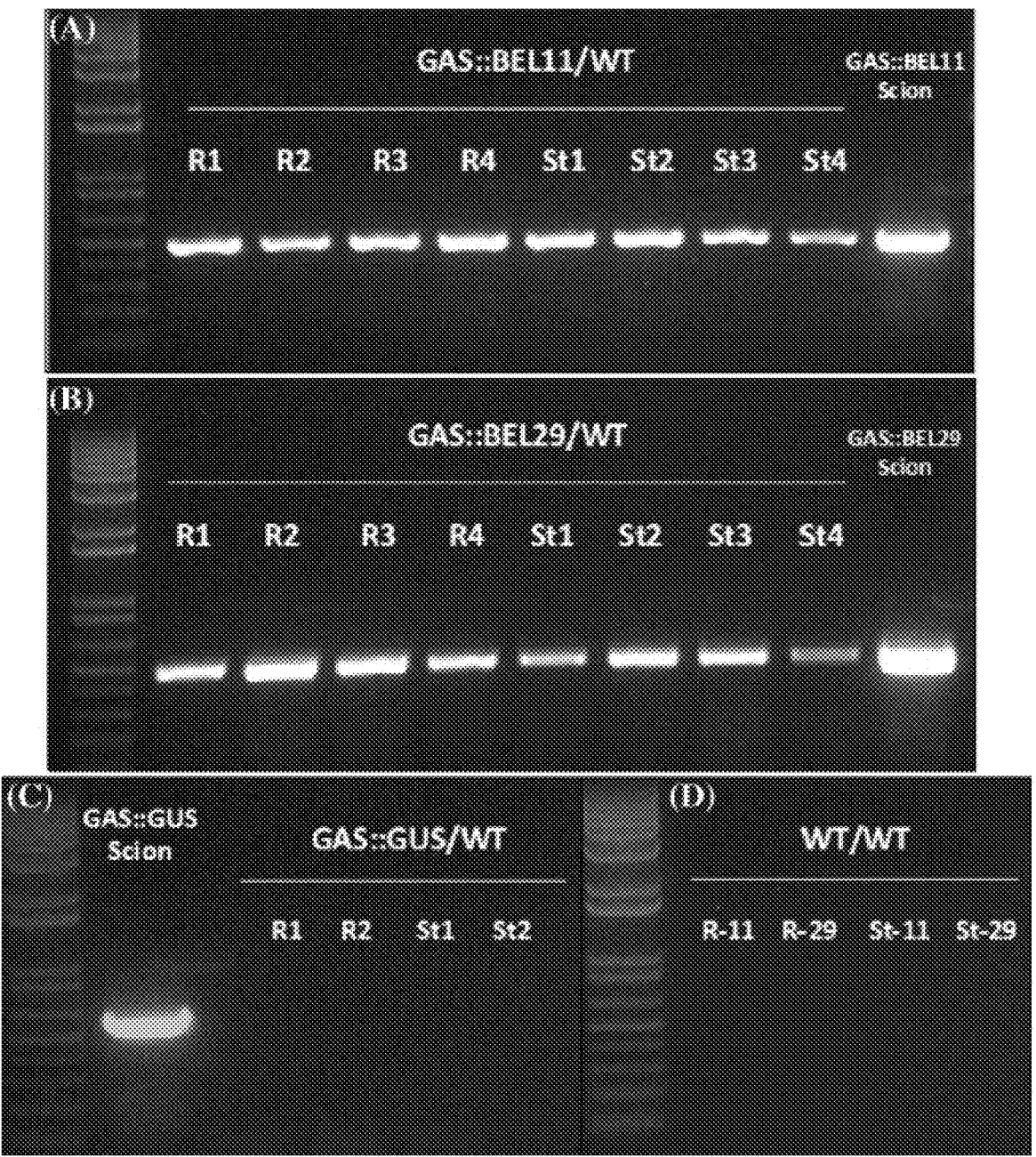
FIGS. 11A-11D show movement of StBEL11 (FIG. 11A) and StBEL29 (FIG. 11B) mRNA across heterografts of soil-grown plants. For heterografts, micrografts were performed with four replicates of GAS:StBEL11 (line 11b), GAS:StBEL29 (line 29-9) and GAS: GUS scions on wild-type andigena stocks. After 2 weeks in culture, grafts were moved to soil and grown under long-days for three weeks and then under short-days for 2 weeks before harvest of leaves, secondary roots, and stolons. Following RNA extraction, gene-specific primers (GSP) were used with a non-plant DNA tag specific for the transgenic RNA (designated NT-2 in the examples herein) to perform one-step RTPCR on 250 ng of total RNA from wild-type secondary roots and stolons of all four heterografts (FIGS. 11A and 11B). RNA from scion leaf samples was used as a positive control (scion samples). All PCR products detected in scion (positive control) and stock (test for movement) RNA samples represent transgenic RNA. GSPs for transgenic StBEL11 (FIG. 11A), transgenic StBEL29 (FIG. 11B), and transgenic GUS (FIG. 11C) were used. Heterografts are designated R1-4

(root stock RNA) and St1-4 (stolon stock RNA). RNA from secondary roots and stolons of wild-type/wildtype (andigena) autografts was used in the RT-PCR with transgenic StBEL11 and -29 gene-specific primers as a negative control (FIG. 11D). Similar negative results were obtained with RNA from wild-type leaves.

Figure 12:
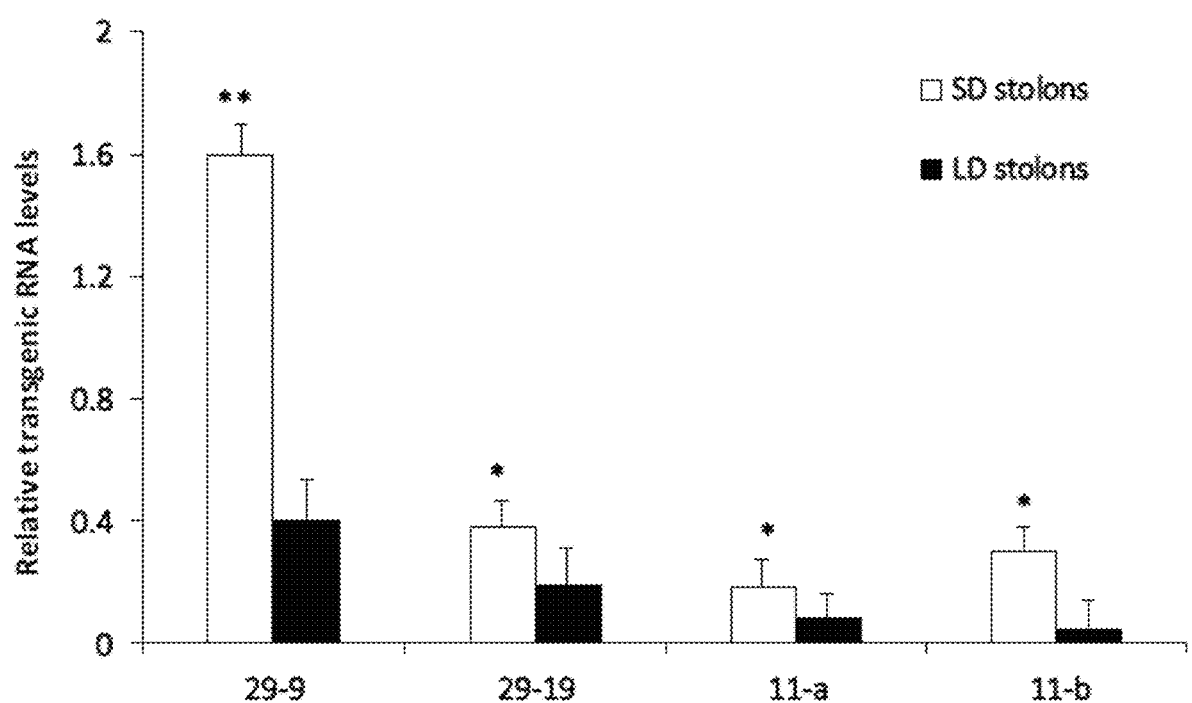

FIG. 12 is a graph showing the photoperiod effect on the movement of transgenic StBEL29 and StBEL11 mRNA into stolons. Movement of transgenic mRNA from leaf to stolon was quantified in transgenic lines expressing full length StBEL11 and -29. Expression was driven by the galactinol synthase (GAS) promoter of melon (Cucumis melo). This promoter is selectively active in the minor veins of leaf mesophyll (Ayre et al., "Functional and Phylogenetic Analyses of A Conserved Regulatory Program in the Phloem of Minor Veins," Plant Physiol. 133:1229-39 (2003) and Banerjee et al., "Untranslated Regions of a Mobile Transcript Mediate RNA Metabolism," Plant Physiol. 151:1831-43 (2009), which are hereby incorporated by reference in their entirety). Relative levels of transgenic RNA were quantified from RNA extracted from 0.5 cm samples from the tip of the stolon. GAS:StBEL11 and -29 plants were grown under long-day conditions for 4 weeks and then transferred to either short-days (SD) for two-weeks or maintained under long-days (LD). RT-qPCR with gene-specific primers was used to measure the relative amounts of transgenic RNA in stolons. Each of the stolon values has been calculated relative to a value of 1.0 for the amount of transgenic RNA measured in either LD or SD leaves from the same plant. Stolons from two plants off four independent plants for each construct were pooled forming two biological replicates. Each biological replicate was measured with two technical replicates and normalized against StActin8 mRNA. The fold change in RNA levels was calculated as the $2^{-\Delta\Delta Ct}$ value. Standard errors of the means of two biological replicates are shown with one, two and three asterisks indicating significant differences ($p<0.05$, $p<0.01$, $p<0.001$, respectively) using a Student's t test.

Figures 13A, 13B:
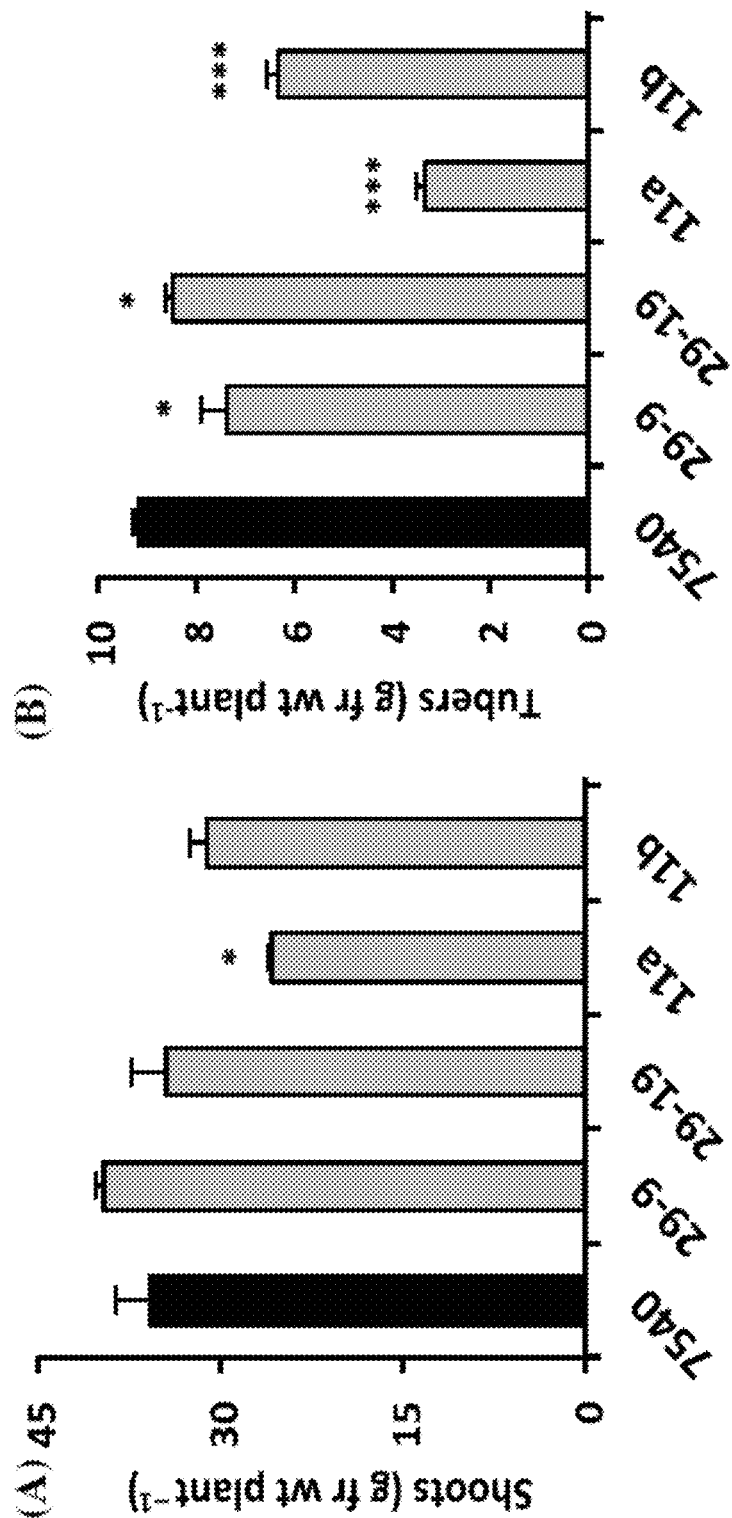

FIGS. 13A-13B show shoot (FIG. 13A) and tuber (FIG. 13B) yields in 7540 (WT) and GAS:StBEL11 and -29 transgenic lines grown under short-day conditions. Data represent the mean of four biological replicates (n=4). One or three asterisks indicate significance ($p<0.05$ and $p<0.001$, respectively) using a Student's t test. Plants were grown under long-days for 4 weeks, followed by 3 weeks under short-day conditions.

Figure 14:
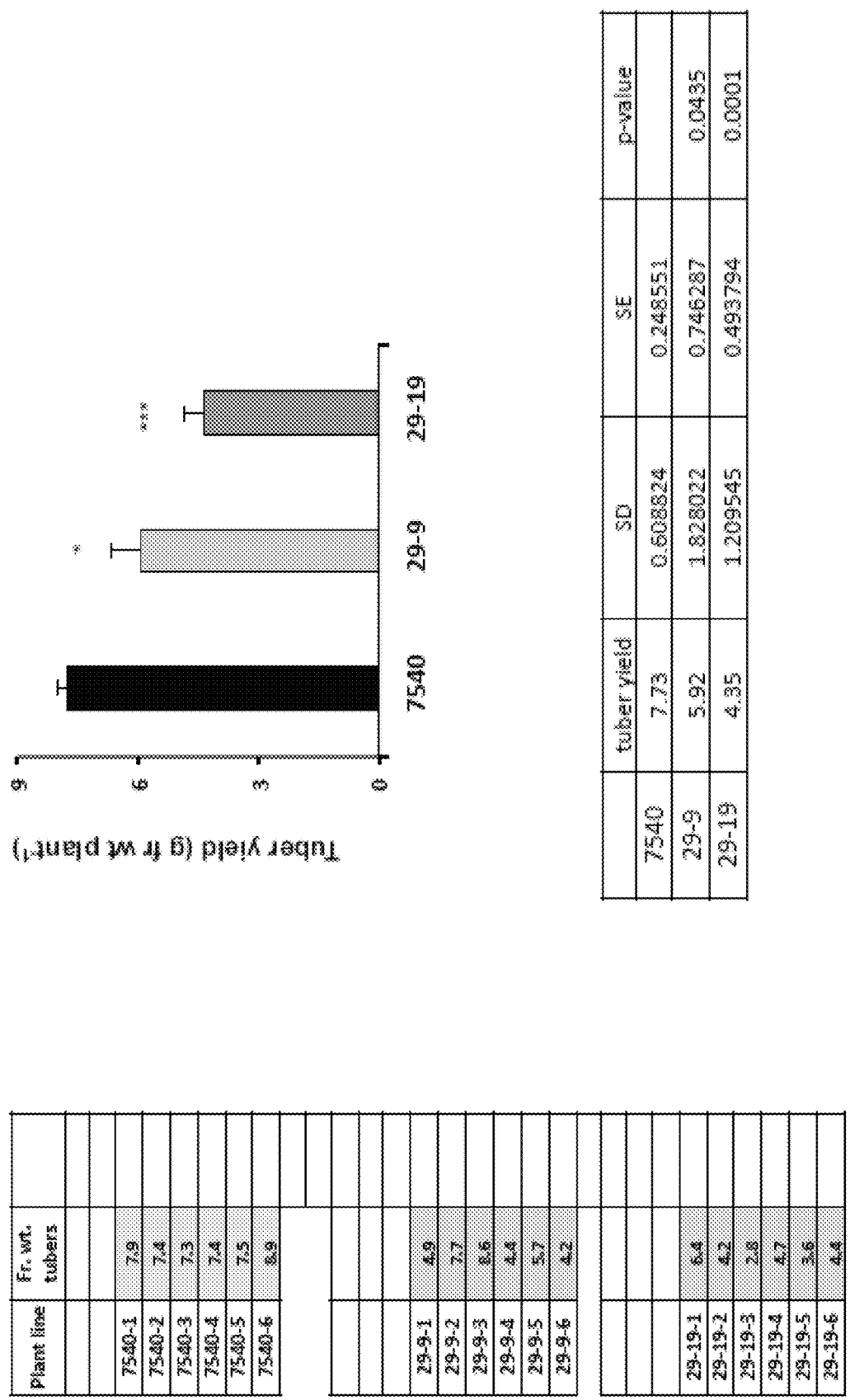

FIG. 14 shows tuber yields of StBEL29 overexpression lines 9 and 19. Both transgenic lines expressed StBEL29 using the leaf-specific GAS promoter. Six replicates per line were assessed for tuber production after 21d short-day conditions. The data represent the mean±SD. Line 7540 is untransformed Solanum tuberosum ssp andigena.

Figures 15A, 15B:
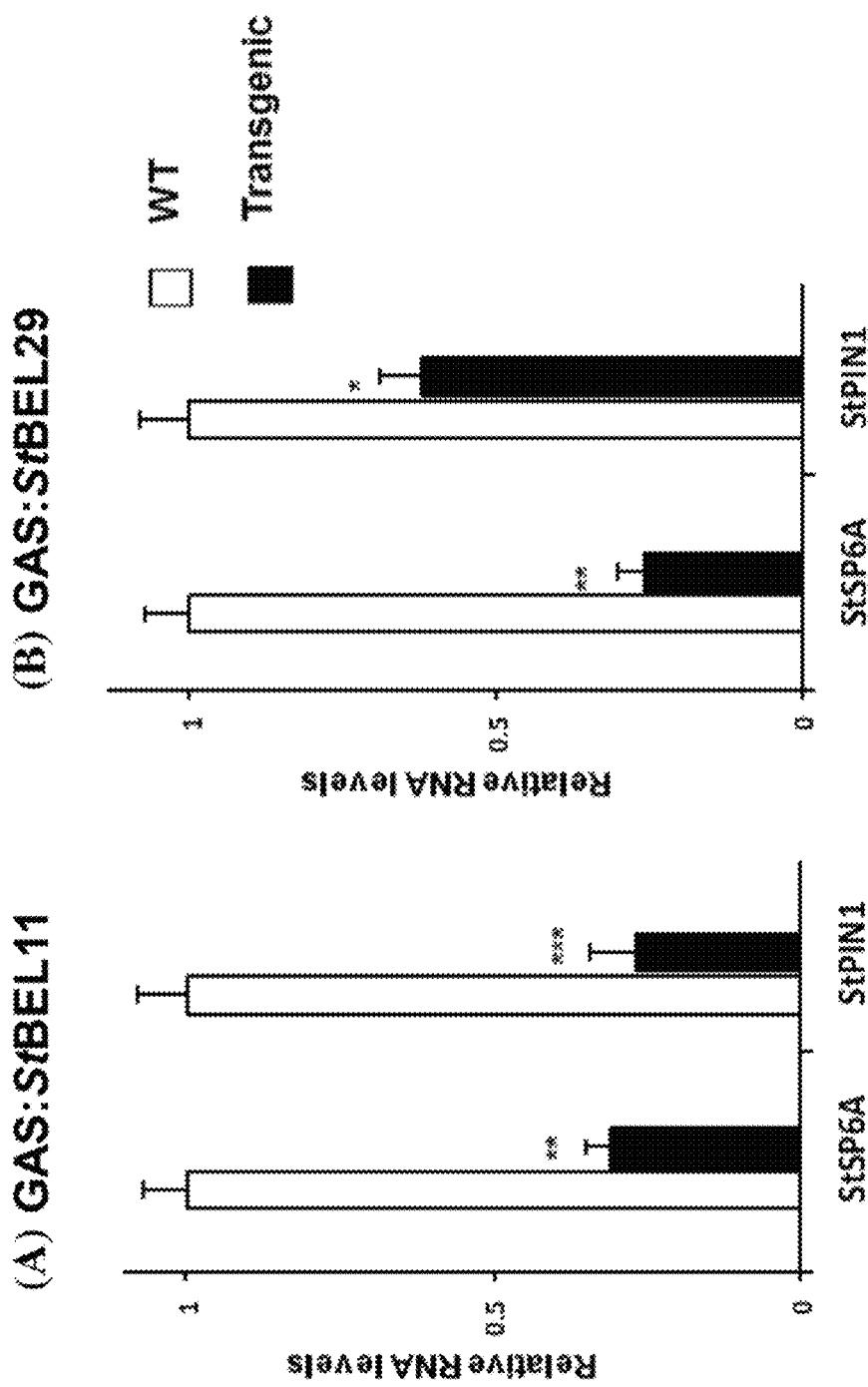

FIGS. 15A-15B show relative levels of StSP6A and StPIN1 RNA in tuberizing stolons of WT 7540 andigena (open bars), or GAS:StBEL11 and -29 transgenic lines (black bars) grown under short-day conditions. Plants were grown under long-days for 4 weeks, followed by 2 weeks under short-day conditions. Stolons from two plants off four independent plants for each construct were pooled forming two biological replicates (n=2). Each biological replicate was quantified using two technical replicates.

Figure 16:
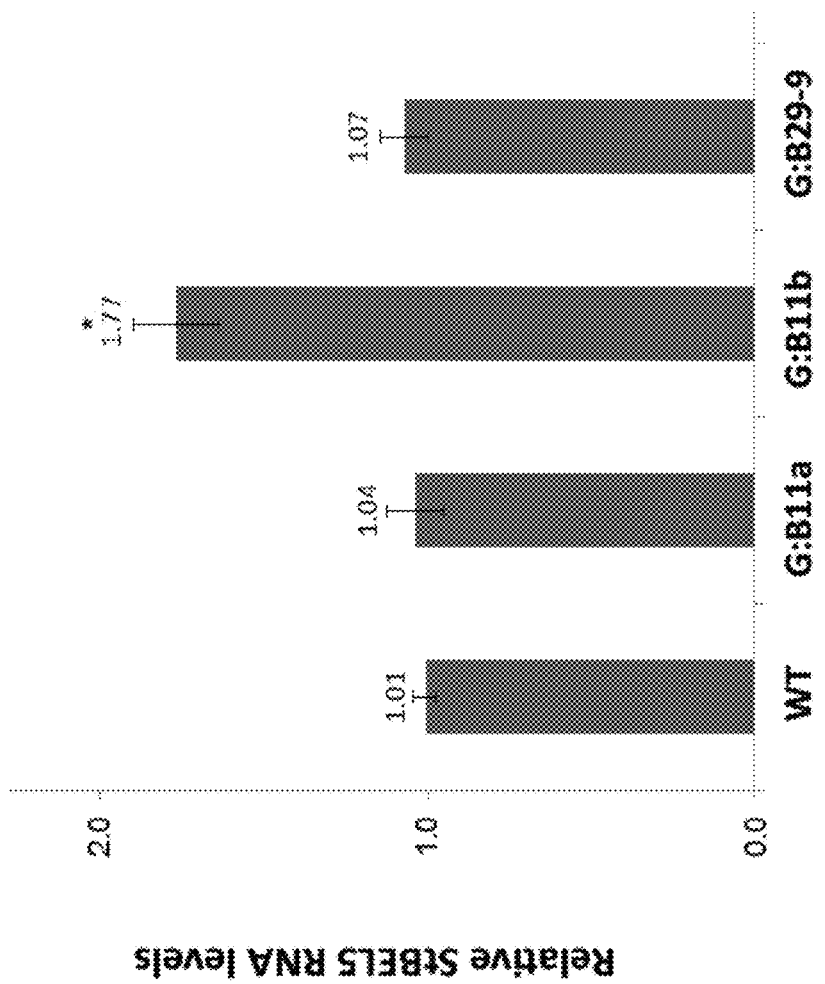
Figures 17A, 17B, 17C, 17D:
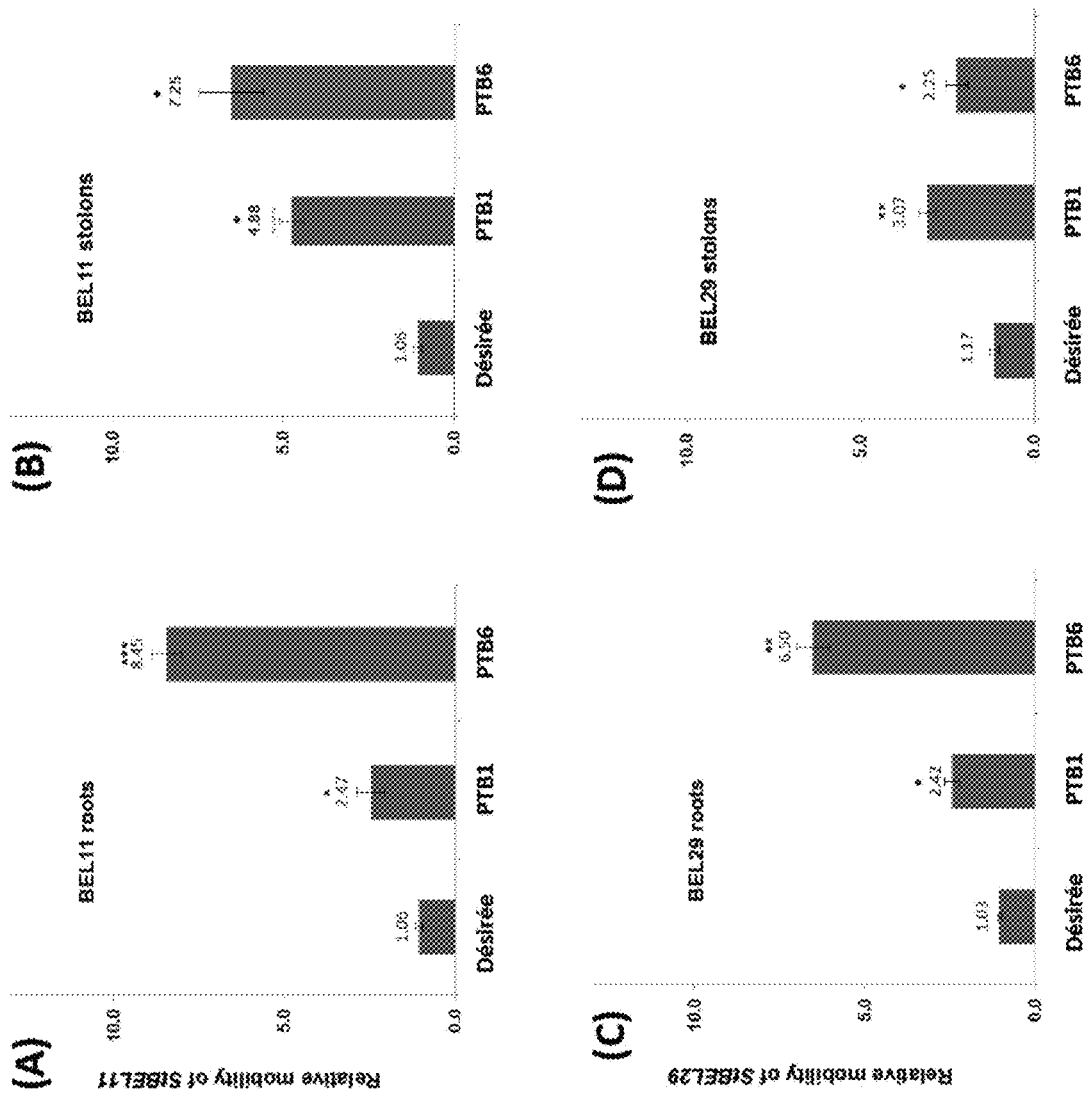

FIG. 16 shows relative levels of StBEL5 RNA in tuberizing stolons of 7540 andigena (WT), GAS:StBEL11 (G:B11), and -29 (G:B29) transgenic lines grown under short-day conditions. Data represent the mean±standard deviation of two biological reps and two technical reps. Plants were grown under long days for four weeks followed by two weeks under short-day conditions.

FIGS. 17A-17D show RNA movement assays for StBEL11 (FIGS. 17A and 17B) and StBEL29 (FIGS. 17C and 17 D) into roots (FIGS. 17A and 17C) and stolons (FIGS. 17B and 17D) using the PVX-based system with over-expression lines of the RNA-binding proteins, StPTB1 and StPTB6, 8 days post-inoculation of leaves. RNA was extracted and RT-qPCR with gene-specific primers was used to calculate the relative amounts of StBEL11 or StBEL29 RNA. Each sample was measured and normalized against StACtin8 RNA. RNA values were calculated as the $2^{-\Delta\Delta Ct}$ value relative to the mean values obtained from WT samples. Standard deviations of the means of two biological replicates with two technical replicates are shown with one, two, and three asterisks indicating significant differences ($p<0.05$, $p<0.01$, $p<0.001$, respectively) using a Student's t-test. This system was used previously to monitor StBEL5 RNA movement (Cho et al., "Polypyrimidine Tract-Binding Proteins of Potato Mediate Tuberization Through an Interaction With StBEL5 RNA," J. Expt. Bot. 66:6835-47 (2015), which is hereby incorporated by reference in its entirety). Movement is facilitated in the StPTB overexpression lines.

Figure 18:
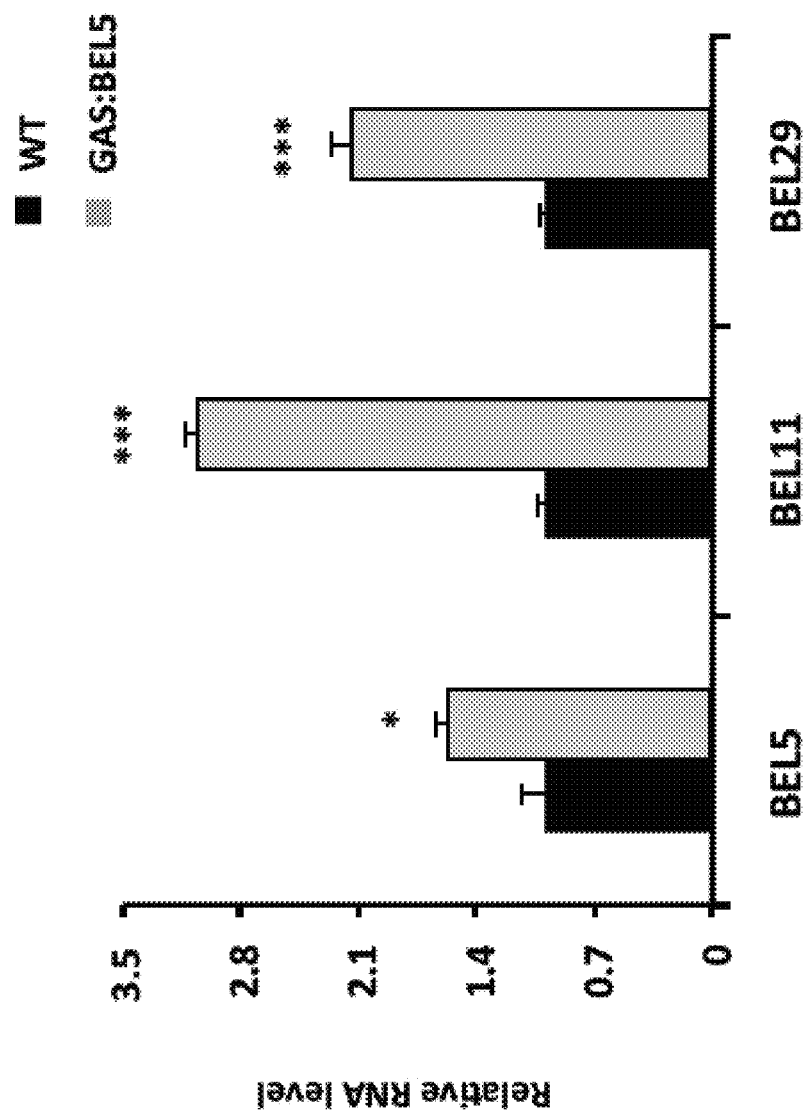

FIG. 18 shows that StBEL5 induces StBEL11 and StBEL29 in stolons from GAS:BEL5 transgenic lines grown under short-day conditions for 12 days. RT-qPCR in replicate was performed on the RNA extracted from the 12 day stolons. StBEL5 RNA levels are included as a control. The GAS promoter is specific to the minor veins of the leaf mesophyll (Ayre et al., "Functional and Phylogenetic Analyses of A Conserved Regulatory Program in the Phloem of Minor Veins," Plant Physiol. 133:1229-39 (2003), which is hereby incorporated by reference in its entirety) and enhanced levels of StBEL5 RNA in stolons are the result of movement of StBEL5 RNA from leaves to stolons (Banerjee et al., "Dynamics of a Mobile RNA of Potato Involved in a Long-Distance Signaling Pathway," Plant Cell 18:3443-57 (2006); Banerjee et al., "Untranslated Regions of a Mobile Transcript Mediate RNA Metabolism," Plant Physiol. 151: 1831-43 (2009); and Lin et al., "The Impact of the Long-Distance Transport of a BEL1-Like mRNA on Development," Plant Physiol. 161:760-72 (2013), which are hereby incorporated by reference in their entirety). In this model, mobile StBEL11 and StBEL29 contain the tandem TGAC motif specific for the BEL/KNOX complex in their upstream sequence. Data represent the mean±standard deviation of two biological reps and two technical reps. One or three asterisks indicate a significant difference at a 0.05 or 0.001 level, respectively, using a Student's t test.

Figure 19:
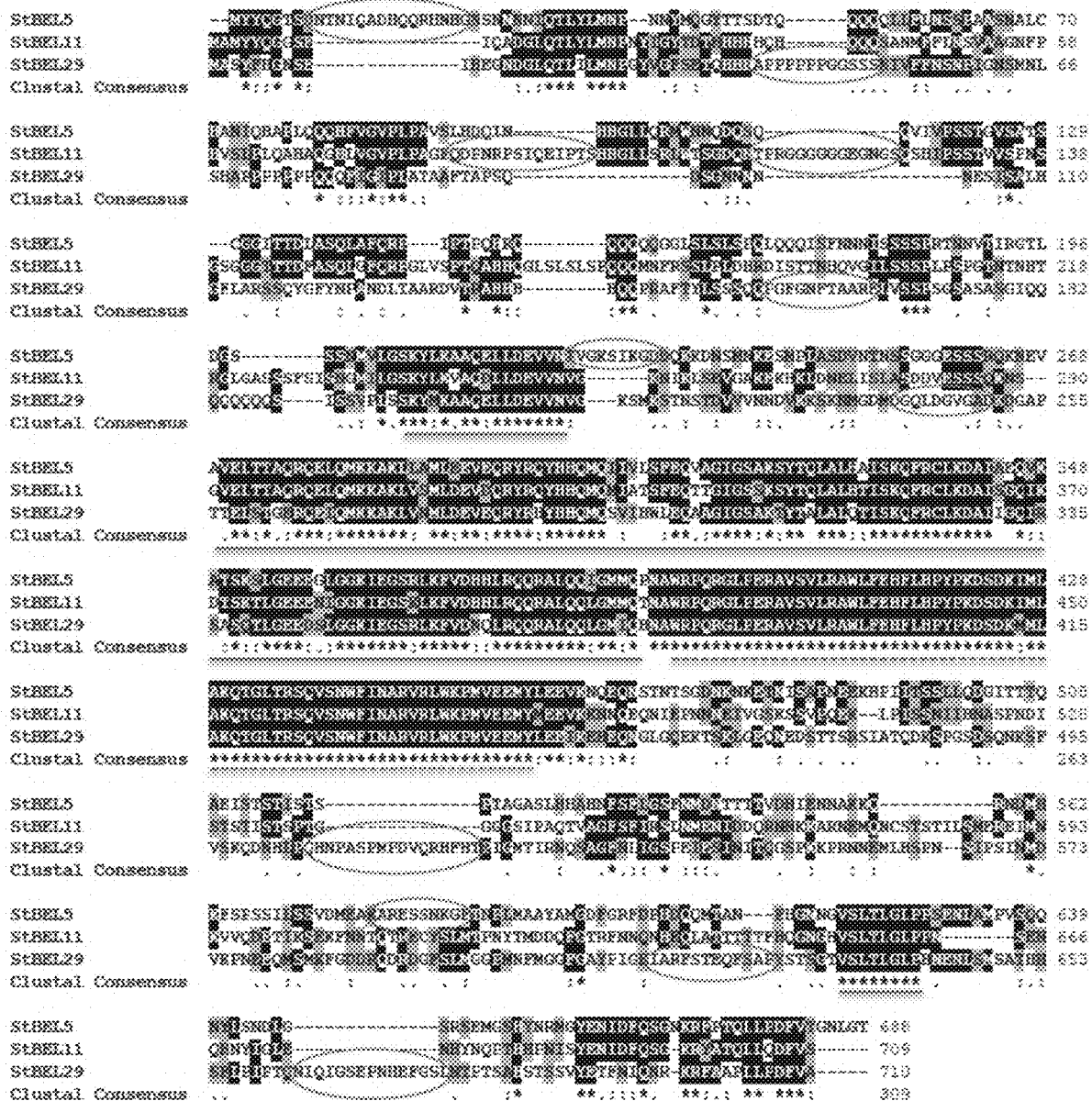

FIG. 19 shows an amino acid sequence alignment of StBEL5 (SEQ ID NO:51), StBEL11 (SEQ ID NO:52), and StBEL29 (SEQ ID NO:53). Black- and gray-boxed letters represent identical or similar residues, respectively. The conserved BELL domain and the N-terminal Sky and C-terminal VSLTLGL boxes have been underlined. The homeodomain is marked by a dashed line. The amino acids for conserved domains are aligned in relation to the BEL5 protein. Ovals highlight areas of eight residues or more of unique sequence.

DETAILED DESCRIPTION OF THE INVENTION

Generally, the present invention relates to nucleic acid molecules encoding BEL transcription factors from potato (Solanum tuberosum L.), BEL transcription factor is a general term used herein to mean a member of the BEL-1-like family of transcription factors, which includes a BELL domain (Bellaoui et al., "The *Arabidopsis* BELL1 and KNOX TALE Homeodomain Proteins Interact Through a Domain Conserved Between Plants and Animals," *Plant Cell* 13(10:2455-70 (2001), which is hereby incorporated by reference in its entirety) and which regulates growth, in particular, floral development.

A description of the BEL mobile mRNA and their regulation of tuber development in potato—including the mechanisms mediating their mobility—are further described in Hannapel and Banerjee, "Multiple Mobile mRNA Signals Regulate Tuber Development in Potato," *Plants* 2017: 6, S (2017), which is hereby incorporated by reference in its entirety.

One aspect of the present invention is directed to a nucleic acid construct comprising a first nucleic acid molecule comprising a nucleotide sequence configured to silence or reduce expression of StBEL11 and variants thereof; a 5' DNA promoter sequence; and a 3' terminator sequence, where the first nucleic acid molecule, the promoter sequence, and the terminator sequence are operatively coupled to permit transcription of the first nucleic acid molecule.

The mRNA of StBEL11 has a nucleotide sequence of SEQ ID NO:1, as follows, where the 5' UTR and 3' UTR are shown in italics, preceding and following the CDS, which is shown in regular font:

```
tttaagaaaa tctctcactt tctctttctc ccaattataa taagaaaact ttctttcctc    60
cttgttttta tttttaaaaa aatatttcag tttagtttat ggttgaagat atttgatata   120
gccttcatat atgtcactca tgttccatca tcagccaagt gttagaagtc actttcttta   180
acaagatttt cttgaaaaat atttaaaaaa ttgaactcca aaaaaaagaa aaaaaggagt   240
gtagttttct tgattggttg tgaaatttat ggctatgtac tatcaaggag gctcagaaat   300
ccaagctgat ggtctgcaga cactttattt gatgaaccct aactatatag gctacactga   360
cacacatcat catcatcatc aacaccaaca acaatcagcc aacatgtttt tcttgaattc   420
tgtggcggcg gggaatttc  cccacgtgtc cctccctttg caagcacatg cgcagggca    480 cttggttgga gtgcccctgc cagctggttt tcaagatcct aaccgcccTT ccattcagga   540
aattccgacc tctcatcatg gccttttatc gcgtttgtgg acttctggtg accaaaatac   600
ccctagaggt ggtggaggag gaggagaagg aaatggaagt caatcacata taccgtcttc   660
cacggtggtt tctcccaact caggtagtgg gggaggcacc accacggact ttgcttccca   720
attagggttc caaagaccgg ggttggtgtc accaacacag gcgcaccatc aaggtctttc   780
tctaagcctt tctccacaac aacaaatgaa tttcaggtct agtcttccac tagaccaccg   840
cgatatttca acaacaaatc atcaagttgg aatactatca tcatcaccat taccatcacc   900
aggaacaaat accaatcata ctcgaggatt aggggcatca tcgtcttttt cgatttctaa   960
tgggatgata ttgggttcta agtacctaaa agttgcacaa gatcttcttg atgaagttgt  1020
taatgttgga aaaacatca  aattatcaga ggttggtgca aaggagaaac acaaattgga  1080
caatgaatta atatctttgg ctagtgatga tgttgaaagt agcagccaaa aaaatagtgg  1140
tgttgaactt actacagctc aaagacaaga acttcaaatg aagaaagcaa agcttgttag  1200
catgcttgat gaggtggatc aaaggtatag acaataccat caccaaatgc aaatgattgc  1260
aacatcattt gagcaaacaa caggaattgg atcatcaaaa tcatacacac aacttgcttt  1320
gcacacaatt tcaaagcaat ttagatgttt aaaagatgca atttctgggc aaataaagga  1380
cactagcaaa actttagggg aagaagagaa cattggaggc aaaattgaag gatcaaagtt  1440
gaaatttgtg gatcatcatt tacgccaaca acgtgcacta caacaattag ggatgatgca  1500
aaccaatgca tggaggccac aaagaggttt gcccgaaaga gcggtttcgg ttctccgtgc  1560
ttggcttttc gagcattttc ttcatccgta tcccaaagat tcagataaaa tcatgcttgc  1620
taagcaaaca gggctaacaa ggagccaggt atcaaattgg tttataaatg ctagagttag  1680
actatggaag ccaatggtag aagaaatgta catggaagaa gtgaagaaaa acaatcaaga  1740
acaaaatatt gagcctaata acaatgaaat tgttggttca aaatcaagtg ttccacaaga  1800
gaaattacca attagtagca atattattca taatgcttct ccaaatgata tttctacttc  1860
caccatttca acatctccga cgggcggcgg cggttcgatt ccggctcaga cggttgcagg  1920
```

-continued

```
tttctccttc attaggtcat taaacatgga gaacattgat gatcaaagga acaacaaaaa   1980
ggcaagaaat gagatgcaaa attgttcaac tagtactatt ctctcaatgg aaagagaaat   2040
catgaataaa gttgtgcaag atgagacaat caaaagtgaa aagttcaaca acacacaaac   2100
aagagaatgt tattctctaa tgactccaaa ttacacaatg gatgatcaat ttggaacaag   2160
gttcaacaat caaaatcatg aacaattggc aacaacaaca acaacttttc atcaaggaaa   2220
tggtcatgtt tctcttactc tagggcttcc accaaattct gaaaaccaac acaattacat   2280
tggattggaa aatcattaca atcaacctac acatcatcca aatattagct atgaaaacat   2340
tgattttcag agtggaaagc gatacgccac tcaactatta caagattttg tttcttgatg   2400
atatatataa tttgcaggta aatcagcttg aaattacatc atgaaaggcc ttgaataaaa   2460
gaaggggagt tgagatctag tgatcatata aatatgtata ggtagaaagt ttagttagta   2520
tatataggtt atacttctag tttcttaaat ggagatacaa tttttgttgt tattttgta    2580 ttgagataac tagctagctt ggattattta aagttgttgc atgcaaccaa agaagaagaa   2640
aaaataatct atatatgcaa actatagtat gttgtaaatt ttgtgcgtct ttttgtttca   2700
atttgcatat atgtaaac                                                 2718
```

The mRNA of StBEL11 described above is derived from StBEL11, having a nucleotide sequence of SEQ ID NO:2, as follows, where the upstream sequence is shown in italics, introns are shown in regular font, and exons are shown in bold:

```
tttttttat gtatatatac atttgatgaa gataatgttc tcttaagtga aaatcttgct    60
tttatcatta gttagtactt acaattcttt ctgtcttatt ttatatgata ttttttaaa    120 tttagtttac cccgaaaata aatgatatgt ttttatatat ttaactaatt caatttaact   180
aattcaattt taaacttctt tgaatctcaa tcgaattgcc tcattttga gaaggagttc    240 gatttcaaac ccagattcga tccactccaa gaaaagaga aagaaaaac aaatcaacta     300 cgaaccccca ccccaccccca ccccaccccc caccatcgga aaaagggtca taagtagaaa  360
taaagaaaaa ttgagggact tctagcaact aatgtaatca attatgtatt atatatggac  420
ccaacaaatt ggtggaaaaa gacgtttcct cattttcat atatctatgg cctacttcct   480
ttaagttaat gttttttttc ttcatctaat tttaagtcga gtatttattt tgagactcgg  540
attaatttaa attgatgttt tcaggaaaat ttatcaaaag tgaaaatcta acttattgag  600
aattttctta tttgtatgat ttaaatttgt aacctctaaa taaagatgaa aaatcttaat  660
catttcatca ttactcgtaa ttatttttctt cttgttagtg ttcactatac tctctctttc  720
tctctaaaga tattttttgaa aaaaaatatc taaattatgc cagcatcaaa tcattttata  780
atagtgaaat taagattggg tctatttatt ttttccatca cacgtatgta gaaccccca   840 ccccaccct cgccgccacc ccaccccctt actatcgagt ttaactaata tttattagta   900
taaaaattat atttatctgt tataacaagt aaaatgtctt attttttaaaa ggataaaggt 960 atgagaaata tcccaactt gatcggatt actgttgcga tactaaactt tcatgaggat  1020
ctattacctc cttcgactat ttaataccgt attttttatcc ccctgaacta tttaatattg 1080
tattttaaag gtatatatga ttatatgtgc caacgtggac acattactat ttataatttt  1140
gcattatttt ttatgtccac gtggacaaat atatatgttt aaaatacggt attaaatagt  1200
ctagggagct aataggtcct catgaaagtt tagtatcgca acaacaaatt cgatcaaagt  1260
tgagatattt ttcaggccct tatccctatt tttaaaattg aaagtttaca ttttatgaa   1320
```

```
gggttaaaac atgtaacatc atttaggtaa cttgatatag tataaaaaat tatttacatt   1380
atatataaat taaattcatg attactaaaa gaattcaatc atcaggtcat ctttatctat   1440
gaaatgtttt atttgtaaaa ttacaaacct cacatttaaa aaagtttatc tataaatata   1500
ttttaaata accttcctga taatgtaaaa atatttatac tgacgattct tactgatttt    1560
tttttactg tgttttgag gggtggggtg ggggtgaggg taaggggat atgttgggag      1620
acttacacta aataaacatg tcttctttat tcatattccc ctttatgtgt tgtggagttt   1680
```
taagaaaatc tctcactttc tctttctccc aattataata agaaaactt ctttcttcct   1740
tgttttatt tttaaaaaaa tatttcagtt tagtacatgg ttgaagatat ttgatatagc   1800
cttcatatat gtcactcatg tgagtacaac ttttctccat atatatcaaa atcaagattt 1860

```
tcatagttga gtgattaatt aattgtatat aactcatcat atattatttg aatttctctt   1920
gttaaaaatg ttttctatct ttagggtatt gcatggattt attataattt ttttctatct   1980
tactttctaa tttcaggttc catcatcagc caagtgttag aagtcacttt ctttaacaag   2040
```
attttcttaa aaaatattta aaaacttgaa ctccaaaaaa aagaagaaaa ggagtgtaat   2100
tttcttgatt ggttgtgaaa tttatggcta tgtactatca aggaggctca gaaatccaag   2160
ctgatggtct gcagacactt tatttgatga accctaatta tataggctat actgacacac   2220
atcatcatca tcaacaacac caacaacaat cagccaacat gttttcttg aattctgtgg    2280
cggcggggaa ttttccccac gtgtccctcc ctttgcaagc acatgcgcag gggcacttgg   2340
ttggagtgcc cctgccagct ggttttcaag atcctaaccg cccttccatt ccggaaattc   2400
cgacctctca tcatggcctt ttatcacgtt tgtggacttc tggtgaccaa aataccccta   2460
gaggtggtgg aggaggagga gaaggaaatg gaagtcaatc acatataccg tcttccacgg   2520
tggtttctcc caactcaggt agtgggggag gcaccaccac ggactttgct tcccaattag   2580
ggttccaaag accggggttg gtgtcaccaa cacaggcgca ccatcaaggt ctttctctaa   2640
gcctttctcc acaacaacaa atgaatttca ggtctagtct tccactagac caccgcgata   2700
tttcaacaac aaatcatcaa gttgaatac tatcaccatc accattacca tcaccaggaa    2760
caaataccaa tcatactcga ggattagggg catcatcgtc ttttcgatt tctaatggga    2820
tgataatggg ttctaagtac ctaaaagttg cacaagatct tcttgatgaa gttgttaatg   2880
ttggaaaaaa catcaaatta tcagagggtg gtgcaaagga gaaacacaaa ttggacaatg   2940
aattaatctc tttggctagt gatgatgttg aaagtagcag ccaaaaaaat attgttgttg   3000
aacttactac agctcaaaga caagaacttc aaatgaagaa agccaagctt gttagcatgc   3060
ttgatgaggt atatatactt ctaattattc atatattaat taattaatca tatatatata 3120

```
ttaatcaaat tattcatata ttaattaatt aatcaatacc aagtttcttg atttggagtt   3180
tgatcattta ggcaaatttc actactatat ataaaacaca aattctaacg gatgtttggt   3240
cagtaagaaa ttctcaattt tcaatcaaac atctattaga atttcacgtt ttttagtagt   3300
gaaattaatt aaataatcta aaaattgttc aatcgaattt acaacaaaac atccattgaa   3360
attttacttt cttttcaata gcgaaaccaa ttaaatagga ttgactaccc aattaatagt   3420
tattatctta tcttcttctt gatttcaatc ttttttcaat aaaagagta attttaatta    3480
tgagataata aactactgat tagttatgac aatctgaaaa atcaactcct attaaatgat   3540
ccaaaaagtg tacaaatttg tatatcttaa tgttaatttc attgttttat ttatttatttt  3600
agttgctttt ttttccttct tgggaagggg gaggggtcaa gttgctattg attcatatac   3660
tagcaataat tattgattta tttcaaaggt acaatttgt tcatcatgaa actataagct    3720
```

-continued

```
agacaatata tgtggttcta agcttttttc tattgggggt ccaactaaag ttaaagataa   3780
tacacctaat atgtcttgtt gagttgacaa aaaatcaaag gcacgtggtc ttattcaatc   3840
actttattag aacctttcaa atttggaaat attcttacct ttcttttgag ataatcacat   3900
aaaaataaac ctttggaata atttatattt ttggtattcc tattgatatt tgatatctgt   3960
tttgaagctt aactaatata aatatgcgtc gaaaagttat ctcactttag gagattaaaa   4020
tgcttcttag taaaagtgac ttcatattca ggactcgaat aatattactt gatgatcatt   4080
tggacacaat tgatcaattg ggaaataatg aaatattatt ttgcaaatca agttttattt   4140
tataatttca ttagttattt cgacttgaac ttgaaataaa gaatctgaag tttgaaaaat   4200
tgatttaaag agtattttt tccactctaa gaacttcaaa caatttcaac ttcaacttca   4260
tataatcata tttttttca acttcaatca gatatcgtcg tgatatgatc aatatcaatc   4320
tacttatttt tattttattg tttgtatttt tttttgaatt ttttataggt ggatcaaagg   4380
tatagacaat accatcacca aatgcaaatg attgcaacat catttgagca aacaacagga   4440
attggatcat caaaatcata cacacaactt gctttgcaca caatttcaaa gcaatttaga   4500
tgtttaaaag atgcaatttt tgggcaaata aaggacacaa gtaaaacttt aggggaagaa   4560
gagaacattg gaggcaaaat tgaaggatca aagttgaaat ttgtggatca tcatttacgc   4620
caacaacgtg cactacaaca attagggatg atgcaaacca atgcatggag gccacaaaga   4680
ggtttgcccg aaagagcggt tcggttctc cgcgcttggc ttttcgagca ttttcttcat   4740
ccgtaagtat ttgttgaaga cataattaag taaattaata tgcatgtctt ttaatagttt   4800
aagattttaa acaaagcaat cacaacatcc tacatgtttc accgcttgtt ctccttatta   4860
ggaaaaataa ccaattgttc tagagtatat gagaaagaat cagactcgca atctagcatt   4920
tgaagtggca aatacaagac taattaagta aatacaattt ttttttttaa aataacagtt   4980
taaacttttg aatgagatag atttaattaa caccttatat tacctataag aaatgaactt   5040
caatctctat ttttttttta aaacaattt tatacaccat gtagaaacct ttataaagaa   5100
attaaattaa atcactcata ccatttcttt taaatttcaa taaataaatt atatatttct   5160
tgtcttgcag gtatcccaaa gattcagata aaatcatgct tgctaagcaa acagggctaa   5220
caaggagcca ggttcttgaa aaattcatca tctcaattta tatgacgcat ttttaacat   5280 atctaaaaaa gacgttttat ttctaattta gaaacaataa aattttaaaa ttctcaacaa   5340
tcatagtacc tctctatata actgtaacaa catcttatta taacaaccaa ttttttgaat   5400
atgccgtaaa aaagacatta tatttcaat ttaggaacaa tataacttta aaattctcaa   5460
caatcatagt acctctctat ataactgtaa caacatctta ttataacaac caattttttg   5520
aatatgccgt aaaaagaca ttatattttc aatttaggaa caatataact ttaaaattct   5580
caacaatcat agtacctctc tatataacag taacaacatc ttgttataac aaactaagtt   5640 ctttttaaa ccaactttca ctacaacaaa gataactttt agcggcaata tacatattaa   5700
taaagaatac taaagctttt accggcatta gttaatttca ttggatccat tatcgctata   5760
gactgtagat acatttacaa aaagtattaa ttaccactaa aaacacatat gtagtggcaa   5820
ttttgctatt gctattaatt aattaatgtt ataaatataa ttttttaatgt agtgtttcat   5880 gttatgttaa agtcatgtag tatatgttct ctacgaataa tatttcacta tatcagacaa   5940
aaaatatcta gaataaacaa tgatgttata gaaagatttg acagcaagtc acacaaatat   6000
gtacttaaga gtacttattt tagactacaa gttttaaaag tcgatcgtct gttctttctt   6060
aaaatacttt tgaaaatgca ggtatcaaat tggtttataa atgctagagt tagactatgg   6120
aagccaatgg tagaagaaat gtacatggaa gaagtgaaga aaaacaatca agaacaaaat   6180
```

-continued

```
attgagccta ataacaatga aattgttggt tcaaaatcaa gtgttccaca agagaaatta 6240
ccaattagta gcaatattat tcataatgct tctccaaatg atatttctac ttccaccatt 6300
tcaacatctc cgacgggtgg cggcggttcg attccggctc agacggttgc aggttagttg 6360
gaatataaag aaagtcattt taaaagttgt cgttgtttga cctataatag gttttgagtc 6420
gtggaaggca tcactaattt gcataaaggt aggttgtccc cttggggtat ggtcttttca 6480
tggagtaacg gtagagttgt ttccactgac ctatataagt tacaggttcg agttgtggaa 6540
ttggttgcgt tgttgatgct catgtcgggg tagactgtct acaacacaca ccttgagata 6600
caacctttta ttgtacccta catgaatgtg aaatacttca cgcaccaaac tgcctaataa 6660
ctcttagaaa agaacacact tgactcacac atctatatat ctacgtagta cctcaattga 6720
taaataatct aggatgatta gatggttaca catatcaaac atataatagg ttcaagtcgt 6780
agaaggcgtc actaatttgc atcaaggtag gttgtccccct tggggtatga tcctttcatg 6840
gaccatgtag acactcttga agttgagtct tgaagtaaca gtaaagtcat ctccacgtga 6900
cctatatata taagtcacaa cttcgagttg tggagttggc taggctctca tcaggataga 6960
ctgtcgacat cacacttctt gaaatgcaac cttttttcga accttatgtg aatgtgagac 7020
tacactcttg actaacatct atataactac tatacctcaa ttaataaaca atctaggata 7080
attagatggt ctcacactct aaacacctag gttagatcaa aagacaataa aactagctag 7140
agtacatttt tatttattgt aacaagtgtt acttatcaaa gtgtgactct atattgttta 7200
actaattaac atgtttaatt tgtctaaaca ggtttctcct tcattaggtc attaaacatg 7260
gagaacattg atgatcaaag gaacaacaaa aaggcaagaa atgagatgca aaattgttca 7320
actagtacta ttctctcaat ggaaagagaa atcatgaata aagttgtcca agatgagaca 7380
atcaaaagtg aaaagttcaa caacacacaa acaagagaat gctattctct aatgactcca 7440
aattacacaa tggatgatca atttggaaca aggttcaaca atcaaaatca tgaacaattg 7500
gcaacaactt ttcatcaagg aaatggtcat gtttctctta ctctagggct tccaccaaat 7560
tctgaaaacc aacacaatta cattggattg gaaaatcatt acaatcaacc tacacatcat 7620
ccaaatatta gctatgaaaa cattgattt cagagtggaa agcgatacgc cactcaacta 7680
ttacaagatt ttgtttcttg atgatatata taatttccag gtaaatcaac ttgaaattac 7740
atcatgaaag gccttgaata aaagaagggg agttgagatc tagtgatcat atatatatgt 7800
ataggtagaa agtttagtta gtatatatag gttatacttc tagtttctta aatggagata 7860
caatttttgt tgttgttttt gtattgagat aactagctag cttgggttat ttaaagttgt 7920
tgcatgcaac caagaagaa gaaaaaataa tctatatatg caaactatag tatgttgtaa 7980
attttgtgct tcttttaatt agtttcaatt tgcatatatg taaac         8025
```

According to one embodiment, the nucleic acid construct of the present invention comprises DNA heterologous to the first nucleic acid molecule. In one particular embodiment, the DNA heterologous to the first nucleic acid molecule is the 5' DNA promoter sequence.

In one embodiment, the first nucleic acid molecule comprising a nucleotide sequence configured to silence or reduce expression of StBEL11 has a nucleotide sequence of SEQ ID NO:3, as follows:

```
gaaatttatg gctatgtact atcaaggagg ctcagaaatc caagctgatg gtctgcagac  60
actttatttg atgaacccta actatatagg ctacactgac acacatcatc atcatcatca 120
acaccaacaa caatcagcca acatgttttt cttgaattct gtggcggcgg ggaatttttcc 180 ccacgtgtcc ctcccctttgc aagcacatgc gcaggggcac ttggttggag tgccctgcc 240 agctggtttt caagatccta accgcccttc cattcaggaa attccgacct ctcatcatgg 300
```

```
ccttttatcg cgtttgtgga cttctggtga ccaaaatacc cctagaggtg gtggaggagg    360
aggagaagga aatggaagtc aatcacatat accgtcttcc a                        401
```

Other nucleic acid molecules may also be used as the first nucleic acid molecule comprising a nucleotide sequence configured to silence or reduce expression of StBEL11. For example, in certain embodiments, the first nucleic acid molecule has a nucleotide sequence that is at least about 95%, 96%, 97%, 98%, or 99% identical to the nucleotide sequence of SEQ ID NO:3.

By way of other examples, the first nucleic acid molecule has a nucleotide sequence that is at least about is at least 70%, 75%, 80%, 85%, 90%, 91%, 92%, 93%, or 94% identical to the nucleotide sequence of SEQ ID NO:3.

In certain embodiments, the first nucleic acid molecule comprises at least 20, 21, 22, 23, 24, 25, 26, 27, 28, 29, 30, 35, 40, 45, 50, 55, 60, 65, 70, 75, 80, 85, 90, 95, 100, 125, 150, 175, 200, 225, 250, 275, 300, 325, 350, 375, or 400 contiguous bp of SEQ ID NO:3.

In certain embodiments, the first nucleic acid molecule comprises at least 20, 21, 22, 23, 24, 25, 26, 27, 28, 29, 30, 35, 40, 45, 50, 55, 60, 65, 70, 75, 80, 85, 90, 95, 100, 125, 150, 175, 200, 225, 250, 275, 300, 325, 350, 375, or 400 contiguous bp of SEQ ID NO:2 which are less than 70%, 65%, 60%, 55%, 50%, 45%, 40%, 35%, 30%, 25%, 20%, 15%, 10%, 5%, or 1% identical to any portion of SEQ ID NO:8, where the portion of SEQ ID NO:8 has the same length as the first nucleic acid molecule.

According to this embodiment, one can silence or reduce expression of StBEL11 without silencing or reducing the expression of StBEL5.

Methods for identifying nucleic acid molecules capable of silencing or reducing expression of genes and/or related RNA molecules are well known in the art and are discussed in more detail infra.

Nucleic acid molecules capable of silencing or reducing expression of StBEL11, using any of the methods described infra are contemplated.

In a further embodiment, the nucleic acid construct according to this aspect of the present invention further comprises a second nucleic acid molecule comprising a nucleotide sequence configured to silence or reduce expression of StBEL29 and variants thereof.

The mRNA of StBEL29 has a nucleotide sequence of SEQ ID NO:4, as follows, where the 5' UTR and 3' UTR are shown in italics, and the CDS is shown in regular font:

```
ttctttcttt ctttctcctc tctctctctc taaaaagttg agtactttta ttagctctca     60
tcacttcaca cagaagaaga tggtattttt atttctttct gctgatggct gcatcaaatg    120
atttgaaaag ctgagtcaaa tcagaagaag aaaaagaaag ttataataat aataatgata    180
atatcaaaaa tattattttc agattagttg gtgttatttg tttattgtgg agaaaaaata    240
aattaaaaag gaagaaaaaa tggcatctta ttttcatgga aattcagaaa tacatgaagg    300
aaatgatgga ttacaaactc taatactaat gaatcctgga tatgttggat tttctgaaac    360
acaacatcac cacgcgccac cgccgccgcc gccaggtggc agcagcagca acatagtttt    420
cttcaactcc aatcctattg gaaattcaat gaacttatct cacgcgccac cacctcctcc    480
accgcctcaa caacaattca tcggtatacc cctcgccacc gccgccttca ccgccccatc    540
ccaagactcc ggtaacaaca acaacaacga gtcaatctcc gcccttcacg gcttcctagc    600
tcgatcgtct cagtacgggt tttacaaccc ggcaaacgac ctcacggcgg cgcgtgacgt    660
cacacgcgct catcatcatc atcagcagcc aagggcttc acttacctgt cctcgtccca    720
gcagccgggg tttgggaact tcacggcggc gcgtgagctt gtttcttcgc cttcgggttc    780
ggcttcagct tcagggatac aacaacaaca acagcaacaa cagagtatta gtagtgtgcc    840
tttgagttct aagtacatga aggctgcaca agagctactt gatgaagttg taaatgttgg    900
aaaatcaatg aaaagtacta atagtactga tgttgttgtt aataatgatg tcaagaaatc    960
gaagaatatg ggcgatatgg acggacagtt agacggagtt ggagcagaca aagacggagc   1020
tccaacaact gagctaagta caggggagag acaagaaatt caaatgaaga aagcaaaact   1080
tgttaacatg cttgacgagg tggagcagag gtatagacat tatcatcacc aaatgcagtc   1140
agtgatacat tggttagagc aagctgctgg cattggatca gcaaaaacat atacagcatt   1200
ggctttgcag acgatttcga agcaatttag gtgtcttaag gacgcgataa ttggtcaaat   1260
acgatcagca agccagacgt taggcgaaga agatagtttg ggagggaaga ttgaaggttc   1320
aaggcttaaa tttgttgata atcagctaag acagcaaagg gctttgcaac aattgggaat   1380
```

```
gatccagcat aatgcttgga gacctcgag aggattgccc gaacgagctg tttctgttct   1440
tcgcgcttgg cttttgaac atttcctcca tccttatccc aaggattcag acaaaatgat   1500
gctagcaaaa caaacaggac taactaggag tcaggtgtcg aattggttca tcaatgctcg   1560
agttcgtctt tggaagccaa tggtggaaga gatgtacttg gaagagataa aagaacacga   1620
acagaatggg ttgggtcaag aaaagacgag caaattaggt gaacagaacg aagattcaac   1680
aacatcaaga tccattgcta cacaagacaa aagccctggt tcagatagcc aaaacaagag   1740
ttttgtctca aaacaggaca atcatttgcc tcaacacaac cctgcttcac caatgcccga   1800
tgtccaacgc cacttccata cccctatcgg tatgaccatc cgtaatcagt ctgctggttt   1860
caacctcatt ggatcaccag agatcgaaag catcaacatt actcaaggga gtccaaagaa   1920
accgaggaac aacgagatgt tgcattcacc aaacagcatt ccatccatca acatggatgt   1980
aaagcctaac gaggaacaaa tgtcgatgaa gtttggtgat gataggcagg acagagatgg   2040
attctcacta atgggaggac cgatgaactt catgggagga ttcggagcct atcccattgg   2100
agaaattgct cggtttagca ccgagcaatt ctcagcacca tactcaacca gtggcacagt   2160
ttcactcact cttggcctac cacataacga aaacctctca atgtctgcaa cacaccacag   2220
tttccttcca attccaacac aaaacatcca aattggaagt gaaccaaatc atgagtttgg   2280
tagcttaaac acaccaacat cagctcactc aacatcaagc gtctatgaaa ccttcaacat   2340
tcagaacaga aagaggttcg ccgcacccct gttaccagat tttgttgcct gatcacaaaa   2400
acaaaaacag gttttggcaa cagacaaact tctgtcgcta aacaaggaca tgatttagcg   2460
acagataact tcagtcgcta acttagcgac tgaaaacttc tgtcgctaag catgaacatg   2520
tattagcgac atacagtatg caactgtatg tcactaaaca agaacatgat gaattagtga   2580
cggacaactt ctgtcgctaa acaacaaaaa aaaatccatg tttagtata ttgtttctca   2640 ttctatcata tcatggtagt gtaaagaatc aagaaacaag ttttacatag taacagtctt   2700
tatacattgg agatgaagaa ccatttaagt tcttcaaaat agatagattt tctaggttac   2760
ttctacaaga tatatatatg gttgagggtt tgtatattaa ttttgggatt gttatattgg   2820
atgtggaaaa aaagtagtta ttttgggtgg tataaataaa ataatactcc atccatttta   2880
gccaaaaaaa aaaaaaaa                                                 2898
```

The mRNA of StBEL29 described above is derived from StBEL29, having a nucleotide sequence of SEQ ID NO:5, as follows, where the upstream sequence is shown in italics, introns are shown in regular font, and exons are shown in bold:

```
tgagaagaaa acccaaagaa acttatgatt tataataaat tattagaaat ttctatggat     60
ataaaatggt aaaaagtaag ttttattaaa tataaaaata tgttttttt aatggaataa    120 aaagcaaaaa aaaatcacat aaattagaat aaagatcgga gaaagtaaat tataaataaa    180
gacaagatga aaaacaaggc gataatgtaa atcatactaa tcaatcgtta tacatattaa    240
aaaatatcca gcgttacaac aacaaattta acaatataat ataataaaat ttaactaaaa    300
atcaaaataa aatgacattt atcataacaa taattaacaa ccatccaaat atgatgtatg    360
gataaaaggt gaagagtatt agtatctttt gtttaaatct tatatattaa aattataaat    420
ttaattatta ttttaaaaat tcttatataa attttaaatt ctgaatttgt ccgacggcta    480
atctaaagtc aaaagtaaat tttcataaat gtaggtccta aatttttcc cacaattatc    540 ttcttccaag ttgccaacac aaatcaataa tgacaatagg gccctctccc ctatctcttc    600
```

-continued

```
aaccctacct ctcttttct ttctttatca cttcaagttc atatcatatt tcatactctc    660
tcattttctt ctggtctccg ttgtaattta tatgatatat tttttaatat ttaaaataat    720 ttaatttaa attttttata ctctttaaaa aattattata atcataagtt ataaaaaaaa    780
ttaacttttt tttattcagt caaatactat catataaatt aaaaaagaaa aagtatatgt    840
taaatcctta taattattat tgttaaagaa gaaaaaggg aggttagtgg aagtggacgt    900
tacctcgttt ttcatctgtc tgttttttct gacacaccct tgatctttga tgatggatac    960
gtcgctccgt tcatatttag gtgatactat attaatttca agagttaaat aatgataaat   1020
cacctaagac cgctaatgtt ccatctaatt caagaacaag cccttctcaa tgtcttgcct   1080
ttcgcatgtg ttttctttga aattggaatt ccaaccaagt tcccttccca aagcgggaac   1140
aagttggtgc gaccgattaa agaagaagga caaagagtta aataatgaaa ttataattat   1200
tttatattaa ttattataat ttataatatt ttttaaaaac taaatgttct aatttaaagg   1260
caaagtccaa atatttattt tataaatttt gaagcataat tgggttttga ttaattattt   1320
atatcaaatt aaatttattt taatacaaat acataattta agacaaagct attgagttaa   1380
agttatgtca aattaaatcc gtaactttat aagctcaagg ggagaaagag agaaggattg   1440
ttcattcctt ataacgagtc tagagatctc atcctttatc gatgtaaggt tctttccatt   1500
catcactccc ttgcgttaga accttttttt tttagactgg agcgtgcaca ttcatggacc   1560
attcttccca ttcgtcaatc cctcgtgtta gaattttttat ttctcgaact agagtgtgtg   1620
cattaacaga taccagatac cgatattttc accctcattc aagccgtctc tggaagagct   1680
atattggatg agcctgactt tgataccata tcaaattaac tcttcaacct aattcataca   1740
tcaaaagcta gctcgcctta taagaagtct ttccattcgt cactccctcg tgttacaact   1800
tacaagacta gctcaataaa aaattatcgt ccaaattta taagaagtcc attcatcaat   1860
agcacctttc ctatttgtat ttgcacttaa aaaaaaaag gtgacttttg aaatttgaat   1920
tatgccacat aaattatcct tcggtatagc ccaatgattt gaccttggta ctttcatatt   1980
ggaggtctca aatttgaaat tccttaccag taaaaataaa aaatttaccct tcctgaatcg   2040 aacttatcgc gccagacttc cttagacaca caaattagaa taaaaaagt atattttatt   2100 tttatatata agcaaaaaca cacactaact cacattcaca catccacatc tttctttctt   2160
tctttctcct ctctctctct ctaaaaagtt gagtacttt attagctctc atcacttcac   2220
acagaagaag atggtatttt tatttctttc tgctgatggc tgcatcaaat gatttgaaaa   2280
gctgagtcaa atcagaagaa gaaaaagaaa gttataataa taataataat aatatcaaaa   2340
atattatttt caggtatggt acttctttac tcattaacaa tgtaaatata gaatttgaag   2400
tttacgagct agttttctct cttttttat tttgactagc agaaacagag tcagagtcag   2460
aatttgaagt ttataagtct tgaattctga ttttgtttga gttcttgagt tctgaattga   2520
taatttatac atgttgaatg aattttgtaa gtatactttg aaacaaatct attgagttcg   2580
attgaattca taaccgacac tttagttccg ccacttttca gaggcggatc cagaatatga   2640
aggttatgac ttatgagtat tgtaaccttt tgagttactg aattctaaat taattttata   2700
agtgagtaaa tacaaaattt gaaacaaaat tagctattga gttcagttga attcgtataa   2760
ccgacactct agctttgtca ctgctcaaag actgatctag aatttgaagt ttatgagttt   2820
tgaattctaa attgataatt tctacatgtt agatggaatt tttaagataa atataaatta   2880
aaattattga gttcgatcga attcgatttg tgttttcctt tttcttcacc ttatttatca   2940
agagaaatta ttttaatttt tttttatcat tactgattca taaatctata tagatatata   3000
tagatggata cattagagtt cctaaaaaat gttataaaga gtattttgtt tttccctttc   3060
```

-continued

```
ttgattttttt ttcgaaacta agatttcaat tttatcattt ctgaattttta taacaacgat    3120
tatcatagaa ttctaaattt actagttata catatttatt taacgaatta ttaacataaa    3180
tgcattattt gaataaaatt tattagattt gaccgaactc gtatatgaac tttctctctc    3240
atgtaatttc agccgtaact gtgtgtattt cctttctctc tctaaaaaat ctgttatggt    3300
gttctgtgtc actctaacaa aaataaaatt attcttcatt tcttccattg tcagattata    3360
atacaccacg tgcacttaca aattttgtga aaaccatatt ttaatttaca aatccttttc    3420
ataattcttt ttttttaatca agaaaattaa atttaattac attaagtatt ttttacaata    3480
atattaacat attactaaat aaattttcag gtttatttta ccattttttgt gattttgaag    3540
tgttacaaag tgtgaatggg ttggactttt tggacctcag ctaggtagct tcttgtcttc    3600
aacacaaaag gtacatataa aaattacaat aaaattataa ccacttttac ttaggaattt    3660
taccatattt aggtaaaaaa aataaatcac tcgcctagtc gtaataatca gtagcagagc    3720
tagaggaacg aaaggcttca tctgaatctt ctttatctga aatcatactg tatataaggt    3780
caaaattcat tttttatgaa cacttttgat gaaaatcatg tctctgccac taaagtcgta    3840
atttgtaggc atcaacaata tgtatatata tatatatata gtgattattg attatatacg    3900
gtatatattg gttaaaagtt ttgaaaaata aggattaaag ttaatttcca ttgtgtgttt    3960
tcttgggatc aggggcggag ctagataagt gtaaaaaggg tttatctaga cttcttccga    4020
ccaaaaatta tacttatata catatacata gtagatactg aatcccttgc ttttttcgta    4080
tatgtacttc cgcatatttt aaatttcttt aatgaaaatt ctgactcata tactgtttga    4140
atgtttttgt atttaatata tgtatgtttt gcctttttat tttggaaaaa atgatatatg    4200
tggacttact tgacttgact ttaacttatt tttttttatt tttcagatta gttggtgtta    4260
tttgtttata gtggagaaaa aataaattaa aaaagaagag aaaatggcat cttatttca    4320
tggaaattca gaaatacaag aaggaaatga tggattacaa actctaatac taatgaatcc    4380
tggatatgtt ggattttctg aaacacaaca tcaccacgcg ccgccgccgc caggtggcag    4440
cagcaacaac atagttttct tcaactccaa tcctcttgga aattcaataa acttatctca    4500
cgcgccacca cctccgccac cgccacaaca catttcgtc ggtataccctc tcgccaccgc    4560
cgccttcacc gccccatccc aagactccgg taacaacaac aacaacgagt caatctccgc    4620
ccttcacggc ttcctagctc gatcgtctca gtacgggttt tacaacccgg ctaacgacat    4680
cacggcggcg cgtgaggtca cacgcgctca tcatcagcag cagcaagggc tttcacttag    4740
cctgtcctca tcccagcagc ctgggtttgg gaacttcacg gcggcgcgtg agattgtttc    4800
ttcgcctacg cgttcggctt cggcttccgg gatacaacaa caacaacagc aacaacaaag    4860
tattagtagt gtgcctttga gttctaagta catgaaggct gcacaagagc tacttgatga    4920
agttgtaaat gttggaaaat caatgagaag tactaatagt actgaagttg ttgttaataa    4980
tgatgtcaag aaatcgaaga ttatgaccga tatggatgga cagatagatg gaggagcaga    5040
caaagacgga actccaacaa ctgagctaag taccgcagag aggcaagaaa ttcaaatgaa    5100
gaaagcaaaa cttgttaaca tgcttgacga ggtaaccttg ttgtcttttt ctcagtaatg    5160
ttgttgcatt cgtgtcagat cagagtctta aaattagtca atagaagaaa cttcatttcc    5220
tcgagtacgt gtaattgtgg ccttttcgac ttccaactag tatttacaat agtgcactct    5280
acattgataa gcttgacgac aagtaggcaa agcgatggcc ttgttggttg ttatagtttt    5340
ttggttatgt tgctcggact ctgcaaaatt attgtcatac tcaagtcaga ttctccaaaa    5400
tgcactattt ttggagtatc cgacttgcag tctgacattt attttttccg aagagtctga    5460
```

```
gcaacatagg tttcttggc tttccaagat agtaagagaa tggtctctat caaaaaagt      5520 tacatcatat cattactgaa aataagagca aaaaagtatc tgtcaaatga taaagaccag   5580
aacttcaaaa ctgttacttt cgtcagggca ctgtcttgac aattgtaaac aaaaaatgaa   5640
agaatttttc gaaataatt tcttcgaaat ctttgatcta aagctaaata tcggttcgat    5700
tttgggtgtt gttatatagg tggagcagag gtatagacat tatcatcacc aaatgcagtc   5760
agtgatacac tggttggagc aagctgctgg tattggatca gcaagaacat atacagcatt   5820
ggctttgcag acgatttcga agcaatttag gtgtcttaag gacgcgataa ttggtcaaat   5880
acgatcagca ggcaagacgt taggcgaaga agatagtttg ggagggaaga ttgaaggttc   5940
aaggcttaaa tttgttgaca atcagctaag acagcaaagg gctttgcaac aattgggaat   6000
gatccagcat aatgcttgga gacctcgag aggattgccc gaacgagctg tttctgttct    6060
tcgcgcttgg cttttgaac atttcctcca tccgtaagca cgaaacaacc ctttttcatc    6120
agctatgttg ctcggacttt tcaaaaacgt tgtcgcacca gtgttggatc ctcgcagaat   6180
gcattgattt tttgaggatc cgacacatac ctgacgatat ttttgaagag tctgaacaac   6240
atagcttagt taaaagtact gtattttgat atattgtggc aatttgtttt gtatagctat   6300
cccaaggatt cagacaaaat gatgctagca aaacaaacag ggctaactag gagtcaggtc   6360
agtgatatct gataacaaca ttgtcatttt tgattctcga gttgatttct cagatggtca   6420
cttaactgta gttattatat cagaaagtcg ccttacttca acaaagagag tgacattctg   6480
agataataac tgtgagttga gtgaccatct gagaaatcaa ctcttggatt ctccgttttt    6540 ggttttact aagttttgtt tttggacaat tcaggtgtcg aattggttca tcaatgctcg     6600
agttcgtctt tggaagccaa tggtggaaga gatgtacttg gaagagataa aagaacagaa   6660
cggattgggt caagaaaaga cgagcaaatt aggcgaacag aacgaagatt caacaacatc   6720
aagatccatt gctacacaag acaaaagccc tggttcagat agccaaaaca agagttttgt   6780
ctcaaaacag gacaatcatt tgccccaaca caaccctgct tcaccaatgc cgatgtccaa   6840
caccacttcc atacctccta tcggtatgaa catccgtaat cagtctgctg gtttcaacct   6900
cattggatca ccagagatcg aaagcatcaa cattactcaa gggagtccaa agaaaccaag   6960
gaacaacgag atgttgcatt caccaaacag cattccatcc atcaacattg atgtaaagcc   7020
taacgagcaa caaatgtcga tgaagtttgg tgatgatagg caagacagag atggattctc   7080
actaatggga ggaccgatga acttcatggg aggattcgga gcctatccca ttggagaaat   7140
tgctcggttt agcaccgagc aattctcagc accatactca accagtggca cagtttcact   7200
cactcttggc ctaccacata cgaaaaacct ctcaatgtca gcaacacacc acagtttcct   7260
tccaattcca acacaaaaca tccaaattgg aagtgaacca aatcatgagt ttggtagctt   7320
aaacacacca acatcagctc actcaacatc aagcgtctac gaaaatttca acattcagaa   7380
cagaaagagg ttcgccgcac ccttgttacc agattttgtt gcctgatcac aaaaacaaaa   7440
acaggattta gcgacagaca aacttctgtc gctaaacaag aacatgattt agcgacagat   7500
aacttcagtc gctaacttag cgactgaaaa cttctgtcgc taaacatgaa catgtattag   7560
cgacatacag tatacaactg tatgtcgcta aacaagaaca tgatgaatta gtgacggaca   7620
acttctgtcg ctaaacaaca aaaaagatc catgtttag tatattgttt ctcattctat     7680
```

```
catatcatgg tagtgtaaag aatcaagaaa caagttttac atagttacat agtctttata    7740
cattggagat gaagaaccat ttaagttctt caaaatagat agattttcta ggttacttct    7800
agaagatata tatatggttg agggtttgta tattaatttt gggattgtta tattggatgt    7860
ggaaaaaaag tagttatttt gggtggtata aataaaataa tactccatcc attttagcca    7920
a                                                                    7921
```

In one embodiment, the second nucleic acid molecule comprising a nucleotide sequence configured to silence or reduce expression of StBEL29 has a nucleotide sequence of SEQ ID NO:6, as follows:

```
gtgttatttg tttattgtgg agaaaaaata aattaaaaag gaagaaaaaa tggcatctta    60
ttttcatgga aattcagaaa tacatgaagg aaatgatgga ttacaaactc taatactaat    120
gaatcctgga tatgttggat tttctgaaac acaacatcac cacgcgccac cgccgccgcc    180
gccaggtggc agcagcagca acatagtttt cttcaactcc aatcctattg gaaattcaat    240
gaacttatct cacgcgccac cacctcctcc accgcctcaa caacaattca tcggtatacc    300
cctcgccacc gccgccttca ccgccccatc ccaagactcc ggtaacaaca acaacaacga    360
gtcaatctcc gcccttcacg gcttcctagc tcgatcgtct cagtacgggt tttacaaccc    420
ggcaaacgac ctcacggcgg cgcgtgacgt cacacgcgct catcatcatc atcagcagcc    480
aagggctttc acttacctgt cctcgtccca gcagccgggg tttgggaact tcacggcggc    540
gcgtgagctt gtttcttcgc cttcgggttc ggcttcagct tcaggatac aacaacaaca     600 acagcaacaa cagagtatta gtagtgtgcc tttgagttct aagtacatga aggctgcaca    660
agagctactt gatgaagttg taaatgttgg aaaatcaatg aaaagtacta atagtactga    720
tgttgttgtt aataatgatg tcaagaaatc gaagaatatg ggcgatatgg acggacagtt    780
agacggagtt ggagcagac                                                 799
```

Other nucleic acid molecules may also be used as the second nucleic acid molecule comprising a nucleotide sequence configured to silence or reduce expression of StBEL29. For example, in certain embodiments, the second nucleic acid molecule has a nucleotide sequence that is at least about 95%, 96%, 97%, 98%, or 99% identical to the nucleotide sequence of SEQ ID NO:6.

By way of other examples, the second nucleic acid molecule has a nucleotide sequence that is at least about is at least 70%, 75%, 80%, 85%, 90%, 91%, 92%, 93%, or 94% identical to the nucleotide sequence of SEQ ID NO:6.

In certain embodiments, the first nucleic acid molecule comprises at least 20, 21, 22, 23, 24, 25, 26, 27, 28, 29, 30, 35, 40, 45, 50, 55, 60, 65, 70, 75, 80, 85, 90, 95, 100, 125, 150, 175, 200, 225, 250, 275, 300, 325, 350, 375, or 400 contiguous bp of SEQ ID NO:6.

In certain embodiments, the first nucleic acid molecule comprises at least 20, 21, 22, 23, 24, 25, 26, 27, 28, 29, 30, 35, 40, 45, 50, 55, 60, 65, 70, 75, 80, 85, 90, 95, 100, 125, 150, 175, 200, 225, 250, 275, 300, 325, 350, 375, or 400 contiguous by of SEQ ID NO:5 which are less than 70%, 65%, 60%, 55%, 50%, 45%, 40%, 35%, 30%, 25%, 20%, 15%, 10%, 5%, or 1% identical to any portion of SEQ ID NO:8, where the portion of SEQ ID NO:8 has the same length as the first nucleic acid molecule.

According to this embodiment, one can silence or reduce expression of StBEL29 without silencing or reducing the expression of StBEL5.

Nucleic acid molecules capable of silencing or reducing expression of StBEL29, using any of the methods described infra are contemplated.

In one embodiment, the first nucleic acid molecule comprises a nucleotide sequence configured to silence or reduce expression of both StBEL11 and StBEL29. This is possible because of the similarity in sequence between StBEL11 and StBEL29.

In yet another embodiment of this aspect of the present invention, the nucleic acid construct further comprises a further nucleic acid molecule comprising a nucleotide sequence configured to enhance the expression of StBEL5 and variants thereof. This additional nucleic acid molecule may be included in the nucleic acid construct of this aspect of the present invention in addition to the second nucleic acid molecule (described supra) or in place of the second nucleic acid molecule.

The mRNA of StBEL5 has a nucleotide sequence of SEQ ID NO:7, as follows, where 5' UTR and 3' UTR sequences are shown in italics, and the CDS is shown in regular font:

```
catgcagaga taaaaatata gatcagtctg acaagaaggc aacttctcaa agcttagaga    60
gctaccaccc gaagatagac agttagttac atgtactgtt atagataaaa ggagaaatcc   120
gaagaagaaa gaattttttt tgcagatatg tactatcaag gaacctcgga taatactaat   180
atacaagctg atcatcaaca acgtcataat catgggaata gtaataataa taatattcag   240
acactttatt tgatgaaccc taacaattat atgcaaggct acactacttc tgacacacag   300
cagcagcagc agttactttt cctgaattct tcaccagcag caagcaacgc gctttgccat   360
gcgaatatac aacacgcgcc gctgcaacag cagcactttg tcggtgtgcc tcttccggca   420
gtaagtttgc acgatcagat caatcatcat ggacttttac agcgcatgtg aacaaccaa    480 gatcaatctc agcaggtgat agtaccatcg tcgacggggg tttctgccac gtcatgtggc   540
gggatcacca cggacttggc gtctcaattg gcgtttcaga ggccgattcc gacaccacaa   600
caccgacagc agcaacaaca gcaaggcggt ctatctctaa gcctttctcc tcagctacaa   660
cagcaaatta gtttcaataa caatatttca tcctcatcac caaggacaaa taatgttact   720 attagggga cattagatgg aagttctagc aacatggttt taggctctaa gtatctgaaa    780
gctgcacaag agcttcttga tgaagttgtt aatattgttg gaaaagcat caaaggagat    840 gatcaaaga aggataattc aatgaataaa gaatcaatgc ctttggctag tgatgtcaac    900
actaatagtt ctggtggtgg tgaaagtagc agcaggcaga aaaatgaagt tgctgttgag   960
cttacaactg ctcaaagaca agaacttcaa atgaaaaaag ccaagcttct tgccatgctt  1020
gaagaggtgg agcaaaggta cagacagtac catcaccaaa tgcaaataat tgtattatca  1080
tttgagcaag tagcaggaat tggatcagcc aaatcataca ctcaattagc tttgcatgca  1140
atttcgaagc aattcagatg cctaaaggat gcaattgctg agcaagtaaa ggcgacgagc  1200
aagagtttag gtgaagagga aggcttggga gggaaaatcg aaggctcaag actcaaattt  1260
gtggaccatc atctaaggca acaacgcgcg ctgcaacaga taggaatgat gcaaccaaat  1320
gcttggagac cccaaagagg tttacctgaa agagctgtct ctgtccttcg tgcttggctt  1380
ttcgagcatt ttcttcatcc ttacccaaag gattcagaca aaatcatgct tgctaagcaa  1440
acggggctaa caaggagcca ggtgtctaac tggttcataa atgctcgagt tcgattatgg  1500
aagccaatgg tagaagaaat gtacttggaa gaagtgaaga atcaagaaca aaacagtact  1560
aatacttcag gagataacaa aaacaaagag accaatataa gtgctccaaa tgaagagaaa  1620
catccaatta ttactagcag cttattacaa gatggtatta ctactactca agcagaaatt  1680
tctacctcaa ctatttcaac ttcccctact gcaggtgctt cacttcatca tgctcacaat  1740
ttctccttcc ttggttcatt caacatggat aatactacta ctactgttga tcatattgaa  1800
aacaacgcga aaagcaaag aaatgacatg cacaagtttt ctccaagtag tattctttca    1860
tctgttgaca tggaagccaa agctagagaa tcatcaaata aagggtttac taatccttta  1920
atggcagcat acgcgatggg agattttgga aggtttgatc ctcatgatca acaaatgacc  1980
gcgaattttc atggaaataa tggtgtctct cttactttag gacttcctcc ttctgaaaac  2040
ctagccatgc cagtgagcca acaaaattac ctttctaatg acttgggaag taggtctgaa  2100
atggggagtc attacaatag aatgggatat gaaaacattg attttcagag tgggaataag  2160
cgatttccga ctcaactatt accagatttt gttacaggta atctaggaac atgaatacca  2220
gaaagtctcg tattgatagc tgaaaagata aaggaagtt agggatactc ttatattgtg    2280
tgaggccttc tggcccaagt cggaggaccc aatttgatac aacctatcat aggagaaaag  2340
aagtggagac taaattaaag taacaaaatt ttaaagcaca cttctctagta tatatacttc   2400 tttttttat agtatagaaa agaagagatt ttgtgcttta gtgtatagat agagtctact  2460
```

-continued

```
tagtataggt tatacttcta gttccttgag aagattgata caactagtag tattttttt      2520 cttttgggtt ggcttggagt actattttaa gttattggaa actagctata gtaaatgttg      2580
taaagttgtg atattgttcc tctcaatttg catataattt gaaatatttt gtacctacta      2640
gctagtctct aaattatgtt tccattgctt gtaattgcaa ttttatttga attttgtgct      2700
atcattatta gattagcaaa aaaaaaaaaa aaaaa                                 2735
```

The mRNA of StBEL5 described above is derived from StBEL5, having a nucleotide sequence of SEQ ID NO:8, as follows, which includes UTR, exons, and intronic sequence:

```
gtaggtacaa aatatttcaa attatatgca aattgagagg aacaatatca caactttaca       60
acatatacta tagctagttt ccatattaac ttaaaatagt actccaagcc aacccagaaa      120
gaaaaaaaat actactagtt gtatcaatct tctcaaggaa ctagaagtat aacctatact      180
aagtagactc tatctataca ctaaagcaca aaatctcttc ttttctatac tataaaaaaa      240
agaagtatat atactagaaa gtgtgcttta aaattttgtt actttaattt tgtctccact      300
tcttttctcc tatgataggt tgtatcaaat tgggtcctcc gacttgggcc agaaggcctc      360
acacaatata agagtatccc taacttcctt ttatcttttc agctatcaat acgagacttt      420
ctggtattca tgttcctaga ttacctgtaa caaaatctgg taatagttga gtcggaaatc      480
gcttattccc actctgaaaa tcaatgtttt catatcccat tctattgtaa tgactcccca      540
tttcaggcct acttcccaag tcattagaaa ggtaattttg ttggctcact ggcatggcta      600
ggttttcaga aggaggaagt cctaaagtaa gagagacacc attatttcca tgaaaattcg      660
cggtgatttg ttgatcatga ggatcaaacc ttccaaaatc tcccatcgcg tatgctgcca      720
ttaaaggatt agtaaaccct ttatttgatg attctctagc tttggcttcc atgtcaacag      780
atgaaagaat actacttgga gaaaacttgt gcatgtcatt tctttgcttt ttcgcgttgt      840
tttcaatatg atcaacagta gtagtagtag tattatccat gttgaatgaa ccaaggaagg      900
agaaattgtg agcatgatga agtgaagcac ctgcagtagg ggaagttgaa atagttgagg      960
tagaaatttc tgcttgagta gtagtaatac catcttgtaa taagctgcta gtaataattg     1020
gatgtttctc ttcatttgga gcctctttgt ttttgttatc tcctgaagta ttagtactgt     1080
tttgttcttg attcttcact tcttccaagt acatttcttc taccattggc ttccataatc     1140
gaactcgagc atttatgaac cagttagaga cctgcatttt catatatatt aagaattttt     1200
ttataaagaa aagaaaggaa ttaatccaag aattatagta aatgtgtgt ctaagaacct     1260 ggctccttgt tagccccgtt tgcttagcaa gcatgatttt gtctgaatcc tttgggtaac     1320
tgcaatataa aaatatatta agaaaaaaaa aattatagtt aaaaacatac tcctatatta     1380
gagaagaatg ggcgaattca gaatttagaa taataatgtg atcttattat atacatgaac     1440 atatttatt ttttgtgtgt atgcatatat agtttgagtt aaaagtaagt gtcttttaa     1500 ccgtccaaac gaaagtttca aaataactgg cgttgctcta aaaatcactt aatttgttcc     1560
taatggatgg acatgttaaa accatataaa agacacttag taaaatatag gacgacaggc     1620
gtatatatga cgcaaaaatt ggttagaata atcaattttc tatctactac tccgtagata     1680
tttttcacat tgttaaattt ttcaaagaaa taaatagttt aggagtactc acggatgaag     1740
aaaatgctcg aaaagccaag cacgaaggac agagacagct ctttcaggta aacctctttg     1800
gggtctccaa gcatttggtt gcatcattcc tagctgttgc agcgcgcgtt gttgccttag     1860
atgatggtcc acaaatttga gtcttgagcc ttcgattttc cctactaagc cttcctcttc     1920
```

-continued

```
acctaaactc ttgctcgtcg cctttacttg ctcagcaatt gcatcct tta ggcatctgaa    1980 ttgcttcgaa attgcatgca aagctaattg agtgtatgat ttggctgaac caattcctgc    2040
tacttgctca aatgatgata caattatttg catttggtga tggtactgtc tgtacctttg    2100
ctccacctga acaaaaaaaa gggagtaata ttaaactttt accagtctgt cgttttacaa    2160
catgaagtta tcttatgttg gctactattg aaattaaaga attttatttc agttaaaaga    2220
tcatatatat atatatatat atattccaag tgagaaataa attgagtagt atattttgca    2280
aaattttgta aaccaacgaa tttttgagag tcattagatt gaggacacat ctgagtggac    2340
attatgcgtg gtgtaaaaaa ggtgaataag agatagtggt ttgaattttg gtgcagcgga    2400
agacatttca ggttcgtagc taactttggt gtattatctt tatagcttta gttggacccg    2460
cagaagaaaa tttaagagcc acacattgtc agtttgtttt aatatcaacg tacgtgattg    2520
gtctcttgtt cttcaactaa ttaacaaaac ctgtacattt catttaccaa ctactattgt    2580
tgcaaacata tataaatcaa cagtttcatc cattcaattt tttatgagaa aaattacagt    2640
tttgaatcat ttgaaaataa aattttaaat atatatgtcg aattcagtag ttttagtgtt    2700
aagaatccga aattcataga ctcaaaattc aggatcatac ctcttcaagc atggcaagaa    2760
gcttggcttt tttcatttga agttcttgtc tttgagcagt tgtaagctca atagcaactt    2820 cattttctg cctgctgcta ctttcaccac caccaccacc accagaacta ttagtgttga    2880
catcactagc caaaggcatt gaattatcct tcttttgatc atctcctttg atgcttttc    2940 caacaatatt aacaacttca tcaagaagct cttgtgcagc tttcagatac ttagagccta    3000
aaaccatgtt gctagaactt ccatctaatg ttcctctaat agtaacatta tttgtccttg    3060
gtgatgagga tgaaatattg ttattgaaac taatttgctg ttgttgctga ggagaaaggc    3120
ttagagatag accgccttgc tgttgttgct gctgctgtcg gtgttgtggt gtcggaatcg    3180
gcctctgaaa cgccaattga gacgccaagt ccgtggtgat cccgccacat gacgtggcag    3240 aaaccccgt cgacgatggt actatcacct gctgagattg atcttggttg ttccacatac    3300
gctgtaaaag tccatgatga ttgatctgat cgtgcaaact tactgccgga agaggcacac    3360
cgacaaagtg ctgctgttgc agcggcgcgt gttgtatatt cgcatggcaa agcgcgttgc    3420
ttcctgctgg tgaagaattc aggaaaagta actgctgctg ctgctgtgtg tcagaagtag    3480
tgtagccttg catataattg ttagggttca tcaaataaag cgtctgaata ttattattat    3540
tactactatt cccatgatta tgatgttgtt gatgatcagc ttgtatatta ttatccgagg    3600
ttccttgata gtacatatct gcaaaaaaaa atctttcttc ttcgaatttc tccttttatc    3660
tacaacagta cctgtaaaca gaaagtaaca aaggagaaaa ggcttcaaat aagtccacac    3720
aaacattttt ataagtaaac ggaagggaat tctttatagt gaaaaattaa attttgttta    3780
cagagatctt caactataaa taaaaaaaac aggaaaatga tataaaagaa agagaaagag    3840
atgaaaggag ctttagcaaa aaaatcagtc actcacacat acacacatgt aactaactgt    3900
ctatcttcgg gtggtagctc tctaagcttt gagaagttgc cttcttgtca gactgatcta    3960
tatttttctc tctgcattct catctcttca accacaaaaa ggaaatatga ataaa        4015
```

In one embodiment, the further nucleic acid molecule comprises a nucleotide sequence of SEQ ID NO:7 or a nucleic acid molecule that is at least about 95%, 96%, 97%, 98%, or 99% identical to the nucleotide sequence of SEQ ID NO:8. Alternatively, the further nucleic acid molecule comprises a nucleotide sequence capable of expressing active and/or functional StBEL5 to enhance the expression of StBEL5. A description of enhancing the expression of StBEL5 is provided infra.

Another aspect of the present invention is directed to a nucleic acid construct comprising a first nucleic acid molecule comprising a nucleotide sequence configured to silence or reduce expression of StBEL29 and variants thereof; a 5' DNA promoter sequence; and a 3' terminator sequence, where the first nucleic acid molecule, the promoter sequence, and the terminator sequence are operatively coupled to permit transcription of the first nucleic acid molecule.

According to one embodiment, the nucleic acid construct of the present invention comprises DNA heterologous to the first nucleic acid molecule. In one particular embodiment, the DNA heterologous to the first nucleic acid molecule is the 5' DNA promoter sequence.

In one embodiment, the first nucleic acid molecule comprising a nucleotide sequence configured to silence or reduce expression of StBEL29 has a nucleotide sequence of SEQ ID NO:6.

Other nucleic acid molecules may also be used as the first nucleic acid molecule comprising a nucleotide sequence configured to silence or reduce expression of StBEL29. For example, in certain embodiments, the second nucleic acid molecule has a nucleotide sequence that is at least about 95%, 96%, 97%, 98%, or 99% identical to the nucleotide sequence of SEQ ID NO:6.

By way of other examples, the first nucleic acid molecule has a nucleotide sequence that is at least about 70%, 75%, 80%, 85%, 90%, 91%, 92%, 93%, or 94% identical to the nucleotide sequence of SEQ ID NO:6.

In certain embodiments, the first nucleic acid molecule comprises at least 20, 21, 22, 23, 24, 25, 26, 27, 28, 29, 30, 35, 40, 45, 50, 55, 60, 65, 70, 75, 80, 85, 90, 95, 100, 125, 150, 175, 200, 225, 250, 275, 300, 325, 350, 375, or 400 contiguous bp of SEQ ID NO:6.

In certain embodiments, the first nucleic acid molecule comprises at least 20, 21, 22, 23, 24, 25, 26, 27, 28, 29, 30, 35, 40, 45, 50, 55, 60, 65, 70, 75, 80, 85, 90, 95, 100, 125, 150, 175, 200, 225, 250, 275, 300, 325, 350, 375, or 400 contiguous by of SEQ ID NO:5 which are less than 70%, 65%, 60%, 55%, 50%, 45%, 40%, 35%, 30%, 25%, 20%, 15%, 10%, 5%, or 1% identical to any portion of SEQ ID NO:8, where the portion of SEQ ID NO:8 has the same length as the first nucleic acid molecule.

According to this embodiment, one can silence or reduce expression of StBEL29 without silencing or reducing the expression of StBEL5.

In yet another embodiment of this aspect of the present invention, the nucleic acid construct further comprises a further nucleic acid molecule comprising a nucleotide sequence configured to enhance the expression of StBEL5 and variants thereof.

In one embodiment, the further nucleic acid molecule comprises a nucleotide sequence of SEQ ID NO:7 or a nucleic acid molecule that is at least about 95%, 96%, 97%, 98%, or 99% identical to the nucleotide sequence of SEQ ID NO:5. Alternatively, the further nucleic acid molecule comprises a nucleotide sequence capable of expressing active and/or functional StBEL5 to enhance the expression of StBEL5. A description of enhancing the expression of StBEL5 is provided infra.

Methods for identifying nucleic acid molecules capable of silencing or reducing expression of genes and/or related RNA molecules are well known in the art and are discussed in more detail infra.

As discussed supra, the nucleic acid constructs of the present invention comprise, in one embodiment, one or more nucleic acid molecules comprising a nucleotide sequence configured to silence or reduce expression of mRNA molecules and/or genes. In some embodiments, the nucleic acid constructs include a nucleic acid molecule comprising a nucleotide sequence configured to enhance expression of mRNA molecules and/or genes.

General strategies for silencing or reducing expression and enhancing expression are known in the art. Up-regulation, down-regulation, ectopic expression, gene editing, or gene silencing are well known.

Silencing or reducing gene expression means the interruption or suppression of the expression of a gene at the level of transcription or translation. In the present invention, silencing of StBEL gene expression may be carried out, according to one embodiment, by a nucleic acid molecule of the construct containing a dominant mutation and encoding a non-functional StBEL, resulting in suppression or interference of endogenous mRNA encoding the StBEL or variant thereof.

In another embodiment, the nucleic acid construct results in interference of StBEL gene expression by sense or co-suppression in which the nucleic acid molecule of the construct is in a sense (5'→3') orientation. Co-suppression has been observed and reported in many plant species and may be subject to a transgene dosage effect or, in another model, an interaction of endogenous and transgene transcripts that results in aberrant mRNAs (Senior, "Uses of Plant Gene Silencing," *Biotechnology and Genetic Engineering Reviews* 15:79-119 (1998); Waterhouse et al., "Exploring Plant Genomes by RNA-Induced Gene Silencing," *Nature Review: Genetics* 4:29-38 (2003), which are hereby incorporated by reference in their entirety). A construct with the nucleic acid molecule in the sense orientation may also give sequence specificity to RNA silencing when inserted into a vector along with a construct of both sense and antisense nucleic acid orientations as described infra (Wesley et al., "Construct Design for Efficient, Effective and High-Throughput Gene Silencing in Plants," *Plant Journal* 27(6):581-590 (2001), which is hereby incorporated by reference in its entirety).

In yet another embodiment, the nucleic acid construct results in interference of StBEL gene expression by the use of antisense suppression in which the nucleic acid molecule of the construct is an antisense (3'→5') orientation. The use of antisense RNA to down-regulate the expression of specific plant genes is well known (van der Krol et al., "An Anti-sense Chalcone Synthase Gene in Transgenic Plants Inhibits Flower Pigmentation," *Nature* 333:866-869 (1988) and Smith et al., "Antisense RNA Inhibition of Polygalacturonase Gene Expression in Transgenic Tomatoes," *Nature* 334:724-726 (1988), which are hereby incorporated by reference in their entirety). Antisense nucleic acids are DNA or RNA molecules that are complementary to at least a portion of a specific mRNA molecule (Weintraub, "Anti-sense RNA and DNA," *Scientific American* 262:40 (1990), which is hereby incorporated by reference in its entirety). In the target cell, the antisense nucleic acids hybridize to a target nucleic acid and interfere with transcription, and/or RNA processing, transport, translation, and/or stability. The overall effect of such interference with the target nucleic acid function is the disruption of protein expression (Baulcombe, "Mechanisms of Pathogen-Derived Resistance to Viruses in Transgenic Plants," *Plant Cell* 8:1833-44 (1996); Dougherty, et al., "Transgenes and Gene Suppression: Telling us Something New?," *Current Opinion in Cell Biology* 7:399-05 (1995); Lomonossoff, "Pathogen-Derived Resistance to Plant Viruses," *Ann. Rev. Phytopathol.* 33:323-43 (1995), which are hereby incorporated by reference in their entirety). Accordingly, one embodiment involves a nucleic acid construct which contains the StBEL gene encoding nucleic acid molecule being inserted into the construct in antisense orientation.

Interfering with endogenous StBEL gene expression may involve an RNA-based form of gene-silencing known as RNA interference ("RNAi") (also known as siRNA for short, interfering RNAs). RNAi is a form of post-transcriptional gene silencing ("PTGS"). PTGS is the silencing of an endogenous gene caused by the introduction of a homologous double-stranded RNA ("dsRNA"), transgene, or virus. In PTGS, the transcript of the silenced gene is synthesized, but does not accumulate because it is degraded. RNAi is a specific form of PTGS, in which the gene silencing is induced by the direct introduction of dsRNA. Numerous reports have been published on critical advances in the understanding of the biochemistry and genetics of both gene silencing and RNAi (Matzke et al., "RNA-Based Silencing Strategies in Plants," *Curr. Opin. Genet. Dev.* 11(2):221-227 (2001), Hammond et al., "Post-Transcriptional Gene Silencing by Double-Stranded RNA," *Nature Rev. Gen.* 2:110-119 (Abstract) (2001); Hamilton et al., "A Species of Small Antisense RNA in Posttranscriptional Gene Silencing in Plants," *Science* 286:950-952 (Abstract) (1999); Hammond et al., "An RNA-Directed Nuclease Mediates Post-Transcriptional Gene Silencing in *Drosophila* Cells," *Nature* 404:293-298 (2000); Hutvagner et al., "RNAi: Nature Abhors a Double-Strand," *Curr. Opin. Genetics & Development* 12:225-232 (2002), which are hereby incorporated by reference in their entirety).

In iRNA, the introduction of double stranded RNA (dsRNA) into animal or plant cells leads to the destruction of the endogenous, homologous mRNA, phenocopying a null mutant for that specific gene. In siRNA, the dsRNA is processed to short interfering molecules of 21-, 22- or 23-nucleotide RNAs (siRNA), which are also called "guide RAs," (Hammond et al., "Post-Transcriptional Gene Silencing by Double-Stranded RNA," *Nature Rev. Gen.* 2:110-119 (Abstract) (2001); Sharp, "RNA Interference-2001," *Genes Dev.* 15:485-490 (2001); Hutvagner et al., "RNAi: Nature Abhors a Double-Strand," *Curr. Opin. Genetics & Development* 12:225-232 (2002), which are hereby incorporated by reference in their entirety) in vivo by the Dicer enzyme, a member of the RNAse III-family of dsRNA-specific ribonucleases (Hutvagner et al., "RNAi: Nature Abhors a Double-Strand," *Curr. Opin. Genetics & Development* 12:225-232 (2002); Bernstein et al., "Role for a Bidentate Ribonuclease in the Initiation Step of RNA Interference," *Nature* 409:363-366 (2001); Tuschl, "RNA Interference and Small Interfering RNAs," *Chembiochem* 2:239-245 (2001); Zamore et al., "RNAi: Double Stranded RNA Directs the ATP-Dependent Cleavage of mRNA at 21 to 23 Nucleotide Intervals," *Cell* 101:25-3 (2000); U.S. Pat. No. 6,737,512 to Wu et al., which are hereby incorporated by reference in their entirety). Successive cleavage events degrade the RNA to 19-21 bp duplexes, each with 2-nucleotide 3' overhangs (Hutvagner et al., "RNAi: Nature Abhors a Double-Strand," *Curr. Opin. Genetics & Development* 12:225-232 (2002); Bernstein et al., "Role for a Bidentate Ribonuclease in the Initiation Step of RNA Interference," *Nature* 409:363-366 (2001), which are hereby incorporated by reference in their entirety). The siRNAs are incorporated into an effector known as the RNA-induced silencing complex (RISC), which targets the homologous endogenous transcript by base pairing interactions and cleaves the mRNA approximately 12 nucleotides from the 3' terminus of the siRNA (Hammond et al., "Post-Transcriptional Gene Silencing by Double-Stranded RNA," *Nature Rev. Gen.* 2:110-119 (Abstract) (2001); Sharp, "RNA Interference-2001," *Genes Dev.* 15:485-490 (2001); Hutvagner et al., "RNAi: Nature Abhors a Double-Strand," *Curr. Opin. Genetics & Development* 12:225-232 (2002); Nykanen et al., "ATP Requirements and Small Interfering RNA Structure in the RNA Interference Pathway," *Cell* 107:309-321 (2001), which are hereby incorporated by reference in their entirety).

There are several methods for preparing siRNA, including chemical synthesis, in vitro transcription, siRNA expression vectors, and PCR expression cassettes. In one embodiment, dsRNA for the nucleic acid molecule used in the present invention can be generated by transcription in vivo. This involves modifying the nucleic acid molecule for the production of dsRNA, inserting the modified nucleic acid molecule into a suitable expression vector having the appropriate 5' and 3' regulatory nucleotide sequences operably linked for transcription and translation, as described supra, and introducing the expression vector having the modified nucleic acid molecule into a suitable host or subject. Using siRNA for gene silencing is a rapidly evolving tool in molecular biology, and guidelines are available in the literature for designing highly effective siRNA targets and making antisense nucleic acid constructs for inhibiting endogenous protein (U.S. Pat. No. 6,737,512 to Wu et al.; Brown et al., "RNA Interference in Mammalian Cell Culture: Design, Execution, and Analysis of the siRNA Effect," *Ambion TechNotes* 9(1):3-5(2002); Sui et al., "A DNA Vector-Based RNAi Technology to Suppress Gene Expression in Mammalian Cells," *Proc. Nat'l. Acad. Sci. USA* 99(8):5515-5520 (2002); Yu et al., "RNA Interference by Expression of Short-Interfering RNAs and Hairpin RNAs in Mammalian Cells," *Proc. Nat'l. Acad. Sci. U.S.A.* 99(9): 6047-6052 (2002); Paul et al., "Effective Expression of Small Interfering RNA in Human Cells," *Nature Biotechnology* 20:505-508 (2002); Brummelkamp et al., "A System for Stable Expression of Short Interfering RNAs in Mammalian Cells," *Science* 296:550-553 (2002), which are hereby incorporated by reference in their entirety). There are also commercially available sources for custom-made siRNAs.

As noted supra, interference of StBEL gene expression is also achieved in the present invention by the generation of double-stranded RNA ("dsRNA") through the use of inverted-repeats, segments of gene-specific sequences oriented in both sense and antisense orientations. In one embodiment, sequences in the sense and antisense orientations are linked by a third segment, and inserted into a suitable expression vector having the appropriate 5' and 3' regulatory nucleotide sequences operably linked for transcription. The expression vector having the modified nucleic acid molecule is then inserted into a suitable host cell or subject. In the present invention, the third segment linking the two segments of sense and antisense orientation may be any nucleotide sequence such as a fragment of the β-glucuronidase ("GUS") gene. In another embodiment, a functional (splicing) intron of the StBEL gene may be used for the third (linking) segment or, in yet another embodiment of the present invention, other nucleotide sequences without complementary components in the StBEL gene may be used to link the two segments of sense and antisense orientation (Chuang et al., "Specific and Heritable Genetic Interference by Double-Stranded RNA in *Arabidopsis thaliana*," *Proc. Nat'l. Academy of Sciences USA* 97(9):4985-4990 (2000); Smith et al., "Total Silencing by Intron-Spliced Hairpin RNAs," *Nature* 407:319-320 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6): 581-590 (2001), which are hereby incorporated by reference in their entirety). In any of the embodiments with inverted repeats of the StBEL gene, the sense and antisense segments may be oriented either head-to-head or tail-to-tail in the construct.

In another embodiment, silencing or reducing expression of an StBEL using a nucleic acid construct of the present invention involves using hairpin RNA ("hpRNA"), which may also be characterized as dsRNA. This involves RNA hybridizing with itself to form a hairpin structure that comprises a single-stranded loop region and a base-paired stem. Though a linker may be used between the inverted repeat segments of sense and antisense sequences to generate hairpin or double-stranded RNA, the use of intron-free hpRNA can also be used to achieve silencing of StBEL gene expression.

Alternatively, in another embodiment, a plant may be transformed with constructs encoding both sense and antisense orientation molecules having separate promoters and no third segment linking the sense and antisense sequences (Chuang et al., "Specific and Heritable Genetic Interference by Double-Stranded RNA in *Arabidopsis thaliana*," *Proc. Nat'l. Academy of Sciences USA* 97(9):4985-4990 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety).

Other means of altering gene expression, including silencing, are being developed and are also contemplated. For example, epigenetics is the study of heritable changes in gene expression or cellular phenotype caused by mechanisms other than changes in the underlying DNA sequence. Epigenetics refers to functionally relevant modifications to the genome that do not involve a change in the nucleotide sequence. Examples of such changes are DNA methylation and histone deacetylation, both of which serve to suppress gene expression without altering the sequence of the silenced genes.

Enhancing gene expression means increasing the natural or normal expression of a gene at the level of transcription or translation. In the present invention, enhancement of StBEL gene expression may be carried out, according to one embodiment, by a nucleic acid molecule of the construct containing a functional StBEL, resulting in increased expression relative to endogenous StBEL mRNA levels.

Thus, the constructs of the present invention also include an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known in the art. Virtually any 3' regulatory region known to be operable in the host cell of choice would suffice for proper expression of the coding sequence of the nucleic acid designed to enhance expression.

In one embodiment, the nucleic acid construct of the present invention has a nucleic acid incorporated into an appropriate vector to enhance expression, and is positioned in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, as described infra, may be used.

A further aspect of the present invention is directed to an expression vector comprising a nucleic acid construct of the present invention.

Another aspect of the present invention is directed to a host cell transformed with a nucleic acid construct of the present invention.

A further aspect of the present invention is directed to a transgenic plant seed transformed with a nucleic acid construct of the present invention.

Another aspect of the present invention is directed to a transgenic plant transformed with a nucleic acid construct of the present invention, where the plant has increased tuber yield compared to a plant not transformed with the nucleic acid construct.

A further aspect of the present invention relates to a transgenic cell of a plant of the present invention.

Another aspect of the present invention relates to a transgenic plant seed produced from a plant of the present invention.

The nucleotide sequences used in the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pG-Cha, p35S-Cha, pBR322, pBR325, pACYC177, pACYC1084, pUC8, pUC9, pUC18, pUC19, pLG339, pR290, pKC37, pKC101, SV 40, pBluescript II SK +/− or KS +/−(see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, N.Y.:Cold Spring Harbor Press (1989), and Ausubel et al., *Current Protocols in Molecular Biology*, New York, N.Y.:John Wiley & Sons (1989), which are hereby incorporated by reference in their entirety.

In preparing a nucleic acid construct for expression, the various nucleic acid sequences may normally be inserted or substituted into a bacterial plasmid. Any convenient plasmid may be employed, which will be characterized, for example and without limitation, by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall is characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Mol. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used. Native promoters can also be used.

A constitutive promoter is a promoter that directs expression of a gene throughout the development and life of an organism. Examples of some constitutive promoters that are widely used for inducing expression of transgenes include the nopaline synthase (NOS) gene promoter, from *Agrobacterium tumefaciens* (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); McNellis et al., "Glucocorticoid-Inducible Expression of a Bacterial Avirulence Gene in Transgenic *Arabidopsis* Induces Hypersensitive Cell Death," *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known in the field (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the *Chrysanthemum* UEP1 Promoter and Comparative Expression in Florets and Leaves of *Dendranthema grandiflora*," *Transgenic Res.* 11:437-445(2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci. USA* 99:1092-1097 (2002), which is hereby incorporated by reference in its entirety), and tuber/storage organ-specific (Visser et al., "Expression of a Chimaeric Granule-Bound Starch Synthase-GUS gene in transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter. In certain embodiments, the DNA promoter sequence is a constitutive, inducible, developmentally-regulated, organelle-specific, tissue-specific, cell-specific, seed (or grain)-specific, or germination-specific promoter.

The nucleic acid constructs of the present invention may also include an operable 3' regulatory region, selected from among those which are capable of providing correct transcription termination and polyadenylation of mRNA for expression in the host cell of choice, operably linked to a modified trait nucleic acid molecule of the present invention. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would be suitable for use in conjunction with the present invention.

As discussed supra, components of nucleic acid constructs according to the present invention may be heterologous. A polynucleotide sequence is "heterologous to" an organism or a second polynucleotide sequence if it is synthetic or originates from a foreign species or, if from the same species, is modified from its original form. For example, a promoter operably linked to a heterologous coding sequence (or vice versa) refers to a coding sequence from a species different from that from which the promoter was derived or, if from the same species, a coding sequence which is not naturally associated with the promoter (e.g., a genetically engineered coding sequence or an allele from a different ecotype or variety).

The different components described above can be ligated together to produce the expression systems which contain the nucleic acid constructs used in the present invention, using well known molecular cloning techniques as described in Sambrook et al., *Molecular Cloning: A Laboratory Manual*, Second Edition Cold Spring Harbor, N.Y.:Cold Spring Harbor Press (1989), and Ausubel et al. *Current Protocols in Molecular Biology*, New York, N.Y.:John Wiley & Sons (1989), which are hereby incorporated by reference in their entirety.

Once the nucleic acid construct has been prepared, it is ready to be incorporated into a host cell. Basically, this method is carried out by transforming a host cell with the nucleic acid construct under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Spring Harbor Laboratory, Cold Spring Harbor, N.Y. (1989), which is hereby incorporated by reference in its entirety. Suitable host cells are plant cells. Suitable host cells also include bacterial cells. Methods of transformation may result in transient or stable expression of the nucleic acid under control of the promoter. In one embodiment, the nucleic acid construct of the present invention is stably inserted into the genome of the recombinant plant cell as a result of the transformation, although transient expression can serve an important purpose, particularly when the plant under investigation is slow-growing.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 µm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing a nucleic acid construct into plant cells is to infect a plant cell with *Agrobacterium tumefaciens* or *Agrobacterium rhizogenes* previously transformed with the nucleic acid construct. As described supra, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., "Liposome-mediated Delivery of Tobacco Mosaic Virus RNA Into Tobacco Protoplasts: A Sensitive Assay for Monitoring Liposome-protoplast Interactions," Proc. Natl. Acad. Sci. U.S.A. 79:1859-63 (1982), which is hereby incorporated by reference in its entirety). The nucleic acid molecule may also be introduced into the plant cells by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention.

Yet a further method for introduction is by use of known techniques for genome editing or alteration. Such techniques for targeted genomic insertion involve, for example, inducing a double stranded DNA break precisely at one or more targeted genetic loci followed by integration of a chosen transgene or nucleic acid molecule (or construct) during repair. Such techniques or systems include, for example, zinc finger nucleases ("ZFNs") (Urnov et al., "Genome Editing with Engineered Zinc Finger Nucleases," *Nat. Rev. Genet.* 11: 636-646 (2010), which is hereby incorporated by reference in its entirety), transcription activator-like effector nucleases ("TALENs") (Joung & Sander, "TALENs: A Widely Applicable Technology for Targeted Genome Editing," *Nat. Rev. Mol. Cell Biol.* 14: 49-55 (2013), which is hereby incorporated by reference in its entirety), clustered regularly interspaced short palindromic repeat ("CRISPR")-associated endonucleases (e.g., CRISPR/CRISPR-associated ("Cas") 9 systems) (Wiedenheft et al., "RNA-Guided Genetic Silencing Systems in Bacteria and Archaea," *Nat.* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7): 397-405 (2013), each of which is hereby incorporated by reference in its entirety).

In certain embodiments, transformation described herein is carried out by *Agrobacterium*-mediated transformation, whisker method transformation, vacuum infiltration, biolistic transformation, electroporation, micro-injection, polyethylene-mediated transformation, or laser-beam transformation.

After transformation, the transformed plant cells must be regenerated. Plant regeneration from cultured protoplasts is described in Evans et al., *Handbook of Plant Cell Cultures*, Vol. 1, New York, New York: MacMillan Publishing Co. (1983); Vasil, ed., *Cell Culture and Somatic Cell Genetics of Plants*, Vol. I (1984) and Vol. III (1986), Orlando: Acad. Press; and Fitch et al., "Somatic Embryogenesis and Plant Regeneration from Immature Zygotic Embryos of *Papaya* (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

In one embodiment, transformed cells are first identified using a selection marker simultaneously introduced into the host cells along with the nucleic acid construct of the present invention. Suitable selection markers include, without limitation, markers encoding for antibiotic resistance, such as the neomycin phosphotransferae II ("nptII") gene which confers kanamycin resistance (Fraley et al., "Expression of Bacterial Genes in Plant Cells," *Proc. Natl. Acad. Sci. U.S.A.* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., "Vectors Containing a Prokaryotic Dihydrofolate Reductase Gene Transform *Drosophila* Cells to Methotrexate-resistance," *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, New York:Cold Spring Harbor Press (1989), which is hereby incorporated by reference in its entirety).

After the fusion gene containing a nucleic acid construct is stably incorporated in transgenic plants, the transgene can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds are recovered from the transgenic plants. These seeds can then be planted in the soil and cultivated using conventional procedures to produce transgenic plants.

Plants of the present invention (i.e., having a nucleic acid construct of the present invention, as discussed supra, or one or more mutations, as discussed infra) have increased tuber yield.

In certain embodiments, the transgenic plant transformed with the nucleic acid construct or plant grown from transgenic seed, has increased tuber yield compared to a plant not transformed with the nucleic acid construct. In some embodiments the yield increase is by at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, or 300% compared to a plant not transformed with the nucleic acid construct.

In some embodiments, the overall shoot fresh weight of the transgenic plant transformed with the nucleic acid construct or plant grown from transgenic seed is at least 50%, 55%, 60%, 65%, 70%, 75%, 80%, 85%, 90%, 95%, 100% compared to a plant not transformed with the nucleic acid construct.

In one embodiment, the transgenic plant comprises an expression level of StBEL11 less than 95%, 90%, 85%, 80%, 75%, 70%, 65%, 60%, 55%, 50%, 45%, 40%, 35%, 30%, 25%, 20%, 15%, 10%, 5%, or 1% compared to a plant not transformed with the nucleic acid construct.

In some embodiments, the transgenic plant comprises an expression level of StBEL29 less than 95%, 90%, 85%, 80%, 75%, 70%, 65%, 60%, 55%, 50%, 45%, 40%, 35%, 30%, 25%, 20%, 15%, 10%, 5%, or 1% compared to a plant not transformed with the nucleic acid construct.

In some embodiments, the transgenic plant comprises an expression level of StBEL11 and StBEL29 less than 95%, 90%, 85%, 80%, 75%, 70%, 65%, 60%, 55%, 50%, 45%, 40%, 35%, 30%, 25%, 20%, 15%, 10%, 5%, or 1% compared to a plant not transformed with the nucleic acid construct.

In some embodiments, the transgenic plant comprises an expression level of StBEL5 greater than 1%, 5%, 10%, 15%, 20%, 25%, 30%, 35%, 40%, 45%, 50%, 55%, 60%, 5%, 70%, 75%, 80%, 85%, 90%, 95%, 100%, 125%, 150%, 175%, or 200% compared to a plant not transformed with the nucleic acid construct.

In some embodiments, the transgenic plant comprises an expression level of StBEL11 and/or StBEL29 less than 95%, 90%, 85%, 80%, 75%, 70%, 65%, 60%, 55%, 50%, 45%, 40%, 35%, 30%, 25%, 20%, 15%, 10%, 5%, or 1% compared to a plant not transformed with the nucleic acid construct, and an expression level of StBEL5 greater than 1%, 5%, 10%, 15%, 20%, 25%, 30%, 35%, 40%, 45%, 50%, 55%, 60%, 5%, 70%, 75%, 80%, 85%, 90%, 95%, 100%, 125%, 150%, 175%, or 200% compared to a plant not transformed with the nucleic acid construct.

Expression level, as applied to BEL mRNAs, is defined herein as the level of transcription of the BEL gene. Expression levels may be quantified by any method known in the art. In one embodiment accumulation level of BEL is measured in leaves of a young tissue culture plant using RT-qPCR. In another embodiment, accumulation level of BEL is measured in stolons of a plant using RT-qPCR. In another embodiment, accumulation level of BEL is measured in both the leaves and stolon.

A person of ordinary skill in the art will understand that expression levels may be quantified at different developmental times or in different tissues or cells depending on the nature of the promoter driving gene expression (e.g. native, constitutive, inducible, developmentally-regulated, organelle-specific, tissue-specific, cell-specific, seed specific, or germination-specific).

In one embodiment, StBEL 11 and/or StBEL29 is driven by its natural promoter, and expression levels are measured first in leaves of a young tissue culture plant using RT-qPCR and subsequently in stolons of the plant using RT-qPCR.

In one embodiment, the transgenic plant is selected from the group consisting of potato, dahlia, caladium, Jerusalem artichoke (*Helianthus tuberosus*), yarn (*Dioscorea alta*), sweet potato (*Impomoea batatus*), cassava (*Manihot esculenta*), tuberous begonia, cyclamen, other *solanum* species (e.g., wild potato), sugar beet (*Beta vulgaris*), carrot (*Daucus carota*), and radish (*Raphanus sativus*).

In one embodiment, the transgenic plant is selected from the group consisting of *Solanum tuberosum* spp. andigena and *Solanum tuberosum* spp. *tuberosum*.

Another aspect of the present invention is directed to a method of increasing tuber yield in a plant. This method involves providing a transgenic plant or plant seed comprising a nucleic acid construct comprising one or more nucleic acid molecules configured to reduce or silence expression of (i) StBEL11 RNA and variants thereof, (ii) StBEL29 RNA and variants thereof, or (iii) both (i) and (ii); and growing the transgenic plant or plant grown from the transgenic plant seed under conditions effective to express the one or more nucleic acid molecules in said transgenic plant or said plant grown from the transgenic plant seed.

In one embodiment, a transgenic plant is provided.

In another embodiment, a transgenic seed is provided.

In a further embodiment, providing comprises transforming a non-transgenic plant or a non-transgenic plant seed with the nucleic acid construct to yield the transgenic plant or plant seed.

Providing a transgenic plant or plant seed may include transforming a non-transgenic plant or a non-transgenic plant seed with the nucleic acid construct to yield said transgenic plant or plant seed. Suitable methods of transformation are described supra.

Tuber yield as used herein can be measured as fresh weight of tubers per plant or dry weight of tubers per plant.

The increased tuber yield may be by any amount. For example, the increased tuber yield may be by about (or by at least about) 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, or 300% compared to a plant not transformed with the nucleic acid construct.

Increased tuber yield, as well as any other trait described herein (e.g., overall shoot fresh weight, etc.) in a plant as described herein may be determined in comparison to a control plant. The choice of suitable control plants is a routine part of an experimental setup and may include corresponding wild type plants, corresponding plants without the gene of interest (e.g., those not transformed with the subject nucleic acid molecule). The control plant is typically of the same plant species or even of the same variety as the plant to be assessed. The control plant may also be a nullizygote of the plant to be assessed. A "control plant" as used herein refers not only to whole plants, but also to plant parts, including inflorescence, seeds, and seed parts.

Yet another aspect of the present invention is directed to a potato plant comprising one or more mutations in one or both of StBEL11 and StBEL29, wherein said potato plant has increased tuber yield compared to the tuber yield of a wild type potato plant.

In one embodiment, the potato plant further comprising one or more mutations in StBEL5.

In one embodiment, the potato plant is non-transgenic. Accordingly, it is contemplated that mutations leading to increased tuber yield may be introduced via gene editing techniques or induced mutation techniques. Alternatively, naturally occurring mutations may be combined via traditional breeding to produce high tuber yield plants.

In one embodiment, the mutated potato plant is obtained by subjecting at least one cell of a potato plant to a chemical mutagenizing agent under conditions effective to yield at least one mutant plant cell containing an inactive or partially inactive StBEL gene or variant thereof. A suitable chemical mutagenizing agent can include, for example, ethylmethanesulfonate.

In another embodiment, the mutated potato plant is obtained by subjecting at least one cell of a potato plant to a radiation source under conditions effective to yield at least one mutant plant cell containing an StBEL gene or variant thereof with altered expression. Suitable radiation sources can include, for example, sources that are effective in producing ultraviolet rays, gamma rays, or fast neutrons.

In another embodiment, the mutated potato plant is obtained by inserting an inactivating nucleic acid molecule into the gene encoding the functional StBEL gene or its promoter under conditions effective to inactivate the gene. Suitable inactivating nucleic acid molecules can include, for example, a transposable element. Examples of such transposable elements include, but are not limited to, an Activator (Ac) transposon, a Dissociator (Ds) transposon, or a Mutator (Mu) transposon.

In yet another embodiment, the mutated potato plant is obtained by subjecting at least one cell of a potato plant to *Agrobacterium* transformation under conditions effective to insert an *Agrobacterium* T-DNA sequence into the gene, thereby inactivating the gene. Suitable *Agrobacterium* T-DNA sequences can include, for example, those sequences that are carried on a binary transformation vector of pAC106, pAC161, pGABI1, pADIS1, pCSA110, pDAP101, derivatives of pBIN19, or pCAMBIA plasmid series.

In yet another embodiment, the mutated potato plant is obtained by subjecting at least one cell of a potato plant to site-directed mutagenesis of the StBEL gene or its promoter under conditions effective to yield at least one mutant plant cell containing an StBEL gene with altered expression. See, e.g., Baker, "Gene-editing Nucleases," *Nature Methods* 9(1):23-26 (2012), which is hereby incorporated by reference in its entirety. The treating step may also involve subjecting the at least one cell of the potato plant to site-directed mutagenesis of the StBEL gene under conditions effective to yield at least one mutant plant cell containing a variant StBEL gene associated with increased tuber yield as described herein above. The various plants that can be used in this method are the same as those described supra with respect to the transgenic plants and mutant plants.

In yet another embodiment, the mutated potato plant is obtained by subjecting at least one cell of a potato plant to gene editing, as described supra, to yield at least one mutant plant cell containing a modified (or variant) sequence of the StBEL gene associated with tuber yield as described herein above. Propagating the at least one mutant plant cell into a mutant plant results in a mutant plant having an altered level of StBEL protein or variant thereof associated with tuber production as described herein above compared to that of the nonmutant plant and displays an altered (e.g., increased) tuber yield phenotype relative to a nonmutant plant at the levels or amounts discussed supra.

In one embodiment, the potato plant comprises a reduced expression level of StBEL11 compared to a wild type potato plant at the levels discussed supra.

In another embodiment, the expression level of StBEL11 is measured by quantifying accumulation levels of StBEL11 in leaves of a young tissue culture plant using RT-qPCR.

In a further embodiment, the potato plant comprises a reduced expression level of StBEL29 compared to a wild type potato plant at the levels discussed supra.

In one embodiment, the expression level of StBEL29 is measured by quantifying accumulation levels of StBEL11 in leaves of a young tissue culture plant using RT-qPCR, as discussed supra.

In one embodiment, the potato plant comprises a tuber yield at a level discussed supra.

In one embodiment, the potato plant comprises an increased expression level of StBEL5 compared to a wild type potato plant at the levels discussed supra.

The present invention is also directed to potato seed from the potato plants described herein.

EXAMPLES

Example 1—Cloning Strategies and Whole-Plant Transformation

Partial cDNA sequences of both StBEL11 (GenBank: AF406698, which is hereby incorporated by reference in its entirety) and StBEL29 (GenBank: AF406702, which is hereby incorporated by reference in its entirety) were obtained from NCBI. Putative upstream sequences were identified using the potato genome database (http://potato-.plantbiology.msu.edu). Genomic DNA from leaves of wild-type potato (*Solanum tuberosum* ssp. *andigena*) was isolated using DNeasy plant mini kit (QIAGEN). Upstream regulatory sequences of both StBEL11 and StBEL29 genes were isolated using the Universal Genome Walker kit (Clontech). Both these sequences were verified using the online potato genome database. Upstream sequences of 1678 bp for StBEL11 and 2151 bp for StBEL29 were isolated from the genomic DNA of *Solanum tuberosum* ssp. *andigena* through genome walking. The upstream sequences of both genes were amplified using gene-specific primers (Table 1) and were verified by sequencing. Both sequences were fused to the β-glucoronidase (GUS) gene and cloned into the binary vector pBI121 to generate the proStBEL11:GUS and proStBEL29:GUS constructs.

Figure 1A:
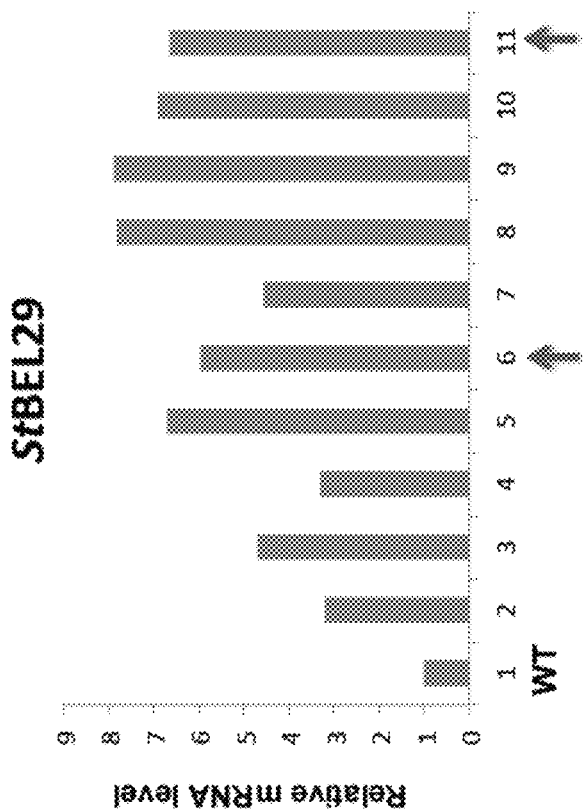
FIGS. 1A-1B depict the screening of StBEL11 (FIG. 1A) and StBEL29 (FIG. 1B) CaMV 35S transgenic overexpression lines using RT-qPCR off RNA from in vitro plantlets. GAPDH RNA was used as an internal control. The lines designated with arrows were used for phenotypic analysis. Values shown in the bar graphs are relative to wild-type andigena levels.
Figure 1B:
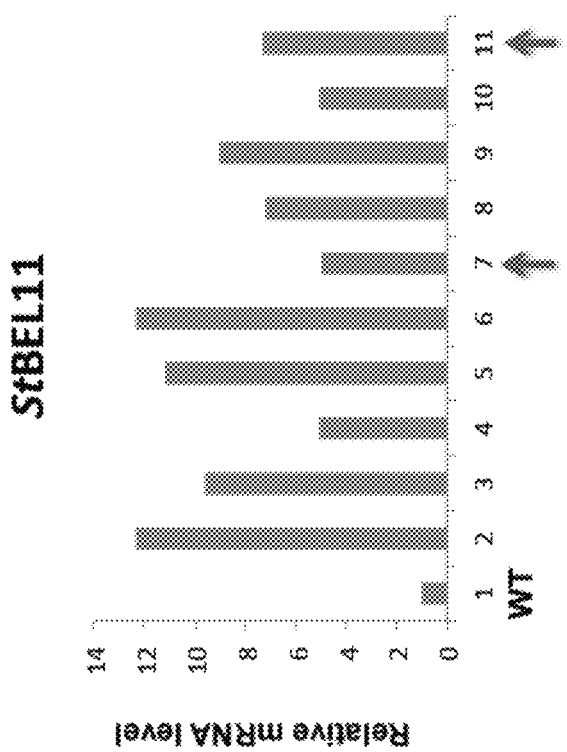
Figure 2A:
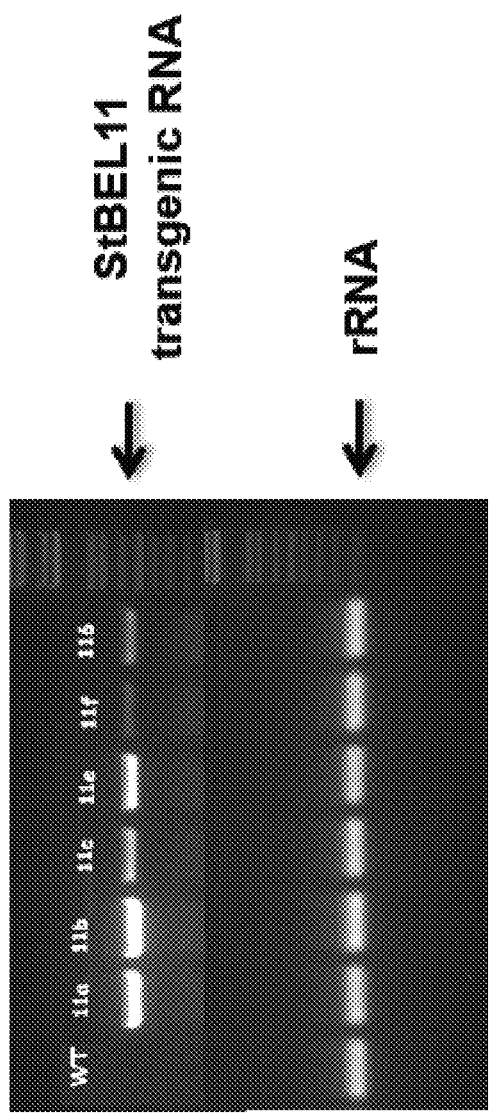
FIGS. 2A-2B depict the screening of GAS:StBEL11 and GAS:StBEL29 transgenic lines. RNA was extracted from transgenic in vitro plantlets and one-step RTPCR (FIG. 2A) or RT-qPCR (FIG. 2B) with GSPs were performed for StBEL11 and StBEL29, respectively. Only transgenic StBEL11 RNA was assayed in FIG. 2A. Values shown in FIG. 2B are relative to WT andigena levels. Lines 11a, b, c, and e (FIG. 2A) and StBEL29 lines 9 and 19 (FIG. 2B) were identified as high expressers with significant phenotypes and were used in subsequent experiments.
Figure 2B:
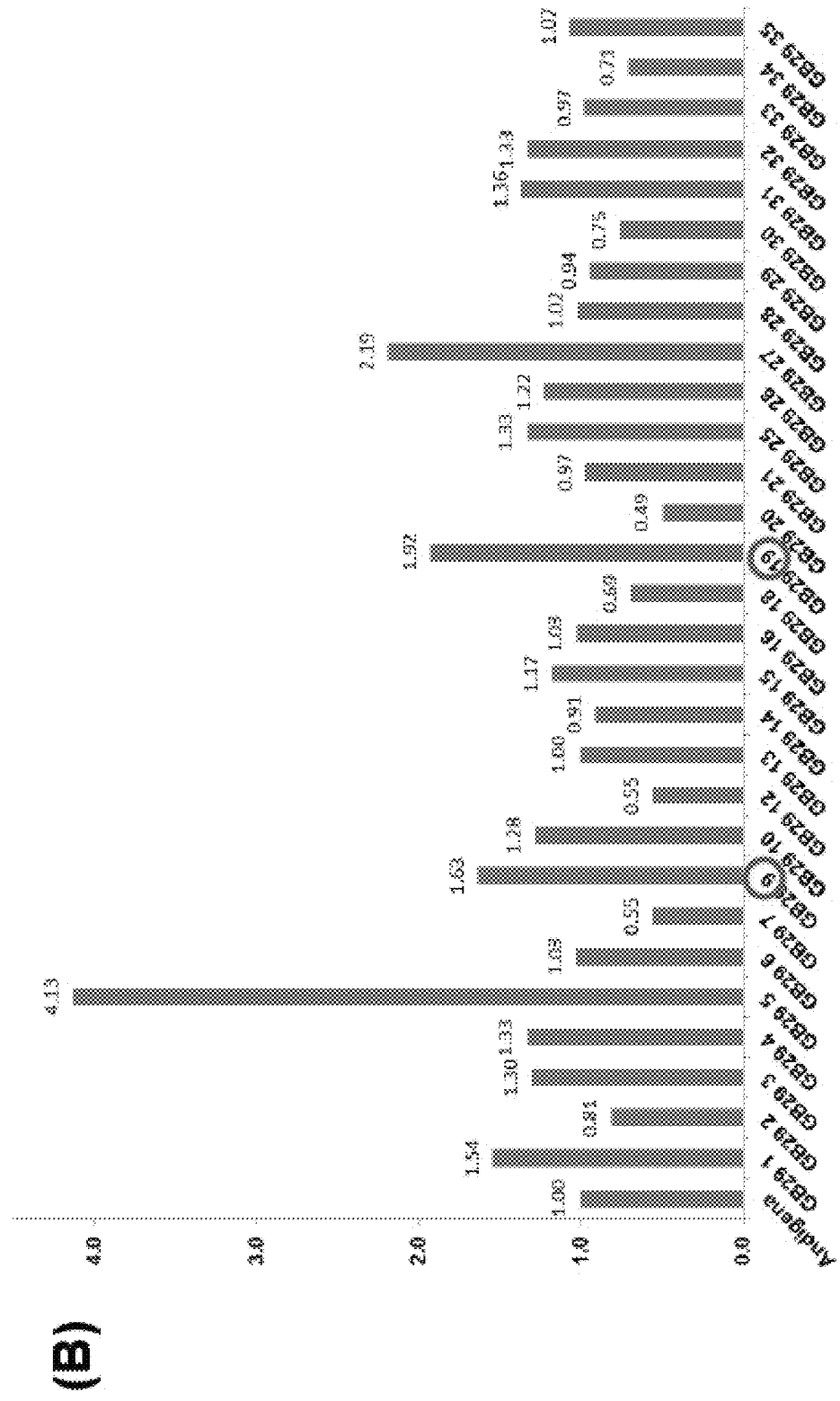
Figure 3A:
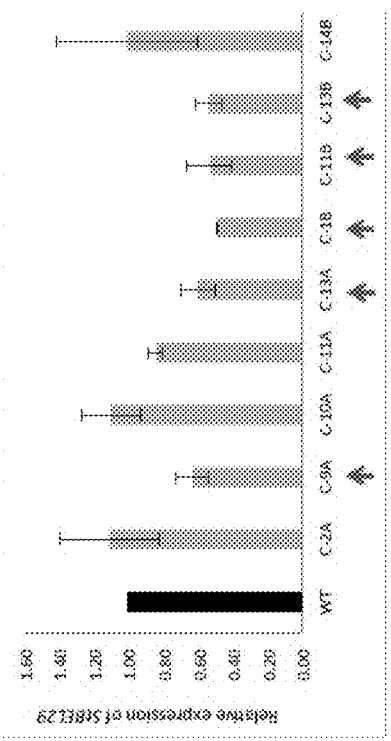
FIGS. 3A-3D show 35S:antisense RNA lines screened for StBEL11 or StBEL29 RNA from either leaves of one-month old soil-grown plants or stolons from 21 day short-day plants. Lines designated 11-1 (C-72), 11-2 (C-75), 29-1 (C-9A), and 29-2 (C-1B) were used for further analyses. RT-qPCR with gene-specific primers was used for the quantification. Each sample was measured in duplicate. Details of the transformation and screening protocols are described in the examples infra.
Figure 3B:
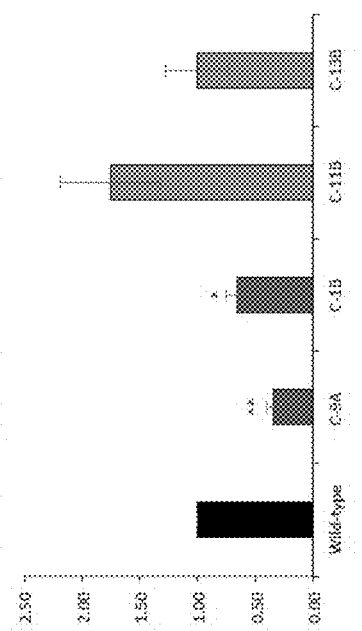
Figure 3C:
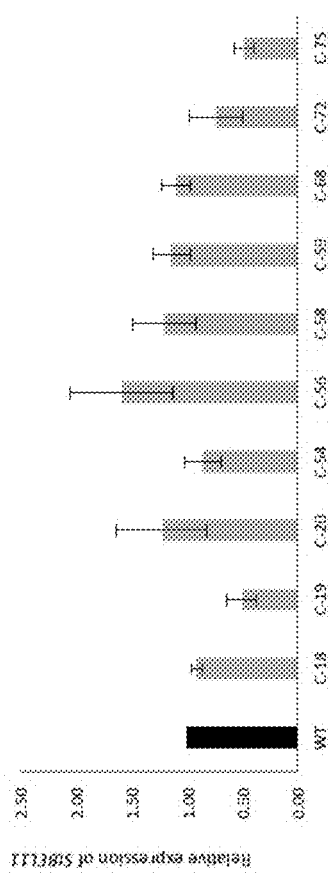
Figure 3D:
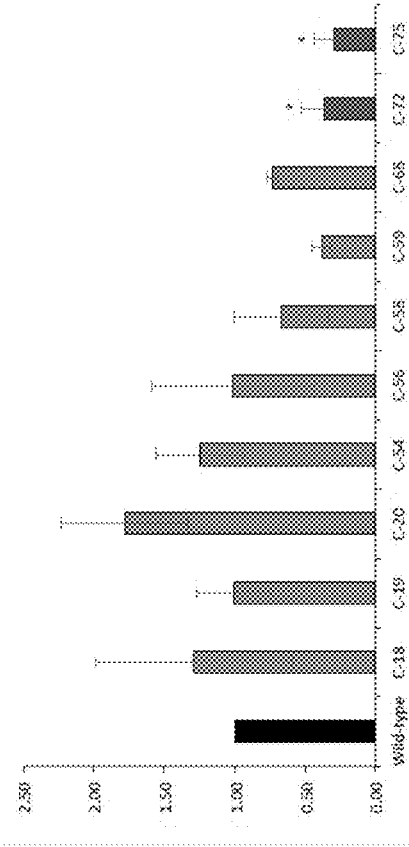

Full-length sequences of StBEL11 (2718 bp) (SEQ ID NO:2) and StBEL29 (2898 bp) (SEQ ID NO:5) were PCR amplified with gene-specific primers (Table 1) and were cloned into the binary vectors pBI121 and pCAMBIA1300 respectively, under the CaMV 35S promoter to generate the 35S:StBEL11 and 35S:StBEL29 constructs. These constructs were then transformed into *Agrobacterium tumefaciens* strain GV2260. Stably transformed lines were generated and ten lines of each type were selected for further expression and phenotypic analyses (FIGS. 1A-1B).

The GAS:GUS construct created in pBI101.2 was described previously (Banerjee et al., "Dynamics of a Mobile RNA of Potato Involved in a Long-Distance Signaling Pathway," *Plant Cell* 18:3443-57 (2006), which is hereby incorporated by reference in its entirety).

For generating the GAS:StBEL11 construct, the full-length StBEL11 cDNA was cloned into the XmaI/SacI site downstream from the GAS promoter, cloned previously into pBI101.2 (Banerjee et al., "Dynamics of a Mobile RNA of Potato Involved in a Long-Distance Signaling Pathway," *Plant Cell* 18:3443-57 (2006), which is hereby incorporated by reference in its entirety).

The GAS:StBEL29 construct was generated by cloning the full-length StBEL29, which was PCR amplified with primers flanking the 5' XmaI and 3' EcoRV sites, into the XmaI/SacI (blunt-ended) sites of pBI101.2 with the GAS promoter inserted previously (Banerjee et al., "Dynamics of a Mobile RNA of Potato Involved in a Long-Distance Signaling Pathway," *Plant Cell* 18:3443-57 (2006), which is hereby incorporated by reference in its entirety).

All constructs were confirmed via sequencing at the DNA Facility at Iowa State University.

These constructs were transformed into *Agrobacterium tumefaciens* strain GV2260. Wild-type potato leaves were transformed and transgenic plants were generated by *Agrobacterium*-mediated transformation as reported previously (Banerjee et al., "Efficient Production of Transgenic Potato (*S. tuberosum* L. ssp. *andigena*) Plants via *Agrobacterium Tumefaciens*-Mediated Transformation," *Plant Sci.* 170: 732-38 (2006), which is hereby incorporated by reference in its entirety). Transgenic lines for each of the four constructs were screened for level of transgene expression in at least ten independent transgenic lines, except in the case of the GAS:StBEL11 construct, where 6 lines were screened (FIGS. 1A-1B and 2A-2B). The in vitro transgenic potato plants were maintained in a growth chamber (Percival Scientific Inc.) at 27° C. with a photoperiod of 16 h light, 8 h dark and a fluence rate of 40 $\mu$mol m$^{-2}$ s$^{-1}$. Soil-grown plants were maintained in a growth chamber under either a long-day (16 h light at 22° C., 8 h dark at 18° C.) or short-day (8 h light at 22° C., 16 h dark at 18° C.) photoperiod with a fluence rate of 400 $\mu$mol m$^{-2}$ s$^{-1}$.

TABLE 1

Primers

| Cloning full-length sequences of StBEL11 and StBEL29 under 35S constitutive promoter | | SEQ ID NO: |
|---|---|---|
| BEL11F | CATCTAGAGTAGGGGGGAGGCACC | 9 |
| BEL11R | GAGAGCTCGAAGCACAAAATTTACAATATAC | 10 |
| BEL29F | ACATCTAGATTAGCTCTCATCACTTCACA | 11 |
| BEL29R | AGAGGTACCTACCACCCAAAATACTAC | 12 |

| Primers for generating StBEL11 and StBEL29 suppression lines | | SEQ ID NO: |
|---|---|---|
| StBEL11AS FP | GAGCTCGAAATTTATGGCTATGTACTATC | 13 |
| StBEL11AS RP | TCTAGAGTGGAAGACGGTATATGTGAT | 14 |
| StBEL29AS FP | GAGCTCGTGTTATTTGTTTATTGTGGAGA | 15 |
| StBEL29AS RP | TCTAGAGTCTGCTCCAACTCCGTCTA | 16 |

| StBEL11 and StBEL29 promoter cloning | | SEQ ID NO: |
|---|---|---|
| PBEL11F | TATAAGCTTAACTAACTAACTAACTGTCCC | 17 |
| PBEL11R | GAGTCTAGAACTCCACAACACATAAAGGG | 18 |
| PBEL29F | CACAAGCTTTGAGAAGAAAACCAAAGAAAC | 19 |
| PBEL29R | AACGGATCCAGATGTGGATGTGTGAATGTG | 20 |

| Cloning of StBEL11 and StBEL29 under GAS promoter | | SEQ ID NO: |
|---|---|---|
| GASBEL11f | TATATTATATCCCGGGTTTAAGAAAATCTCTCACTTTCTCT | 21 |
| GASBEL11r | TATATTATATGAGCTCGTTTACATATATGCAAATTGAAACA | 22 |
| GASBEL29f | TATATTATATCCCGGGTTCTTTCTTTCTTTCTCCTCTCT | 23 |
| GASBEL29r | TATATTATATGATATCGGCTAAAATGGATGGAGTATTATTT | 24 |

| RT-qPCR of StBEL11, StBEL29 and GAPDH | | SEQ ID NO: |
|---|---|---|
| 11F | AGGACACTAGCAAAACTTTAGG | 25 |
| 11R | CTTTGAGGC TTCCATGCATTG | 26 |
| 29F | CATTTGCCTCAACACAACCC | 27 |
| 29R | TGATGCTTTCGATCTCTGGTG | 28 |
| GAPDH-F | GAAGGACTGGAGAGGTGGA | 29 |
| GAPDH-R | GACAAC AGAAACATCAGCAGT | 30 |

TABLE 1-continued

Primers

| Transgenic-specific primers used for heterografts and screening | | SEQ ID NO: |
|---|---|---|
| NT-142 | GCGGGACTCTAATCATAAAAAC | 31 |
| GUS-GSP1 | TGGAAACGGCAGAGAAGGTAC | 32 |
| 29-GSP1 | ATTAGTGACGGACAACTTCTGTC | 33 |
| 11-GSP1 | GTAAATCAGCTTGAAATTACATCATG | 34 |

| Primers for confirming StBEL11 and StBEL29 suppression lines | | SEQ ID NO: |
|---|---|---|
| StBEL11AS RP | TCTAGAGTGGAAGACGGTATATGTGAT | 35 |
| StBEL29AS RP | CAGAAAATCCAACATATCCAG | 36 |
| NOST RPscr | GCAACAGGATTCAATCTTAAG | 37 |
| KanR FP | GGATTGCACGCAGGTTCT | 38 |
| KanR RP | CGTCAAGAAGGCGATAGAA | 39 |

| Transgene-specific primers used for RT-qPCR in RNA movement assays | | SEQ ID NO: |
|---|---|---|
| B11MqRT (GSP) | CTATATATGCAAACTATAGTATGTTG | 40 |
| B29MqRT (GSP) | CTTCTAGAAGATATATATATGGTTGAG | 41 |
| NTR (vector specific) | GCAACAGGATTCAATCTTAAGAAACT | 42 |

| RT-qPCR (Analysis of target genes) | | SEQ ID NO: |
|---|---|---|
| StACTqRTf | GGAAAAGCTTGCCTATGTGG | 43 |
| StACTqRTr | CTGCTCCTGGCAGTTTCAA | 44 |
| StPIN2qRTf | TCATCTAAAGGGCCAACACC | 45 |
| StPIN2qRTr | GTTGTATAGCTCCCCGCTCA | 46 |
| StGA2ox1qRTf | TTCTCTACAATGAGTTCACATGGTC | 47 |
| StGA2ox1qRTr | GGGACAACCTATTATCACCAAGC | 48 |
| StIAA3qRTf | CTGATCTTCGATCAATTTCATGG | 49 |
| StIAA3qRTr | GACCTATTGCTGCCTTGTGCTA | 50 |

Example 2—RNA Suppression Analysis

To generate transgenic suppression lines for StBEL11 and StBEL29, non-conserved antisense sequences were used to design constructs. The fragments (401 and 799 bp of StBEL11 and StBEL29 cDNAs, corresponding to SEQ ID NO:3 and SEQ ID NO:6, respectively) contained coding sequence and a small portion of the 5' UTR. These were amplified and cloned in the antisense direction into the binary vector pCB201 driven by the CaMV 35S promoter (Xiang et al., "A Mini Binary Vector Series for Plant Transformation," *Plant Mol. Biol.* 40:711-17 (1999), which is hereby incorporated by reference in its entirety).

Potato (*Solanum tuberosum* ssp. *andigena*) leaf transformation was performed with these two constructs as described above. Stable transformants were confirmed using PCR of genomic DNA of in vitro plantlets using gene-specific primers (Table 1). At least nine independent transgenic lines (ten plants per transgenic line) for each construct were screened for a reduction in StBEL11 and StBEL29 transcript levels in both the leaves of one-month old soil-grown long-day plants and stolons from select transgenic lines grown under short-days for 21 days (FIGS. 3A-D). Soil-grown plants (ten plants per transgenic line) were maintained in a growth chamber under a short-day (8 h light at 22° C., 16 h dark at 18° C.) photoperiod with a fluence rate of 400 µmol m$^{-2}$ s$^{-1}$. Two lines for each construct, designated 11-1, 11-2, 29-1, 29-2, were selected for further analyses.

Expression of the tuber marker gene StSP6A was quantified from stolons of the two selected lines per construct. For RT-qPCR analysis, stolons were pooled from three independent plants off ten plants per transgenic line forming three biological replicates per line. Total RNA was isolated from ground tissues using RNAiso Plus (Takara-Clontech) and two micrograms of RNA (DNase treated with RQ1 RNase-Free DNase; Cat.# M6101; Promega) were reverse-transcribed using oligo(dT) primer and SuperScript-III reverse transcriptase (Invitrogen). qPCR was performed on a CFX96 Real-Time System (BIO-RAD) using gene-specific primers (Table 1). The reactions were carried out using KAPA SYBR® green master mix (KAPA Biosystems) and incubated at 95° C. for 2 min, followed by 40 cycles of 95° C. for 15 s and 60° C. for 30 s. GAPDH was used for normalization for all the reactions (Table 1). PCR specificity was checked by melting curve analysis, and data were analyzed using the $2^{-\Delta\Delta Ct}$ method (Livak & Schmittgen, "Analysis of Relative Gene Expression Data Using Real-Time Quantitative PCR and the 2(-delta delta C(T)) Method," *Methods* 25:402-08 (2001), which is hereby incorporated by reference in its entirety). Shoot growth and tuber yield from these antisense lines were also measured. Statistical analysis was carried out with the Student's t test using GraphPad Prism (6.07 version).

Example 3—Histochemical and Fluorometric Assay

For qualitative GUS assays, samples were incubated in GUS staining buffer containing (1.0 M $NaPO_4$ pH 7, 0.25 M EDTA pH 8, 0.05 mM potassium ferricyanide, 0.05 mM potassium ferrocyanide and 1.0 mM X-gluc) for 16 h at 37° C. Samples were then washed with 100% ethanol. For histology, stained petioles and stems were cut into 0.5 cm long pieces and imbedded into 4% agarose blocks. Sections were obtained using a Leica vibratome VT1200. All samples were visualized using a Leica microscope (S8AP0). For fluorometric analysis, frozen tissue samples were ground in GUS extraction buffer (50 mM $NaPO_4$ pH 7, 10 mM EDTA pH 8.0, 10 mM β-mercaptoethanol, 0.1% Triton™ X-100 0.1% SDS) as described by Jefferson et al., "Assaying Chimeric Genes in Plants: The GUS Gene Fusion System," *Plant Mol. Biol. Rep.* 5:387-405 (1987), which is hereby incorporated by reference in its entirety. Samples were centrifuged at 17,000 rpm for 5 min. This was followed by protein quantification using the Bradford assay (Bradford et al., "A Rapid and Sensitive Method for the Quantitation of Microgram Quantities of Protein Utilizing the Principle of Protein-Dye Binding," *Anal. Biohem.* 72:248-254 (1976), which is hereby incorporated by reference in its entirety. Approximately 10 μg of the total protein was aliquoted with 5 μl of GUS assay buffer (50 mM MUG) and samples were incubated at 37° C. for 16 h. The reaction was stopped by adding stop buffer (0.2 M $Na_2CO_3$). GUS activity was monitored at emission wavelength 365 nm and excitation wavelength 455 nm using a Varioskan flash plate reader (Thermo Scientific).

Example 4—Heterografts

Simple splice micrografts under sterile conditions were made using material from 4-week old GAS:StBEL11, GAS:StBEL29, or GAS:GUS transgenic lines for scion material (shoots with 3-5 leaves) and 4-week old wildtype andigena for stocks (rooted stems approximately 1.5 cm in length). The micrografts were grown in vitro for 2 weeks before transfer to soil. In soil, the heterografts were then grown for 3 weeks under long-day conditions (16 h of light, 8 h of dark, 25° C.), followed by 2 weeks under short-days (8 h of light, 16 h of dark, 25° C.) before sample harvest, RNA extraction, and a single round of gel-based RT-PCR using transgenic gene-specific primers (Table 1).

Example 5—RT-qPCR Analysis

Eight-week old soil-grown wild-type andigena potato plants were grown under either SD or LD conditions for 15 days in a growth chamber (Percival Scientific). Leaf, petiole, stem, root, and stolon samples were then harvested in liquid nitrogen, ground and stored at −80° C. RNA was isolated from frozen samples using the RNeasy plant mini kit (QIAGEN). To avoid genomic DNA contamination, total RNA was treated with RNase-free DNase Set (QIAGEN) and quantified.

Gene-specific cDNAs for StBEL11, StBEL29, and GAPDH were prepared with 2.0 μg of total RNA using MMLV reverse transcriptase (Promega). RTqPCR was performed in a 10 μl reaction volume with primer concentrations of 0.3 μM and 1 μl of cDNA and KAPA SYBR® mastermix. The reaction mix was incubated at 95° C. for 3 min, followed by 40 cycles at 95° C. for 10 s, 55° C. for 20 s, and 60° C. for 20 s.

PCR specificity was confirmed by melting curve analysis and data were analyzed using $2^{\Delta\Delta ct}$ method (Livak & Schmittgen, "Analysis of Relative Gene Expression Data Using Real-Time Quantitative PCR and the 2(-delta delta C(T)) Method," *Methods* 25:402-08 (2001), which is hereby incorporated by reference in its entirety). GAPDH or StActin8 were used as internal controls. Gene specific primers for StBEL11, StBEL29, and GAPDH genes were used (Table 1).

Polysomal RNA extraction was performed as previously described (Mignery et al., "Isolation and Sequence Analysis of cDNAs for the Major Potato Tuber Protein, Patatin," *Nucleic Acids Res.* 12:7987-8000 (1984), which is hereby incorporated by reference in its entirety). Gene-specific primers (Table 1) with RT-qPCR were also used for the target gene assays. For all RT-qPCR analyses, the average of two or three technical replicates was first taken into consideration, followed by the statistical analyses of two or three biological replicates.

Figures 4A, 4B:
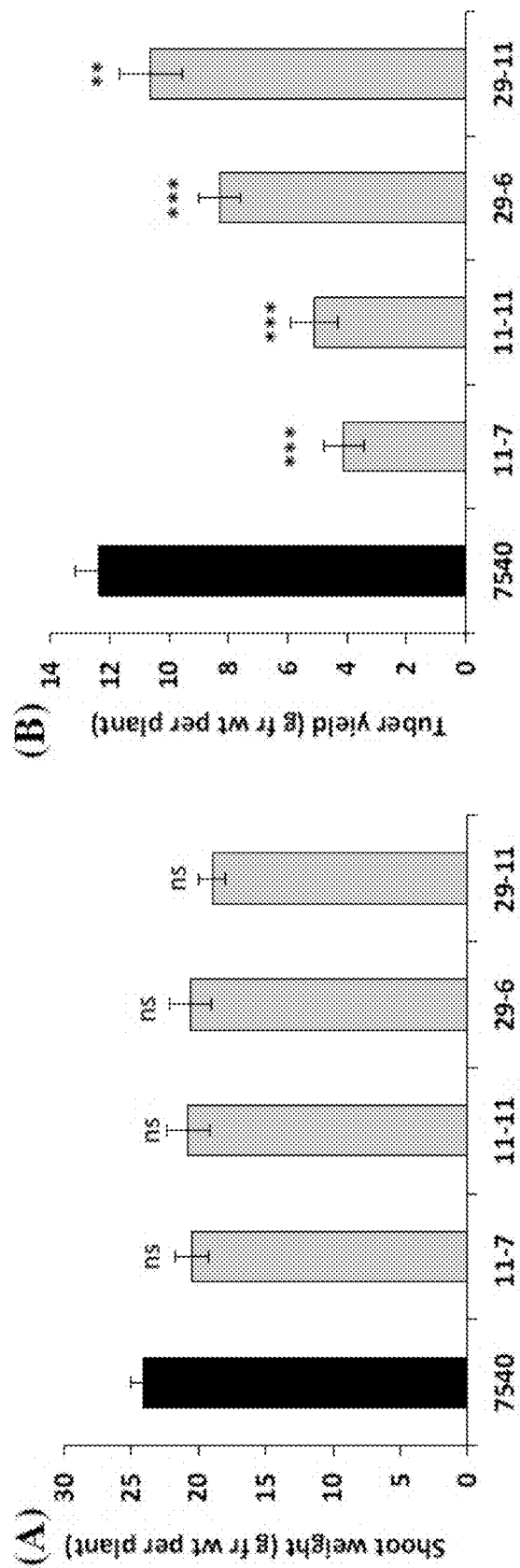
FIGS. 4A-4B depict shoot (FIG. 4A) and tuber (FIG. 4B) yields in 7540 (WT), 35S:StBEL11 (lines 7, 11) and 35S:StBEL29 (lines 6, 11) overexpression lines. Error bars represent±standard deviation of seven biological replicates. A Student's t test was performed to check significance with one, two, and three asterisks indicating $p<0.05$, $p<0.01$, and $p<0.001$, respectively. Plants were grown under long-days for 4-weeks, followed by 4-weeks under short-day conditions. ns indicates not significant.

Example 6—Phenotypes of StBEL11 and StBEL29 in Both Overexpression and Suppression Lines Because of the close sequence similarity among StBEL5, StBEL11, and StBEL29 (Sharma et al., "The BEL1-Like Family of Transcription Factors in Potato," *J. Expt. Bot.* 65:709-23 (2014), which is hereby incorporated by reference in its entirety), the possibility that StBEL11 and StBEL29 may be co-functional with StBEL5 in tuber formation was considered. To better understand the function of StBEL11 and StBEL29, approximately ten transgenic CaMV-35S over-expression (OE) lines of *S. tuberosum* ssp. *andigena* were generated for both StBEL types, screened and evaluated (FIGS. 1A-1B). Two independent lines that exhibited substantial levels of transcripts of StBEL11 and StBEL29 were used in evaluating effects on phenotypes of soil-grown plants (FIGS. 4A-4B). Overall shoot fresh weight was not affected in any of the OE lines (FIG. 4A), but a significant reduction in tuber yields was observed in all four transgenic lines (FIG. 4B).

Figures 5A, 5B, 5C:
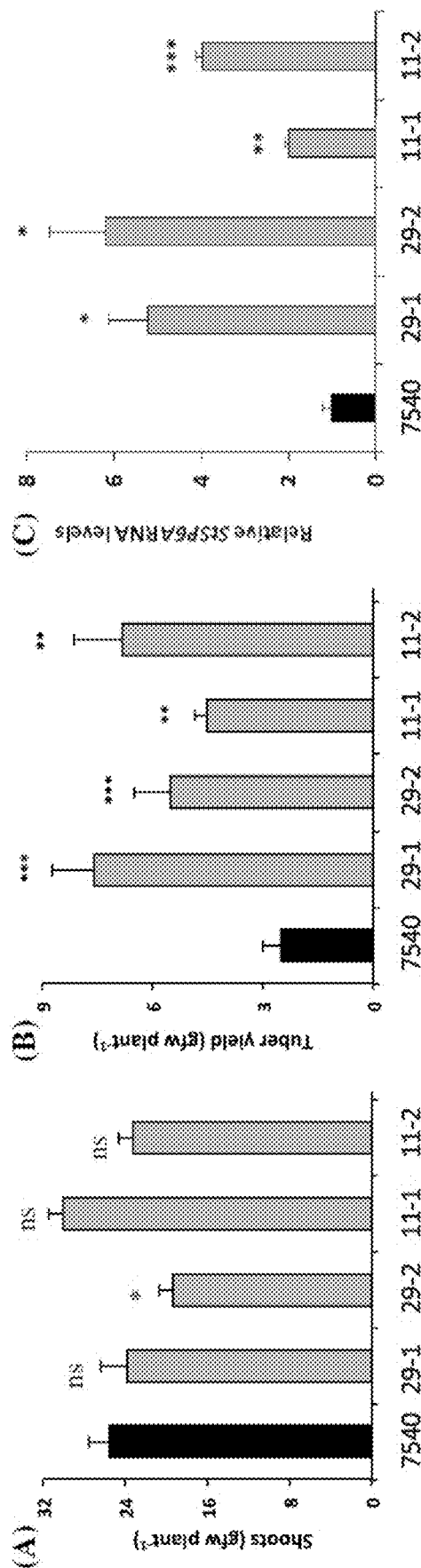
FIGS. 5A-5C are graphs showing phenotypes of antisense lines for StBEL11 (11-1, 11-2) and StBEL29 (29-1, 29-2). After screening, selected independent lines were grown for 8-weeks under long-days and then 21 days under short-day conditions. Ten independent plants for each transgenic line, including wild-type, were used for evaluating shoot growth (FIG. 5A) and tuber yields (FIG. 5B) at 21 days under short-days. Error bars represent±SD (n=10). 7540 is a non-transformed WT line. For analysis of the tuber marker gene StSP6A (FIG. 5C), RNA was harvested from stolons of plants grown under short-days for 21 days and StSP6A was quantified using RT-qPCR with gene-specific primers in selected lines for both types. Stolons were pooled from three plants off ten independent plants per transgenic line forming three biological replicates per line for RT-qPCR analysis. Three technical replicates were performed for each biological replicate for RT-qPCR. Error bars represent±standard deviation from n=3. A Student's t test was performed to check significance with one, two, and three asterisks indicating p values of <0.05, <0.01, and <0.001, respectively. ns indicates not significant.

To further validate the phenotype produced by the expression of StBEL11 and StBEL29, antisense constructs specific for each respective gene were transformed into *S. tuberosum* ssp. *andigena*. Independent lines were double screened in both leaves and stolons for suppression (FIGS. 3A-3D). Suppression levels in stolons relative to WT (wild-type) ranged from 0.3 to no suppression (FIGS. 3A-3D). From this group, two lines per construct were selected, designated as 29-1, 29-2 for StBEL29 and 11-1, 11-2 for StBEL11, and were evaluated for shoot growth and tuber yields (FIGS. 5A-5C). Whereas there was very little difference in shoot growth between WT and the antisense lines (FIG. 5A), tuber yields increased substantially under the short-day conditions (FIG. 5B). Among these four lines, increases in tuber yields ranged from two- to three-fold.

Figure 6A:
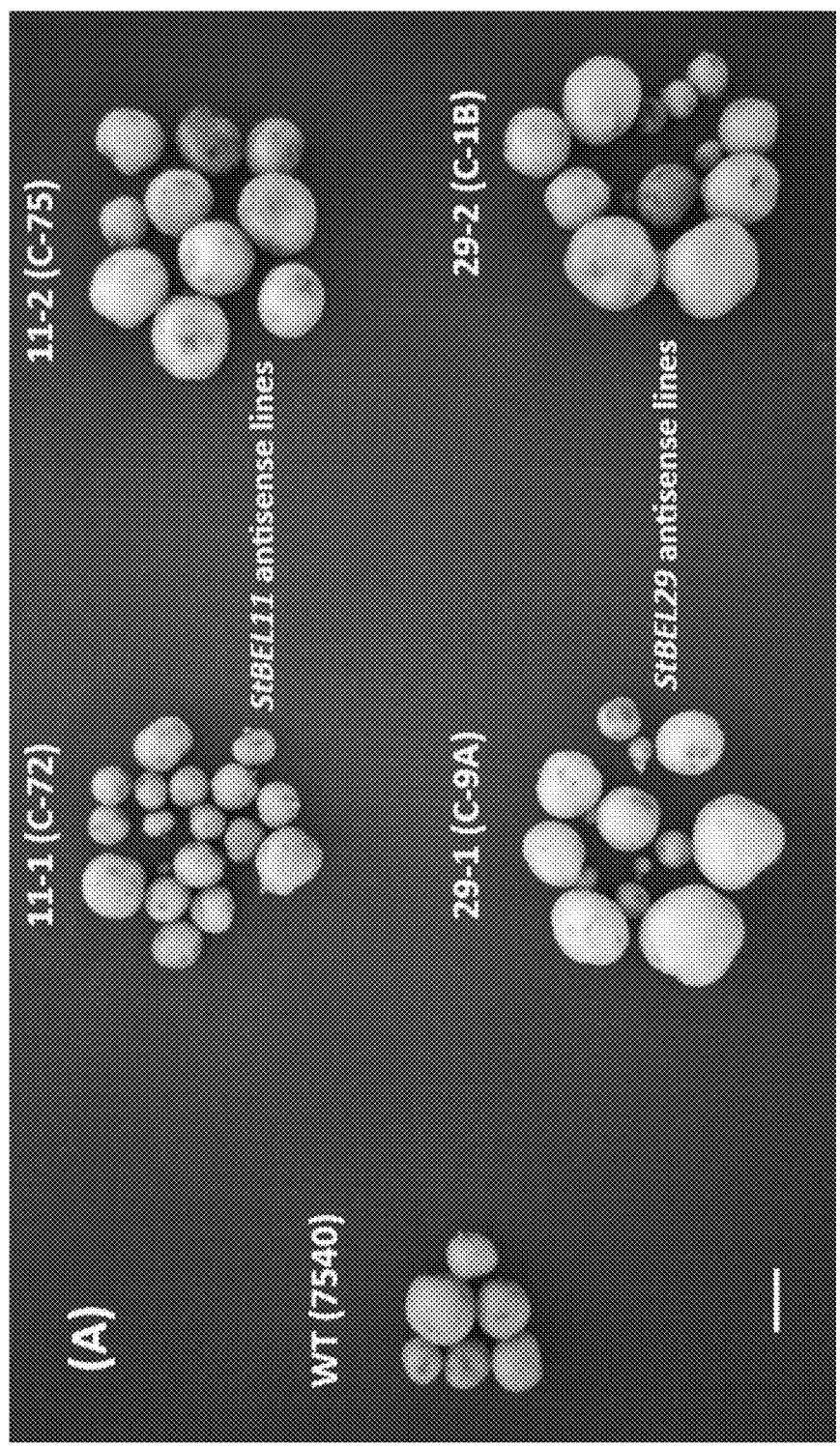
FIGS. 6A-6C show results of tubers from 35S:antisense RNA lines for StBEL11 and StBEL29 (FIG. 6A). Plants were grown in a growth chamber for eight weeks under long days and then 21 days under short-day conditions before harvest. 7540 is a non-transformed wild-type line. For each line, tubers are pooled from three plants. White bar=1.0 cm. The mean number of tubers per plant are shown for antisense lines of StBEL11 (FIG. 6B) and StBEL20 (FIG. 6C). The arrows in FIGS. 6B-6C indicate the lines shown in the photo (FIG. 6A).
Figures 6B, 6C:
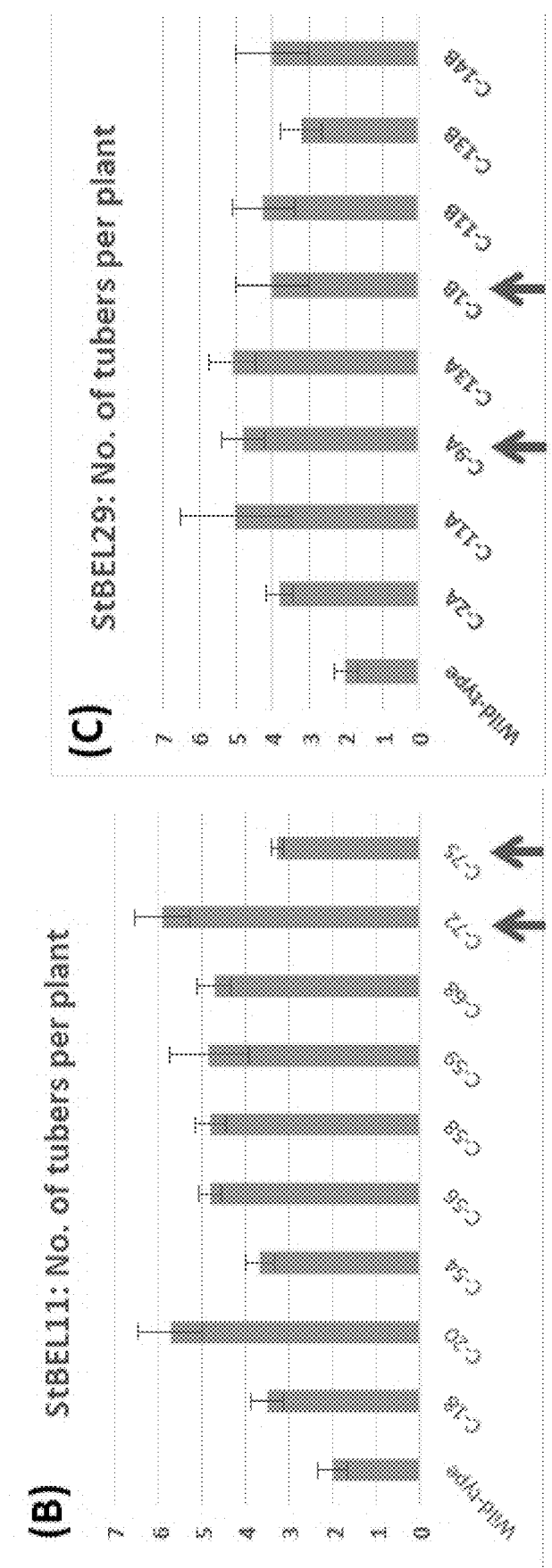

Overall tuber numbers per plant increased in these transgenic lines but the morphology of the tubers from the antisense lines appeared to be comparable to WT (FIGS. 6A-6C). To verify that this yield effect was mediated through the tuberization signaling pathway, expression of the tuber signal gene, StSP6A, was quantified in stolons of all four lines (FIG. 5C). Mean transcript levels of StSP6A increased by as much as five-fold relative to the control, and were closely correlated to overall tuber yield increase (FIGS. 5B, 5C). These results suggest that similar to StBEL5 (Sharma et al., "Targets of the StBEL5 Transcription Factor Include the FT Ortholog StSP6A," *Plant Physiol.* 170:310-24 (2016), which is hereby incorporated by reference in its entirety), StSP6A is targeted by StBEL11 and StBEL29 to control its transcriptional activity and regulate the tuberization pathway.

Example 7—Transcriptional Activity of StBEL11 and StBEL29

Figures 7A, 7B, 7C, 7D, 7E, 7F, 7G, 7H, 7I:
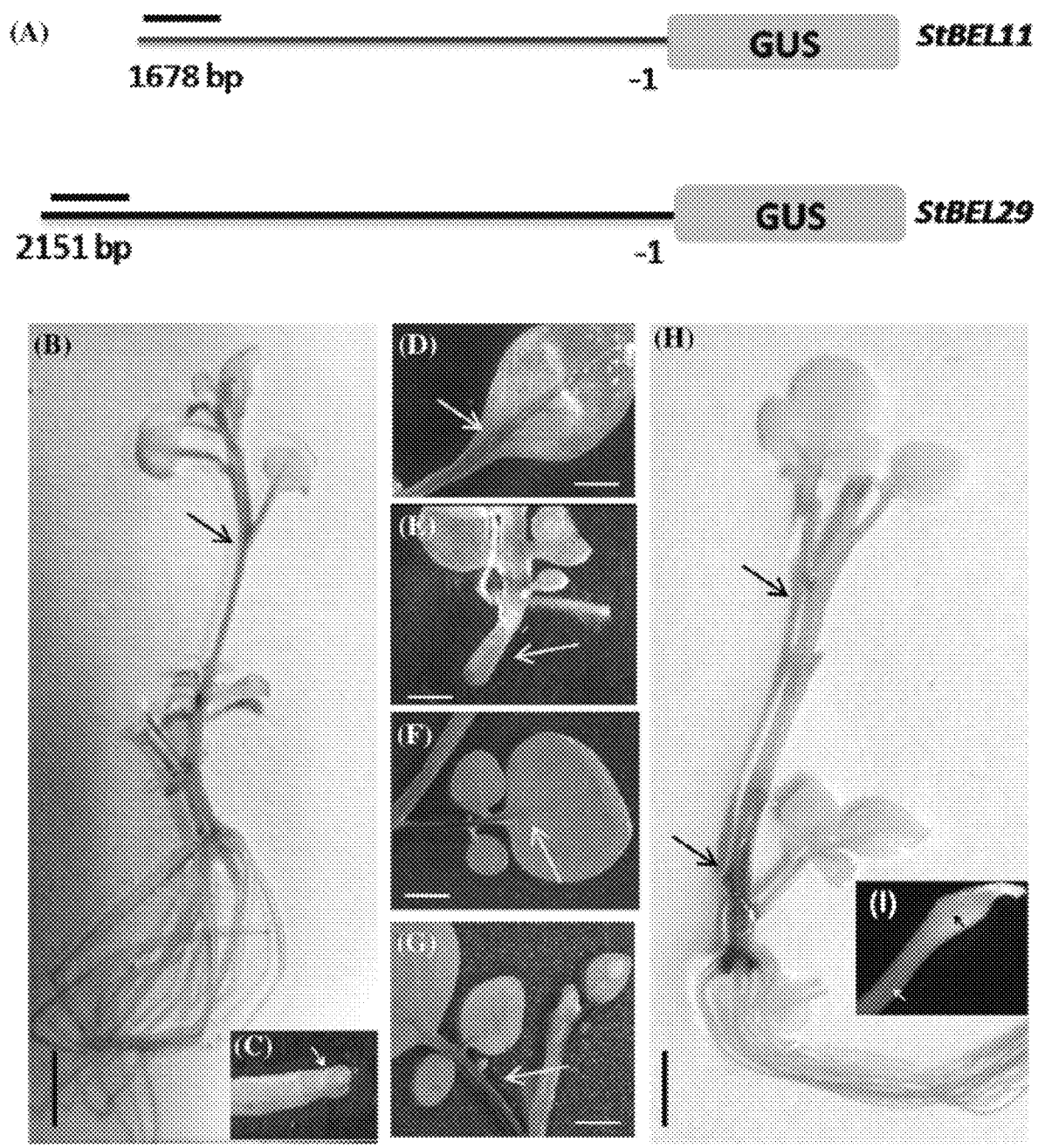
FIGS. 7A-7I show Promoter:GUS constructs of upstream sequence of StBEL11 and StBEL29. The scale bar in FIG. 7A is equivalent to 200 bp. GUS expression driven by promStBEL11 (FIGS. 7B, 7D, and 7E) and promStBEL29 (FIGS. 7F-7H) in 2 week old in vitro transgenic plants. GUS expression was observed in the midvein, petioles, and stems. Both promoter fusion lines were also grown in soil for 8-weeks in growth chambers under long-days and were then subjected to short-day conditions for 15 more days. GUS expression is shown in stolon from promStBEL11 (FIG. 7C, arrow) and swollen stolon from prom-StBEL29 (FIG. 7I, arrows). Scale bar equivalent to 0.5 cm in FIGS. 7B and 7H, and 500 µm for FIGS. 7D-7G.

To assess expression patterns in whole plants, upstream sequences of the StBEL11 and StBEL29 genes were isolated and fused to β-glucoronidase gene (GUS) and cloned into the binary vector pBI121 to generate proStBEL11:GUS and proStBEL29:GUS constructs (FIG. 7A). These were transformed into potato, *S. tuberosum* ssp. *andigena*, and ten lines for each construct were screened through histochemical GUS expression assays. Robust GUS activity was observed in primary leaf veins, petioles, and stems of both proStBEL11:GUS (FIGS. 7B, 7D, 7E, arrows) and proStBEL29: GUS (FIGS. 7F-7H, arrows) lines. GUS expression was not observed in roots of any of the in vitro grown transgenic lines tested (FIGS. 7B, 7H), and only faint GUS staining was observed in stolons from 21 day SD-induced plants (FIGS. 7C, 7I). Previous studies had shown the presence of StBEL11 and StBEL29 transcripts in phloem cells of potato (Yu et al., "Tissue Integrity and RNA Quality of Laser Microdissected Phloem of Potato," *Planta* 226:797-803 (2007), which is hereby incorporated by reference in its entirety). RNA-seq data from phloem-associated cells of petioles and stems (Lin et al., "Transcriptional Analysis of Phloem-Associated Cells of Potato," *BMC Genom.* 16:665 (2015), which is hereby incorporated by reference in its entirety) revealed substantial amounts of RNA from several StBEL genes accumulating in these cells (Table 2). The greatest levels were observed for the mobile RNA, StBEL5, and for StBEL29 (Table 2).

TABLE 2

Accumulation of Known Mobile mRNAs (*) and Selected StBELs in Petiole and Stem Phloem-Associated Cells

| Annotation | Gene ID | Petiole phloem | Stem phloem | Function | Citation |
|---|---|---|---|---|---|
| StGAI* | PGSC0003DMG400015692 | 531 | 422 | Leaf morphology | [a]Haywood |
| POTH1* | PGSC0003DMG400013493 | 267 | 24 | Vegetative growth | [b]Mahajan |
| StBEL5* | PGSC0003DMG400005930 | 2089 | 1234 | Tuber/root growth | [c]Banerjee |
| StBEL11* | PGSC0003DMG400019635 | 92 | 85 | Tuber growth | This report |
| StBEL29* | PGSC0003DMG400021323 | 1282 | 2591 | Tuber growth | This report |
| StBEL33 | PGSC0003DMG400024267 | 464 | 812 | Unknown | [e]Sharma |
| StBEL34 | PGSC0003DMG400008057 | 199 | 66 | Unknown | [e]Sharma |
| StBEL35 | PGSC0003DMG400019142 | 301 | 453 | Unknown | [e]Sharma |

*indicates known mobile mRNAs.
[a]Haywood et al., "Phloem Long-Distance Trafficking of GIBBERELLIC ACID-INSENSITIVE RNA Regulates Leaf Development," *Plant J.* 42: 49-68 (2005), which is hereby incorporated by reference in its entirety.
[b]Mahajan et al., "The mRNA of a Knotted1-Like Transcription Factor of Potato is Phloem Mobile," *Plant Mol. Biol.* 79: 595-608 (2012), which is hereby incorporated by reference in its entirety.
[c]Banerjee et al., "Dynamics of a Mobile RNA of Potato Involved in a Long-Distance Signaling Pathway," *Plant Cell* 18: 3443-57 (2006), which is hereby incorporated by reference in its entirety.
[d]Sharma et al., "The BEL1-Like Family of Transcription Factors in Potato," *J. Expt. Bot.* 65: 709-23 (2014), which is hereby incorporated by reference in its entirety.

The values for petiole and stem phloem are the means of the number of reads for three replicates of RNA-seq data from Lin et al., "Transcriptional Analysis of Phloem-Associated Cells of Potato," *BMC Genom.* 16:665 (2015), which is hereby incorporated by reference in its entirety. After sequencing, reads were processed and aligned to the potato genome. The number of concordant unique reads in each library was counted with HTseq, and the three libraries were normalized with the 0.75 quantile to eliminate the differences caused by the sample scale and sequencing depth.

Figures 8A, 8B, 8C, 8D:
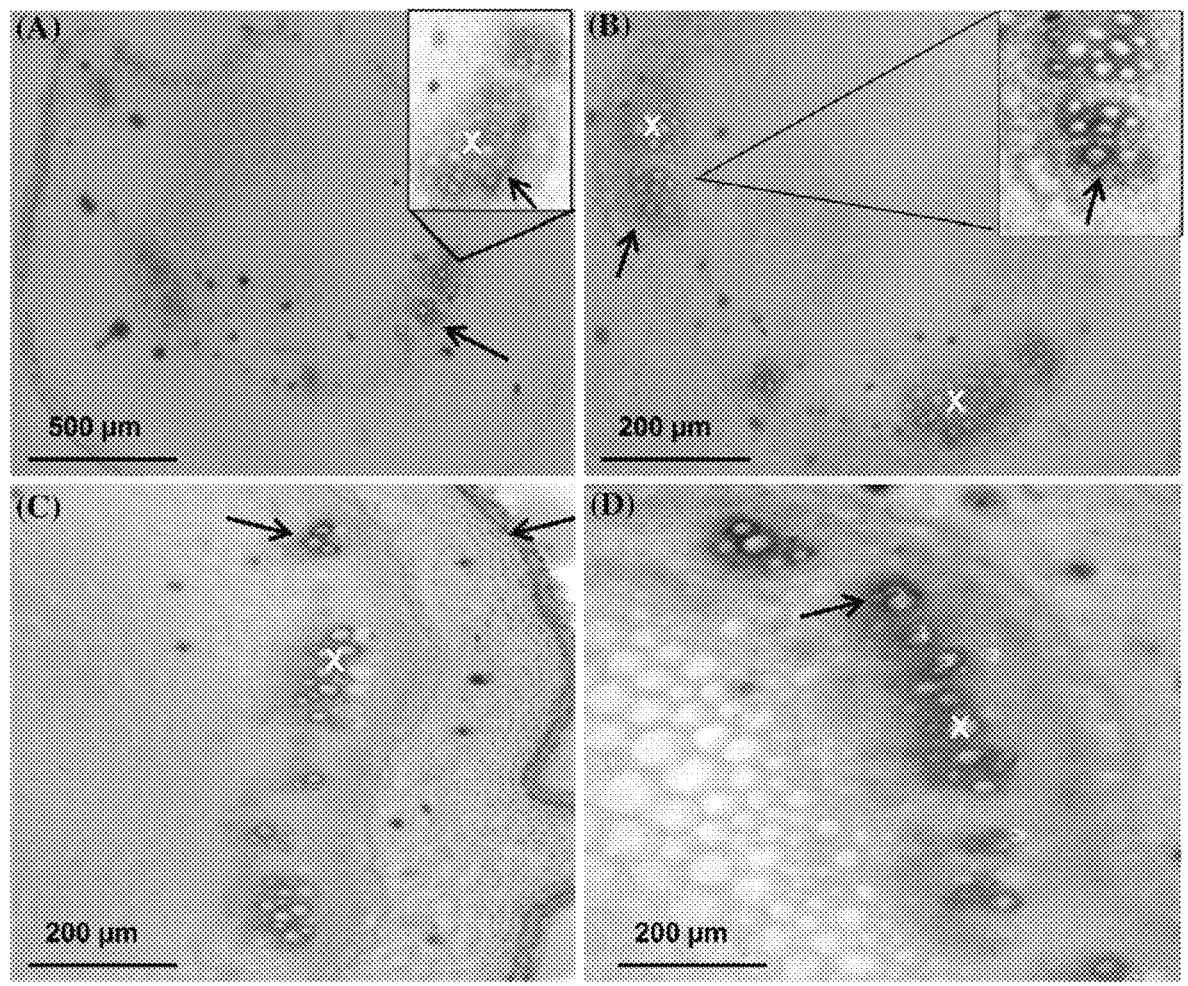
FIGS. 8A-8D show GUS activity in 8-week soil-grown proStBEL11:GUS (FIGS. 8A and 8C) and proStBEL29:GUS transgenic lines (FIGS. 8B and 8D) cultured under long-day conditions for 6 weeks and then under short-day conditions for two-weeks. Transverse sections of petioles (FIGS. 8A and 8B) and stems (FIGS. 8C and 8D) of proBEL11:GUS (FIGS. 8A and 8C) and proBEL29:GUS (FIGS. 8B and 8D) transgenic lines. The arrows in FIGS. 8A and 8B designate external phloem cells. The arrows in FIG. 8C designate xylem cells and the epidermis. The arrow in FIG. 8D designates vascular bundles. X indicates xylem cells.

To assess the cellular location of promoter activity for StBEL11 and StBEL29 in vascular cells of petioles and stems, histochemical analysis was performed on samples taken from soil-grown proStBEL11:GUS and proStBEL29: GUS transgenic lines grown under short-day conditions. GUS activity was visually assessed in transverse sections of both tissue types (FIGS. 8A-8D). Strong GUS activity was observed for both promoter lines in external phloem cells and in xylem cell walls in petioles for both StBEL11 and StBEL29 promoter transgenic lines (FIGS. 8A, 8B, arrows). GUS signal was also specifically observed in xylem cell walls and in double layers of the epidermis in stems of StBEL11 (FIG. 8C, arrows) and in phloem and xylem cell walls of stems for StBEL29 (FIG. 8D, arrows).

Example 8—Effect of Photoperiod on StBEL11 and StBEL29 mRNA Accumulation Patterns Phylogenetic analysis of the thirteen BEL TFs identified from potato revealed that StBEL11 and StBEL29 exhibited a very close amino acid sequence match with StBEL5 (Chen et al., "Interacting Transcription Factors From the Three Amino Acid Loop Extension Superclass Regulate Tuber Formation," *Plant Physiol.* 132:1391-1404 (2003) and Sharma et al., "The BEL1-Like Family of Transcription Factors in Potato," *J. Expt. Bot.* 65:709-23 (2014), which are hereby incorporated by reference in their entirety). StBEL5 mRNA accumulation and mobility were enhanced by short-days in a transport-mediated process (Banerjee et al., "Dynamics of a Mobile RNA of Potato Involved in a Long-Distance Signaling Pathway," *Plant Cell* 18:3443-57 (2006) and Cho et al., "Polypyrimidine Tract-Binding Proteins of Potato Mediate Tuberization Through an Interaction With StBEL5 RNA," *J. Expt. Bot.* 66:6835-47 (2015), which are hereby incorporated by reference in their entirety).

Figures 9A, 9B, 9C, 9D:
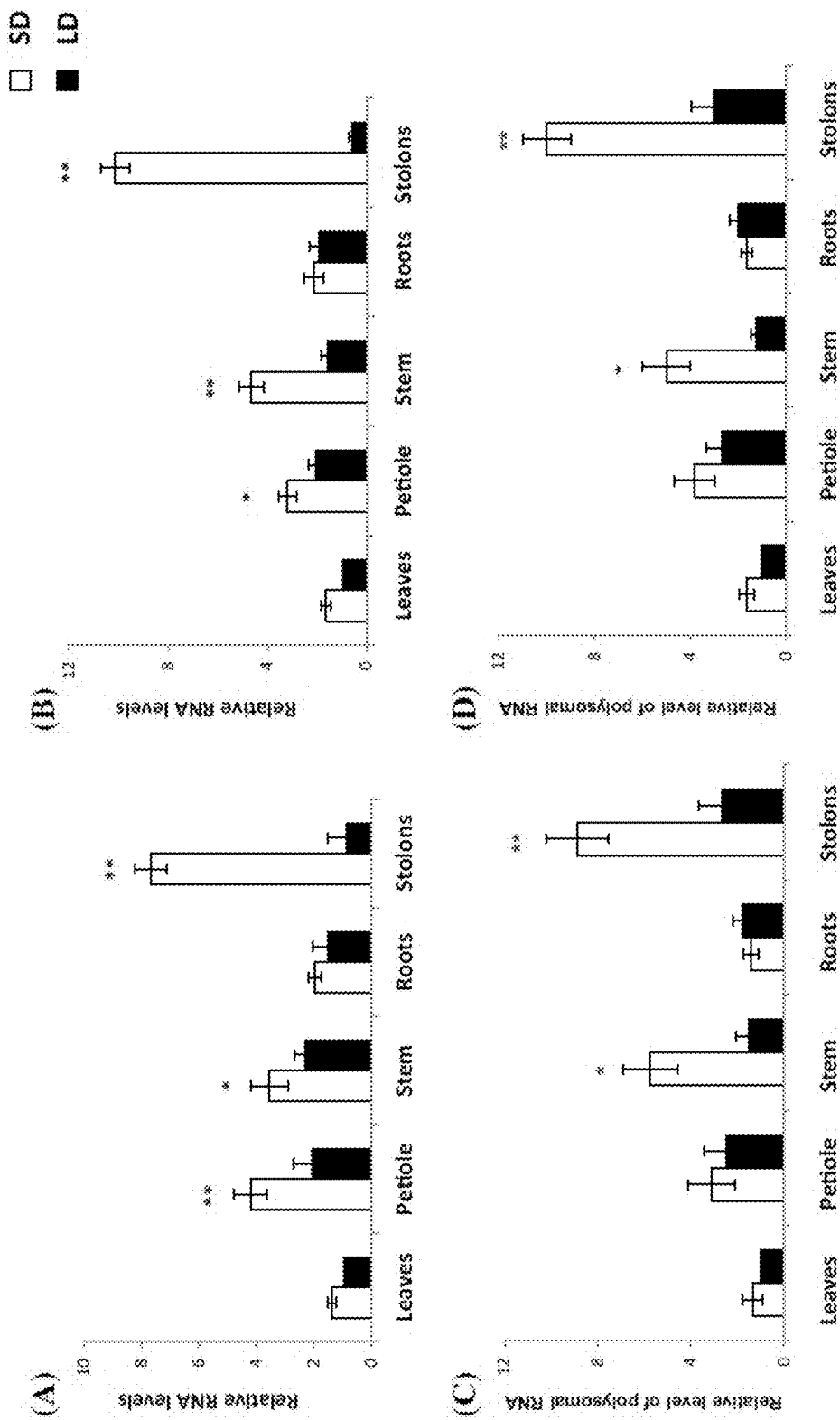
FIGS. 9A-9D show relative accumulation of total (FIGS. 9A and 9B) and polysomal (FIGS. 9C and 9D) RNA of StBEL11 (FIGS. 9A and 9C) and StBEL29 (FIGS. 9B and 9D) in WT potato (Solanum tuberosum ssp. andigena) plants under short-day and long-day photoperiods. RT-qPCR was performed on RNA from leaves, petioles, stem, roots, and stolons from 8-week soil-grown plants incubated under short-day (white bar) and long-day (black bar) for 15 days. Data represented is normalized with GAPDH. Ct value for long-day leaves set at 1.0. The values shown are the average of three biological replicates±standard deviation. A Student's t test was performed to check significance with one and two asterisks indicating $p<0.05$ and $p<0.01$, respectively.

Because photoperiod is an important cue for regulating the onset of tuberization, and to determine if photoperiod had any effect on the steady-state levels of StBEL11 and StBEL29 mRNAs, total and polysomal RNA levels for both were measured in leaves, petioles, stem, roots, and stolons from LD and SD andigena plants (FIGS. 9A-9D). Transcript accumulation of both StBEL11 and StBEL29 occurred throughout the plant under both LD and SD photoperiods, but organ-specific differential accumulation of mRNAs was observed when plants were grown under SD conditions (FIGS. 9A, 9B).

Significant differences in mRNA levels were observed for petioles, stems, and stolons for both StBEL types. In the tested samples, RNA levels were less in leaves in comparison to petiole and stems. RNA levels of both StBEL11 and StBEL29 were similar in roots under both photoperiodic conditions. Among all the organs evaluated, stolons exhibited the greatest RNA accumulation under SD conditions for both StBEL11 and StBEL29 RNAs. Similar patterns of accumulation were also observed for polysomal RNA fractions for both of the StBEL1-types (FIGS. 9C, 9D).

Figures 10A, 10B:
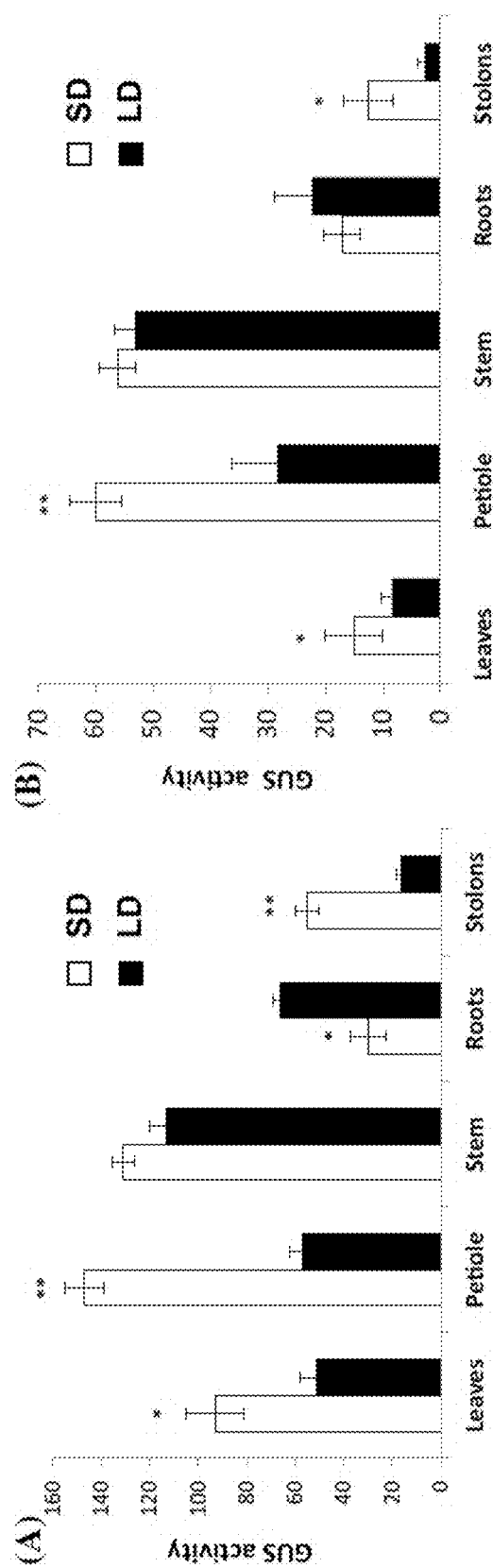
FIGS. 10A-10B show the effect of photoperiod on promoter activity of StBEL11 (FIG. 10A) and -29 (FIG. 10B). Tissue specific GUS activity in proStBEL11:GUS and proStBEL29:GUS lines was measured under both long-day (16 h light, 8 h dark) and short-day (8 h light, 16 h dark) conditions. Both promoter fusion lines were grown in soil for 8 weeks in growth chambers under long days and were then subjected to either long-day (black bars) or short-day (open bars) conditions for 15 more days. Quantification was performed using a fluorometric assay with 4-methylumbelliferyl-β-D-glucuronide as substrate. Data represent the mean±standard deviation of GUS activity measured in three biological replicates. GUS activity is expressed as nmol 4-methylumbelliferone µg protein$^{-1}$ hr$^{-1}$. A Student's t test was performed to check significance with one and two asterisks indicating $p<0.05$ and $p<0.01$, respectively. Quantitative GUS activity in respective tissues (long-day) were used as a reference in statistical analyses of both panels (FIGS. 10A and 10B).

In theory, polysomal RNA is a measure of mRNAs that are being actively translated in these organs. This analysis indicates that transcript accumulation patterns varied among the organs tested, but that levels in petioles, stems, and stolons were significantly affected by photoperiod. Levels of total RNA in stolons from SD plants increased 7.6- and 10-fold for StBEL11 and StBEL29, respectively. Similar enhancement levels were observed in the polysomal fractions (FIGS. 9C, 9D). To better understand, the effect of photoperiod on StBEL11 and StBEL29 patterns of transcript accumulation, promoter activity of both types were quantified under both LD and SD conditions in several organs (FIGS. 10A, 10B). Both StBEL1-types responded to photoperiod in a similar fashion. Promoter activity was induced by SD in leaves, petioles, and stolons. Activity in roots was slightly enhanced by LD conditions. No difference in promoter activity was observed in stems (FIGS. 10A, 10B).

Example 9—StBEL11 and StBEL29 RNAs are Phloem Mobile

Because StBEL11 and StBEL29 transcription occurs in vascular cells of both stems and petioles and in light of the liberal mobility of StBEL5 RNA, heterografts were implemented to assess the capacity of these RNAs for long-distance transport. Heterografts were composed of transgenic scions with a GAS (galactinol synthase) promoter driving full-length StBEL11 or -29 expression and wild-type (WT) stocks (FIGS. 11A-11C). The GAS promoter is specifically expressed in minor veins of the leaf (Ayre et al., "Functional and Phylogenetic Analyses of A Conserved Regulatory Program in the Phloem of Minor Veins," *Plant Physiol.* 133:1229-39 (2003), which is hereby incorporated by reference in its entirety). After grafts formed in vitro and several weeks of growth in soil, RTPCR with transgene-specific primers was performed in secondary roots and stolons of the WT andigena stock. In all four replicates for both StBEL11 and StBEL29, transgenic RNA was detected in stolons tips and secondary roots of the WT stock (FIGS. 11A, 11B). No GUS transcripts were detected in WT stocks of the GAS:GUS/WT heterografts and no transgenic RNAs were detected in WT/WT grafts (FIGS. 11C, 11D). These results clearly demonstrate that the leaf-derived transcripts of both StBEL11 and StBEL29 move down into secondary roots and stolon tips through the sieve element system when expressed from the GAS promoter.

To assess the effect of photoperiod on StBEL11 and StBEL29 mobility, levels of transgenic RNAs were measured in stolon tips of GAS:StBEL11 and GAS:StBEL29 lines grown under either LD or SD conditions using RTqPCR (FIG. 12). In all four transgenic lines for StBEL11 and StBEL29, more transgenic RNA arising from the leaf accumulated in stolon tips from plants grown under short-days than long-days. These results suggest that movement of the transgenic StBEL11 and StBEL29 RNAs is enhanced under SD conditions. Consistent with StBEL5 RNA (Cho et al., "Polypyrimidine Tract-Binding Proteins of Potato Mediate Tuberization Through an Interaction With StBEL5 RNA," *J. Expt. Bot.* 66:6835-47 (2015), which is hereby incorporated by reference in its entirety), however, enhanced stability mediated by SDs may also contribute to these steady-state level increases. Whereas shoot fresh weight from these GAS lines was generally not affected by the enhanced levels of StBEL11 and StBEL29 RNA (FIG. 13A), tuber growth was significantly reduced in these lines grown under SD conditions (FIG. 13B; FIG. 14). This reduction appears to be positively correlated with the efficient movement and stability of both RNAs into stolons under SD conditions (FIG. 12).

Example 10—Target Gene Activity

Since GAS:StBEL11 and StBEL29 lines exhibited a reduction in tuber yield (FIG. 13B), the activity of select target genes was measured in tuberizing stolons of these transgenic lines. Although accumulation of RNAs for StSP6A and StPIN1 was enhanced in a GAS:StBEL5 line relative to the WT line (Sharma et al., "Targets of the StBEL5 Transcription Factor Include the FT Ortholog StSP6A," *Plant Physiol.* 170:310-24 (2016), which is hereby incorporated by reference in its entirety), levels of RNA for these same marker genes were reduced significantly for both GAS:StBEL11 and StBEL29 transgenic lines (FIGS. 15A, 15B). Both of these genes contain a tandem TTGAC element within 2.0 kb (from the start codon) of their upstream sequence, and both are strongly induced by StBEL5 activity (Hannapel et al., "Phloem-Mobile Messenger RNAs and Root Development," *Front. Plant. Sci.* 4:257 (2013) and Sharma et al., "Targets of the StBEL5 Transcription Factor Include the FT Ortholog StSP6A," *Plant Physiol.* 170:310-24 (2016), which are hereby incorporated by reference in their entirety). The suppressive effect of StBEL11 and StBEL29 on these target genes appears not to be mediated by a reduction in levels of StBEL5 activity. In an independent experiment examining stolons of GAS:StBEL11 and StBEL29 lines, StBEL5 RNA levels were essentially unchanged or increased only in transgenic line G:B11b (FIG. 16).

Example 11—StBEL11 and StBEL29 Function Antagonistically to StBEL5

Potato tuberization is controlled by signals that arise from the leaf under inductive conditions and are transported underground via the sieve element system to activate cell growth in the stolon meristem (Abelenda et al., "Flowering and Tuberization: A Tale of Two Nightshades," *Trends Plant Sci.* 19:115-22 (2014), which is hereby incorporated by reference in its entirety). Because of their transport capacity, the search for these activating signals has focused on primary products like miRNAs, full-length mRNAs, and less abundant proteins that move through phloem cells in a basipetal direction. In addition to full-length mRNAs, like StBEL5, other prominent mobile tuberization signals have been identified. These include like the FT-ortholog, StSP6A, a key regulator of tuberization (Navarro et al., "Control of Flowering and Storage Organ Formation in Potato by FLOWERING LOCUS T," *Nature* 478:119-22 (2011), which is hereby incorporated by reference in its entirety). StSP6A protein accumulates in stolons of plants grown under SD and its expression is closely correlated with tuber formation (Navarro et al., "Control of Flowering and Storage Organ Formation in Potato by FLOWERING LOCUS T," *Nature* 478:119-22 (2011) and Gonzalez-Schain et al., "Potato CONSTANS is Involved in Photoperiodic Tuberization in a Graft-Transmissible Manner," *Plant J.* 70:678-90 (2012), which are hereby incorporated by reference in their entirety).

Two important miRNAs, miR172 and miR156, have also been implicated in potato development (Martin et al., "Graft-Transmissible Induction of Potato Tuberization by the MicroRNA miR172," *Development* 136:2873-81 (2009) and Bhogale et al., "MicroRNA156: A Potential Graft-Transmissible MicroRNA That Modulates Plant Architecture and Tuberization in *Solanum tuberosum* ssp. *andigena*," *Plant Physiol.* 164:1011-27 (2014), which are hereby incorporated by reference in their entirety). Through transcript profiling of phloem sap, it is now known that hundreds of full-length mRNAs are present in the sieve element system (Omid et al., "Characterization of Phloem-Sap Transcription Profile in Melon Plants," *J. Exp. Bot.* 58:3645-56 (2007); Deeken et al., "Identification of *Arabidopsis thaliana* Phloem RNAs Provides a Search Criterion for Phloem-Based Transcripts Hidden in Complex Datasets of Microarray Experiments," *Plant J.* 55:746-59 (2008); Kehr et al, "Long Distance Transport and Movement of RNA Through the Phloem," *J. Exp. Bot.* 59:85-92 (2008); and Notaguchi et al., "Identification of mRNAs That Move Over Long Distances Using an RNA-Seq Analysis of *Arabidopsis/Nicotiana benthamiana* Heterografts," *Plant Cell Physiol.* 56:311-21 (2015), which are hereby incorporated by reference in their entirety).

Despite these insights, however, only a limited number of RNAs have been confirmed to move and even fewer have been associated with a phenotype. This latter group includes StBEL5 (Banerjee et al., "Dynamics of a Mobile RNA of Potato Involved in a Long-Distance Signaling Pathway," *Plant Cell* 18:3443-57 (2006), which is hereby incorporated by reference in its entirety) and POTH1 (Mahaj an et al., "The mRNA of a Knotted1-Like Transcription Factor of Potato is Phloem Mobile," *Plant Mol. Biol.* 79:595-608 (2012), which is hereby incorporated by reference in its entirety) of potato, CmGAI of pumpkin (Haywood et al., "Phloem Long-Distance Trafficking of GIBBERELLIC ACID-INSENSITIVE RNA Regulates Leaf Development," *Plant J.* 42:49-68 (2005), which is hereby incorporated by reference in its entirety), PFP-LeT6 from tomato (Kim et al., "Developmental Changes Due to Long-Distance Movement of a Homeobox Fusion Transcript in Tomato," *Science* 293:287-89 (2001), which is hereby incorporated by reference in its entirety), and AUX/IAA (Notaguchi et al., "Phloem-Mobile Aux/IAA Transcripts Target to the Root Tip and Modify Root Architecture," *J. Int. Plant Biol.* 54:760-72 (2012), which is hereby incorporated by reference in its entirety) and FLOWERING LOCUS T and CENTRORADIALIS (Li et al., "Mobile FT mRNA Contributes to the Systemic Florigen Signalling in Floral Induction," *Sci. Rep.* 1:73 (2011); Huang et al., "*Arabidopsis* CENTRO-RADIALIS Homologue Acts Systemically to Inhibit Floral Initiation in *Arabidopsis*," *Plant J.* 72:175-84 (2012); and Lu et al., "Long-Distance Movement of *Arabidopsis* FLOWERING LOCUS T RNA Participates in Systemic Floral Regulation," *RNA Biol.* 9(5):653-62 (2012), which are hereby incorporated by reference in their entirety) from *Arabidopsis*.

A recent report by Calderwood et al., "Transcript Abundance Explains mRNA Mobility Data in *Arabidopsis thaliana*," *Plant Cell* 28:610-15 (2016), which is hereby incorporated by reference in its entirety, indicated that movement of RNAs from phloem cells can be explained by transcript abundance and RNA stability. This study suggests that most of the identified transcripts that move from companion cells into sieve elements do so via non-sequence-specific transport. Whereas this study certainly establishes a strong case for a non-specific mechanism controlling RNA movement, there is also evidence that conserved RNA sequences that interact with specific RNA-binding proteins may mediate transcript mobility (Ham et al., "A Polypyrimidine Tract Binding Protein, Pumpkin RBP50, Forms the Basis of a Phloem-Mobile Ribonucleoprotein Complex," *Plant Cell* 21:197-215 (2009) and Cho et al., "Polypyrimidine Tract-Binding Proteins of Potato Mediate Tuberization Through an Interaction With StBEL5 RNA," *J. Expt. Bot.* 66:6835-47 (2015), which are hereby incorporated by reference in their entirety).

Because of the critical role that the polypyrimidine tract-binding (PTB) proteins play in controlling StBEL5 transcript movement and stability (Cho et al., "Polypyrimidine Tract-Binding Proteins of Potato Mediate Tuberization Through an Interaction With StBEL5 RNA," *J. Expt. Bot.* 66:6835-47 (2015), which is hereby incorporated by reference in its entirety), future work will be necessary to elucidate the processes that regulate mobility and stability for StBEL11 and StBEL29. Evidence for a more specific process is suggested, however, in the movement assays of this study. Using heterografts and the same source promoter, StBEL11 and StBEL29 RNAs moved liberally across the graft union into both roots and stolons, whereas, movement of GUS transcripts was not detected (FIGS. 11A-11C).

Whereas StBEL5 has been proposed to function as a mobile RNA signal in potato that activates tuber growth (Banerjee et al., "Dynamics of a Mobile RNA of Potato Involved in a Long-Distance Signaling Pathway," *Plant Cell* 18:3443-57 (2006) and Lin et al., "The Impact of the Long-Distance Transport of a BEL1-Like mRNA on Development," *Plant Physiol.* 161:760-72 (2013), which are hereby incorporated by reference in their entirety), here it is reported that the phylogenetically-related StBELs, StBEL11 and StBEL29, are also phloem-mobile, but act in opposition to StBEL5. Functional antagonism has been reported previously among the BEL1-like TFs, *ARABIDOPSIS THALIANA* HOMEOBOX 1, PENNYWISE and POUNDFOOLISH, in the maintenance of the SAM and in the control of flowering time (Rutjens et al., "Shoot Apical Meristem Function in *Arabidopsis* Requires the Combined Activities of Three BEL1-Like Homeodomain Proteins," *Plant J.* 58:641-54 (2009), which is hereby incorporated by reference in its entirety).

Despite their antagonistic relationship, however, StBEL5, StBEL11 and StBEL29 share a number of common features that are unique among StBEL family members. All three exhibit RNA accumulation and promoter activity associated with phloem cells (Table 2; FIGS. 8A-8D; Banerjee et al., "Dynamics of a Mobile RNA of Potato Involved in a Long-Distance Signaling Pathway," *Plant Cell* 18:3443-57 (2006); Yu et al., "Tissue Integrity and RNA Quality of Laser Microdissected Phloem of Potato," *Planta* 226:797-803 (2007); and Lin et al., "Transcriptional Analysis of Phloem-Associated Cells of Potato," *BMC Genom.* 16:665 (2015), which are hereby incorporated by reference in their entirety). Their RNAs are ubiquitous throughout the plant and both movement and accumulation of their RNAs are enhanced by a SD photoperiod. They are the only BELs of potato with transcript levels consistently affected by SDs in several organs (Chen et al., "Interacting Transcription Factors From the Three Amino Acid Loop Extension Superclass Regulate Tuber Formation," *Plant Physiol.* 132:1391-1404 (2003) and Sharma et al., "The BEL1-Like Family of Transcription Factors in Potato," *J. Expt. Bot.* 65:709-23 (2014), which are hereby incorporated by reference in their entirety), and all three exhibit enhanced accumulation of their transcripts in stolons under SD conditions.

This relationship with photoperiod suggests that their movement and stability could be controlled by a common factor. Recent work on the mobility of StBEL5 has shown that its RNA interacts with RNA-binding proteins from the PTB family, StPTB1 and StPTB6 (Cho et al., "Polypyrimidine Tract-Binding Proteins of Potato Mediate Tuberization Through an Interaction With StBEL5 RNA," *J. Expt. Bot.* 66:6835-47 (2015), which is hereby incorporated by reference in its entirety). This binding occurs on conserved cytosine/uracil motifs present in the 3' UTR of StBEL5 and facilitates stability as well as transport (Cho et al., "Polypyrimidine Tract-Binding Proteins of Potato Mediate Tuberization Through an Interaction With StBEL5 RNA," *J. Expt. Bot.* 66:6835-47 (2015), which is hereby incorporated by reference in its entirety). Similar motifs have been identified in the UTRs of StBEL11 and StBEL29 that may facilitate binding to the StPTB proteins. In over-expression lines of StPTB1 and StPTB6, movement of StBEL11 and StBEL29 from leaves to stolon tips was enhanced (FIGS. 17A-17D).

Polysomal RNA levels for StBEL11 and StBEL29 were positively correlated with overall RNA accumulation, suggesting functional activity of these TFs in those organs where they accumulate. In all three of these StBEL TFs, the effect on growth appears to be mediated by a similar set of target genes. For example, all three regulate StSP6A activity (FIGS. 5A-5C; FIGS. 15A-15B; Sharma et al., "Targets of the StBEL5 Transcription Factor Include the FT Ortholog StSP6A," *Plant Physiol.* 170:310-24 (2016), which is hereby incorporated by reference in its entirety). StBEL11 and StBEL29 appear to work on downstream target genes and have minimal effect on StBEL5 transcription (FIG. 16). StBEL5 functions upstream of a plethora of targets and induces the expression of six StBEL genes in stolons, including StBEL11 and StBEL29, and numerous genes involved in hormone metabolism (Sharma et al., "Targets of the StBEL5 Transcription Factor Include the FT Ortholog StSP6A," *Plant Physiol.* 170:310-24 (2016), which is hereby incorporated by reference in its entirety; FIG. 18). Cross-regulation by StBEL5 contributes to inducing the expression of StBEL11 and StBEL29 in stolons and other organs. In this way, all three may function jointly to maintain a balance of controlled, localized cell growth in these organs. The repressive transcription function observed for StBEL11 and StBEL29 could be the result of a unique BEL/KNOX interaction or it could be the effect of a novel sequence motif in their proteins that modulates critical structural dynamics. In an amino-acid sequence alignment of StBEL5, StBEL11, and StBEL29, eleven unique amino acid runs of eight or more residues were identified (FIG. 19). Among all three, there are very few sequence differences within the highly conserved protein/protein domains (BELL and SKY box) and the homeodomain.

Example 12—An Activator/Inhibitor Module for Tuberization

A system of activation and repression of growth is consistent with the development of a new tuber from the stolon tip. At the onset of tuber induction, the shoot apex ceases to elongate and growth is initiated in a specific layer of cells within the pith and cortex, resulting in swelling in the stolon tip that spreads throughout the subapical portion of the meristem (Xu et al., "Cell Division and Cell Enlargement During Potato Tuber Formation," *J. Exp. Bot.* 49:573-82 (1998), which is hereby incorporated by reference in its entirety). Further cell growth arises from cells between the pith and cortex designated the perimedullary zone just below the stolon apex and in close proximity to vascular tissue (Xu et al., "Cell Division and Cell Enlargement During Potato Tuber Formation," *J. Exp. Bot.* 49:573-82 (1998), which is hereby incorporated by reference in its entirety). The orientation of cell division changes from transverse to longitudinal leading to radial expansion. Most of the cell growth occurs in this localized sub-apical region of the stolon meristem (Xu et al., "Cell Division and Cell Enlargement During Potato Tuber Formation," *J. Exp. Bot.* 49:573-82 (1998), which is hereby incorporated by reference in its entirety) and changes in levels of hormones like gibberellins, auxin, and cytokinins play pivotal roles in regulating growth at this site (Xu et al., "The Role of Gibberellin, Abscisic Acid, and Sucrose in the Regulation of Potato Tuber Formation In Vitro," *Plant Physiol.* 117:575-84 (1998), which is hereby incorporated by reference in its entirety).

Growth below the apex creates a strong sink that subsequently accumulates storage proteins and large amounts of starch transported as sucrose via the phloem system. Control of these processes includes both activation and suppression of the growth of specific cell types unique to the tuberization program. Mobile TFs that are transported through sieve elements and can move cell-to-cell via plasmodesmata in the form of a full-length mRNA are ideal for the fine-tuning of cell growth and cell dormancy. Because of the high bioenergetic cost of this developing sink, the efficient coordination of cell growth is critical. Due to their mobility and specificity, this tripartite StBEL module could readily contribute to cell fate determination in the stolon apex during the transition process from stolon to tuber. Because StBEL11/29 function antagonistically to StBEL5 for tuberization, it is possible that these StBEL types function at different developmental stages or in different cell types during the stolon-to-tuber transition.

There are other examples of activation/suppression systems that regulate plant growth through maintenance of the apical meristem. One of the most widely studied systems is an activator/inhibitor process that controls flowering (Lifschitz et al., "Florigen and Anti-Florigen: A Systemic Mechanism for Coordinating Growth and Termination in Flowering Plants," *Front. Plant. Sci.* 5:465 (2014), which is hereby incorporated by reference in its entirety). Flowering locus T (FT) protein acts as a mobile florigen signal that moves into the apex and interacts with the basic leucine zipper transcription factor, FD, to induce flowering (Abe et al., "FD, A bZIP Protein Mediating Signals From the Floral Pathway Integrator FT at the Shoot Apex," *Science* 309: 1052-56 (2005); Wigge et al., "Integration of Spatial and Temporal Information During Floral Induction in *Arabidopsis*," *Science* 309:1056-59 (2005); Corbesier et al., "FT Protein Movement Contributes To Long Distance Signaling In Floral Induction of *Arabidopsis*," *Science* 316:1030-33 (2007); Jaeger & Wigge, "FT Protein Acts as a Long Range Signal in *Arabidopsis*," *Curr. Biol.* 17:1050-54 (2007); and Mathieu et al., "Export of FT Protein From Phloem Companion Cells is Sufficient for Floral Induction in *Arabidopsis*," *Curr. Biol.* 17:1055-60 (2007), which are hereby incorporated by reference in their entirety).

TERMINAL FLOWER 1-like (TFL1) proteins function as floral inhibitors and are antagonistic to FT function (Shannon & Meeks-Wagner, "A Mutation in the *Arabidopsis* TFL1 Gene Affects Inflorescence Meristem Development," *Plant Cell* 3:877-92 (1991), which is hereby incorporated by reference in its entirety). A single amino acid change in the FT protein is sufficient to transform its function from an activator to a repressor (Hanzawa et al., "A Single Amino Acid Converts a Repressor to an Activator of Flowering," *Proc. Nat'l. Acad. Sci. U.S.A.* 102:7748-53 (2005), which is hereby incorporated by reference in its entirety). There have even been reports that the mRNAs of FT and CENTRORADIALIS, a TFL1 homologue in *Arabidopsis*, move long distance to the shoot apex via the phloem system (Huang et al., "*Arabidopsis* CENTRO-RADIALIS Homologue Acts Systemically to Inhibit Floral Initiation in *Arabidopsis*," *Plant J.* 72:175-84 (2012) and Lu et al., "Long-Distance Movement of *Arabidopsis* FLOWERING LOCUS T RNA Participates in Systemic Floral Regulation," *RNA Biol.* 9(5): 653-62 (2012), which are hereby incorporated by reference in their entirety). Another report, however, indicated that FT mRNA movement is not required to induce flowering (Notaguchi et al., "Long-Distance, Graft-Transmissible Action of *Arabidopsis* FLOWERING LOCUS T Protein to Promote Flowering," *Plant Cell Physiol.* 49:1645-58 (2008), which is hereby incorporated by reference in its entirety).

In another example of an activator/repressor process that balances growth, the homeodomain TF, WUSCHEL (WUS), functions to maintain stem cells in the SAM in an undifferentiated state (Schoof et al., "The Stem Cell Population of *Arabidopsis* Shoot Meristems is Maintained by a Regulatory Loop Between the CLAVATA and WUSCHEL Genes," *Cell* 100:635-44 (2000) and Fletcher, "Shoot and Floral Meristem Maintenance in *Arabidopsis*," *Annu. Rev. Plant Biol.* 53:45-66 (2002), which are hereby incorporated by reference in their entirety). CLAVATA3 (CLV3), a peptide ligand, controls the size of the stem cell domain by repressing WUS (ádniková & Simon, "How Boundaries Control Plant Development," *Curr. Opin. Plant Biol.* 17:116-25 (2014), which is hereby incorporated by reference in its entirety). In turn, the LATERAL ORGAN BOUNDARIES DOMAIN TF, LBD15, maintains the stem cell pool through upregulation of WUS (Sun et al., "*Arabidopsis* ASL11/LBD15 is Involved in Shoot Apical Meristem Development and Regulates WUS Expression," *Planta* 237:1367-78 (2013), which is hereby incorporated by reference in its entirety). The WUS-CLV feedback system forms a self-correcting mechanism for maintaining a constant number of stem cells and the SAM size at the shoot apex.

A model for tuber formation is currently arising that places StBEL5 upstream in a regulatory network involving hormonal metabolism and transcriptional controls that mediate tuber formation (Sharma et al., "Targets of the StBEL5 Transcription Factor Include the FT Ortholog StSP6A," *Plant Physiol.* 170:310-24 (2016), which is hereby incorporated by reference in its entirety). The observation that StBEL5 induces transcription of StSP6A, whereas StBEL11, and StBEL29 suppress its expression, is consistent with this premise. Overall, these data suggest that StBEL5, StBEL11, and StBEL29 could function collectively as phloem-mobile mRNA signals in a whole-plant network in potato that modulates storage organ development through the processes of cell growth activation and suppression in the subapical portion of the stolon tip.

Although preferred embodiments are depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A nucleic acid construct comprising:
a first nucleic acid molecule comprising SEQ ID NO:3 in the antisense orientation or a nucleotide sequence that has at least 95% sequence identity to the nucleotide sequence of SEQ ID NO:3 in the antisense orientation to silence or reduce expression of SEQ ID NO:1 or a nucleotide sequence that has at least 95% sequence identity to the nucleotide sequence of SEQ ID NO:1;
a 5' DNA promoter sequence; and
a 3' terminator sequence, wherein the first nucleic acid molecule, the promoter sequence, and the terminator sequence are operatively linked to permit transcription of the first nucleic acid molecule.

2. The nucleic acid construct according to claim 1, wherein the nucleic acid construct comprises DNA heterologous to the first nucleic acid molecule.

3. The nucleic acid construct according to claim 2, wherein the DNA heterologous to the first nucleic acid molecule is the 5' DNA promoter sequence.

4. The nucleic acid construct according to claim 1 further comprising:
a second nucleic acid molecule comprising SEQ ID NO:6 in the antisense orientation or a nucleotide sequence that has at least 95% sequence identity to the nucleotide sequence of SEQ ID NO:6 in the antisense orientation to silence or reduce expression of SEQ ID NO:4 or a nucleotide sequence that has at least 95% sequence identity to the nucleotide sequence of SEQ ID NO:4.

5. The nucleic acid construct according to claim 1 further comprising:
a further nucleic acid molecule comprising SEQ ID NO:7 or a nucleotide sequence that has at least 95% sequence identity to the nucleotide sequence of SEQ ID NO:7.

6. The nucleic acid construct according to claim 5, wherein the further nucleic acid molecule comprises the nucleotide sequence of SEQ ID NO:8 or a nucleic acid molecule that has at least 99% sequence identity to the nucleotide sequence of SEQ ID NO:8.

7. The nucleic acid construct according to claim 1, wherein the promoter sequence is one or more of the following: a native, constitutive, inducible, developmentally-regulated, organelle-specific, tissue-specific, cell-specific, seed-specific, and germination-specific promoter.

8. An expression vector comprising the nucleic acid construct according to claim 1.

9. A bacterial cell or a potato cell comprising the nucleic acid construct according to claim 1.

10. A transgenic potato plant seed comprising the nucleic acid construct according to claim 1.

11. A transgenic potato plant comprising the nucleic acid construct according to claim 1, wherein the plant has increased tuber yield compared to a plant not comprising the nucleic acid construct.

12. The transgenic potato plant of claim 11, wherein the potato plant comprises an expression level of SEQ ID NO:1 less than 60% compared to a potato plant not comprising the nucleic acid construct.

13. The transgenic potato plant of claim 11 further comprising a second nucleic acid molecule comprising SEQ ID NO:6 in the antisense orientation or a nucleotide sequence that has at least 95% sequence identity to the nucleotide sequence of SEQ ID NO:6 in the anti sense orientation to silence or reduce expression of SEQ ID NO:4 or a nucleotide sequence that has at least 95% sequence identity to the nucleotide sequence of SEQ ID NO:4, wherein the potato plant comprises an expression level of SEQ ID NO:4 less than 60% compared to a potato plant not comprising the second nucleic acid molecule.

14. The transgenic potato plant of claim 11 further comprising a further nucleic acid molecule comprising SEQ ID NO:7 or a nucleotide sequence that has at least 95% sequence identity to the nucleotide sequence of SEQ ID NO:7.

15. The transgenic potato plant according to claim 11, wherein the potato plant is selected from the group consisting of *Solanum tuberosum* spp. *andigena* and *Solanum tuberosum* spp. *tuberosum*.

16. A transgenic cell of the potato plant according to claim 11.

17. A transgenic potato plant seed produced from the potato plant according to claim 11, wherein the seed comprises said nucleic acid construct.

\* \* \* \* \*